US009734298B2

(12) United States Patent
Hall et al.

(10) Patent No.: US 9,734,298 B2
(45) Date of Patent: Aug. 15, 2017

(54) PROGRAM OPTIMIZATION SYSTEM

(71) Applicant: HCA Holdings, Inc., Nashville, TN (US)

(72) Inventors: Charles J. Hall, Tallahassee, FL (US); Michael A. Marks, Nashville, TN (US); Steven V. Manoukian, Nashville, TN (US); Elio Perez, Miami, FL (US); Gabriel O. Perez Rodriguez, Miramar, FL (US)

(73) Assignee: HCA HOLDINGS, INC., Nashville, TN (US)

( * ) Notice: Subject to any disclaimer, the term of this patent is extended or adjusted under 35 U.S.C. 154(b) by 23 days.

(21) Appl. No.: 14/172,736

(22) Filed: Feb. 4, 2014

(65) Prior Publication Data

US 2014/0222451 A1 Aug. 7, 2014

Related U.S. Application Data

(60) Provisional application No. 61/760,575, filed on Feb. 4, 2013.

(51) Int. Cl.
*G06Q 50/00* (2012.01)
*G06F 19/00* (2011.01)

(52) U.S. Cl.
CPC ........ *G06F 19/345* (2013.01); *G06F 19/3431* (2013.01)

(58) Field of Classification Search
CPC ....... G06Q 50/22–50/24; G06F 19/345; G06F 19/3431
See application file for complete search history.

(56) References Cited

U.S. PATENT DOCUMENTS

| | | | |
|---|---|---|---|
| 6,347,329 B1 * | 2/2002 | Evans | 709/202 |
| 2008/0058773 A1 * | 3/2008 | John | A61N 1/3605 604/891.1 |
| 2010/0169142 A1 * | 7/2010 | Hinton et al. | 705/8 |
| 2010/0222649 A1 * | 9/2010 | Schoenberg | 600/301 |

* cited by examiner

*Primary Examiner* — Robert Sorey
(74) *Attorney, Agent, or Firm* — Kilpatrick Townsend & Stockton LLP

(57) ABSTRACT

Program optimization systems are provided herein. The program optimization system can include a plurality of data sources that can be mined for information relating to one or several patients. The format and content of the information from the data sources can be evaluated and can be conformed to formats and content types used by the program optimization system. The information retrieved from the data sources can be evaluated for one or several trigger events. If a trigger event is identified in the retrieved data, a treatment protocol can be selected.

19 Claims, 33 Drawing Sheets

100
102
120
Processor
122
118
104
Patient Data Base
105
Trigger
Schedule
Protocol
Admin
Outcome
Access
106
108
110
112
114
116

800

| Valve Disease | Severity | | |
|---|---|---|---|
| | Mild | Moderate | Severe |
| Mitral Regurgitation | | | |
| • Regurgitate volume (mL/beat) | <30 | 30-59 | ≥60 |
| • Regurgitate fraction (%) | <30 | 30-49 | ≥50 |
| • Regurgitate orifice area ($cm^2$) | <0.20 | 0.20-0.39 | ≥0.40 |
| Mitral Stenosis | | | |
| • Mean gradient (mmHg) | <5 | 5-10 | >10 |
| • Valve area ($cm^2$) | >1.5 | 1.0-1.5 | <1.0 |
| • PA systolic pressure (mmHg) | <30 | 30-50 | >50 |
| Aortic Stenosis | | | |
| • Aortic jet velocity (m/sec) | <3.0 | 3.0-4.0 | >4.0 |
| • Mean gradient (mmHg) | <25 | 25-40 | >40 |
| • Valve area ($cm^2$) | >1.5 | 1.0-1.5 | <1.0 |

Four Principal Categories for Radiology Follow-up Recommendations

| | 1 | 2 | 3 | 4 |
|---|---|---|---|---|
| **Recom-mendation** | Surveillance & serial monitoring | Additional Diagnostic imaging | Consider for thera-peutic intervention | Recommend imme-diate intervention |
| **Example** | Annual abdominal CT scan for AAA monitoring | CT angiogram to evaluate severity of CAS | Vascular surgery referral for symptomatic PAD | Immediate consult for evaluation of carotid 'string sign' |
| **Provider of outpatient next steps** | PCP | PCP | Specialist | Specialist |

*Figure 16*

PROGRAM OPTIMIZATION SYSTEM

CROSS-REFERENCES TO RELATED APPLICATIONS

This application claims the benefit of U.S. Provisional Application No. 61/760,575, entitled PROGRAM OPTIMIZATION SYSTEM, and filed Feb. 4, 2013, the entirety of which is hereby incorporated by reference herein.

BACKGROUND OF THE INVENTION

Patient diagnosis and treatment are increasingly problematic as physicians attempt to treat growing numbers of patients. These challenges further increase with the current and likely future downward price pressure on medical services. In light of these pressures and demands, new systems and methods are required to facilitate physicians and medical professionals in providing treatment to patients.

BRIEF SUMMARY OF THE INVENTION

Some embodiments of the present disclosure relate to a method of identifying a member of a healthcare organization for potential treatment. The method includes retrieving patient data, which patient data can identify a plurality of patients, identifying a patient from the patient data, and retrieving data source information that identifies a plurality of data sources. In some embodiments, these data sources can originate clinical results relating to aspects of patient health. The method can include identifying a first data source from the data source information as the source of a first clinical result, retrieving the first clinical result from the first data source, and identifying a categorization of the first clinical result. In some embodiments, the categorization of the first clinical result can be associated with a trigger, which trigger identifies a threshold. The method can include generating a trigger result from the comparison of the first clinical result and the trigger, storing the trigger result in the patient data, identifying a navigator based on the patient data and the trigger result, and identifying a treatment protocol relevant to the patient and based on the trigger result. In some embodiments, the treatment protocol can include a workflow identifying a plurality of actions. The method can include receiving an input indicating the completion of one of the plurality of actions in the workflow and updating the patient data with information relating to the completion of one of the plurality of actions in the workflow.

In some embodiments of the method, the patient data identifies aspects of the patient's medical history. In some embodiments of the method, retrieving the first clinical result from the first data source includes determining the units of the first clinical result. In some embodiments of the method, the categorization is associated with a plurality of triggers that can have different units.

In some embodiments of the method, the method includes the trigger which has units matching the units of the first clinical result. In some embodiments of the method, the trigger result indicates if the threshold has been exceeded. In some embodiments, the method further includes providing the clinical result, the trigger result, and the patient data for the identified patient to the navigator, and in some such embodiments and in some other embodiments, the method includes providing the clinical result, the trigger result, and the patient data for the identified patient to a physician, providing the treatment protocol to the physician, and receiving an input from the physician selecting the treatment protocol.

Some embodiments of the present disclosure relate to a system for identifying a member of a healthcare organization for potential treatment. The system includes a data source configured to originate clinical results relating to aspects of patient health, memory including patient data that identifies a plurality of patients and contains aspects of the patient's medical history, and including data source information that identifies a plurality of data sources. The system can include a processor that can retrieve patient data, identify a patient from the patient data, retrieve data source information, identify a first data source from the data source information as having originated a first clinical result, and retrieve the first clinical result from the first data source. The processor can identify a categorization of the first clinical result, which categorization can be associated with a trigger that identifies a threshold. The processor can generate a trigger result from the comparison of the first clinical result and the trigger, send the trigger result to the memory for storage in the patient data, identify a navigator based on the patient data and the trigger result, and identify a treatment protocol relevant to the patient and based on the trigger result, which treatment protocol can include a workflow identifying a plurality of actions. The processor can receive an input indicating the completion of one of the plurality of actions in the workflow and update the patient data with information relating to the completion of one of the plurality of actions in the workflow.

In some embodiments of the system, retrieving of the first clinical result from the first data source can include determining the units of the first clinical result. In some embodiments of the system, the categorization is associated with a plurality of triggers having different units. In some embodiments, the processor can select the trigger having units matching the units of the first clinical result. In some embodiments, the trigger result can indicate if the threshold has been exceeded.

In some embodiments of the system, the processor can provide the clinical result, the trigger result, and the patient data for the identified patient to the navigator. In some embodiments, the processor can provide the clinical result, the trigger result, and the patient data for the identified patient to a physician, provide the treatment protocol to the physician, and receive an input from the physician selecting the treatment protocol.

Some embodiments relate to a method for admitting a member of a healthcare organization into a program. The method can include receiving data identifying a first data source that originates clinical results relating to aspects of patient health, updating data source information with information identifying the first data source, which data source information identifies a plurality of data sources that originate clinical results relating to aspects of patient health, identifying patient data associated with a member of a healthcare organization, and retrieving a first clinical result from the first data source, which first clinical result relates to the health of the member of a healthcare organization. The method can include querying a database of trigger data for a first trigger value demarking a threshold for determining whether to provide a first treatment, and determining whether the first clinical result is relevant to the first trigger value. In some embodiments, determining if the first clinical result is relevant to the first trigger value can include determining whether the format and units of the first clinical result correspond to the first trigger value. The method includes generating a first trigger result by comparing the first clinical result to the first trigger value, which first trigger result can include a first value associated with a first potential treatment or a second value that is not associated with the first potential treatment, and updating the patient data with an indicator identifying the member of a healthcare organization as a candidate for the first potential treatment.

In some embodiments of the method, the data identifying the first data source can include a request for use of clinical results from the first data source in admitting a member of a healthcare organization into the treatment program. In some embodiments, the method can include identifying the type of clinical result generated by the first data source and the format and units of the first clinical result. In some embodiments, the method can include determining if the type, format, and/or units of the clinical results generated by the first data source meet a first criteria, and in some embodiments, the data source information can be updated if the type, format, and units of the clinical results generated by the first data source meet the first criteria. In some embodiments, the method includes retrieving a second clinical result from a second data source, which second clinical result relates to the health of the member of the healthcare organization, generating a second trigger result by comparing the second clinical result to a second trigger value, which second trigger result can be a first value associated with a second potential treatment or a second value that is not associated with the second potential treatment, and updating the patient data with an indicator identifying the member of a healthcare organization as a candidate for the second potential treatment.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

FIG. 8 is a chart listing valve diseases and exemplary parameters for the characterization of those valve diseases.

FIG. 16 is a chart identifying exemplary categories for identifying the severity of vascular disease.

Figure 1:
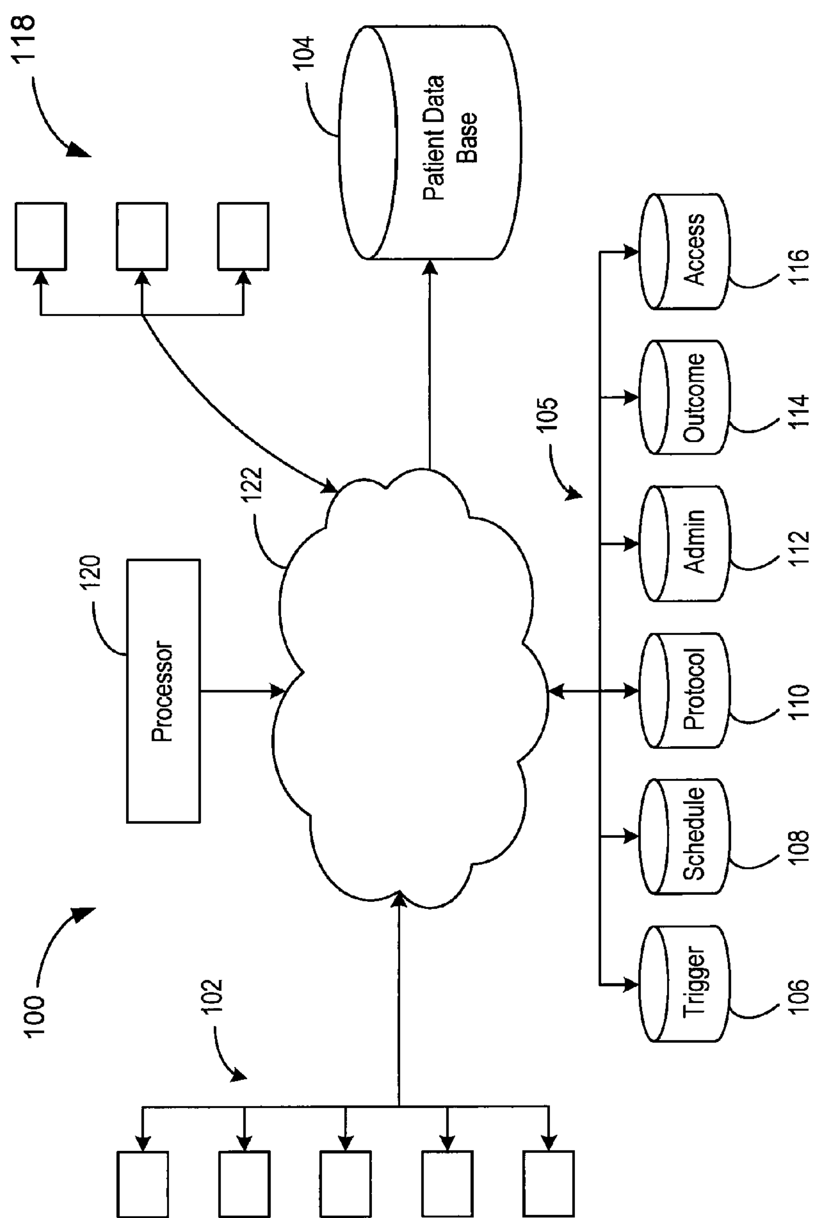
FIG. 1 is a block diagram of one embodiment of a program optimization system

In the appended figures, similar components and/or features may have the same reference label. Where the reference label is used in the specification, the description is applicable to any one of the similar components having the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION OF THE INVENTION

In one embodiment, the present disclosure provides a program optimization system. The program optimization system can include one or several patient data sources, a patient database, one or several sub databases including, for example, a trigger database, a program database, administrator database, an outcome database, and an access database, one or several user devices, and a processor. The program optimization system can mine patient information from the patient data sources and store the patient information in the patient database. The program optimization system can compare data stored in the patient database to trigger conditions stored in the trigger database to determine whether a patient can be admitted into a program. In some embodiments, for example, a program can include one or several protocols which can include treatment protocols. The protocols can be applied to a patient within a program and the program optimization system can track the completion of the protocols.

In one embodiment, the present disclosure provides a method for identifying a patient for a program. The method includes collecting patient data relating to a patient, evaluating the patient data for the existence of trigger conditions, categorizing the patient if the patient data meets the trigger conditions, and providing an indication of the categorization.

In some embodiments, the method for identifying a patient for a program can include a method for collecting patient data. The method for collecting patient data can include, for example, the process of collecting patient data from one or several patient data sources. The method for collecting patient data can specifically include generating the patient data, receiving the patient data, determining the formatting and the units of the patient data, normalizing the format and the units of the patient data to meet any standards associated with patient data, and storing the patient data.

In one embodiment, the present disclosure provides a method for identifying a patient for placement into a program. The method for identifying a patient for placement into a program can include receiving patient data, receiving trigger condition data, evaluating the patient data and the trigger condition data for relevance to each other, comparing the patient data to the trigger condition data, categorizing a patient as triggered, and determining whether additional trigger conditions are present.

In some embodiments, the method for identifying a patient for placement into a program can include a method for evaluating the received data for relevance. The method for evaluating the received data for relevance can include determining whether the trigger condition data includes a specific trigger, determining if the specific trigger is relevant to the patient, and evaluating the patient data for applicability of the specific trigger.

In one embodiment, the present disclosure provides a system for tracking a patient's progress through a program. The system for tracking a patient's progress through a program can include a processor, an output module, an input module, a communication module, and a memory. In some embodiments, for example, the memory can include a plurality of databases including a triggered patient's database, an active database, a processing database, a compliance database, a completed database, an archive database, an excluded database, and a tracking database.

In one embodiment, the present disclosure provides a method for managing a patient's progress through a program. The method can include, for example, receiving triggered patient data, identifying a triggered program, providing an indicator of a program service, receiving progress status input, and updating patient data with progress status.

In some embodiments, the method for managing a patient's progress through a program can further include steps for identifying a patient categorized in multiple programs and for optimizing services provided to maximize efficiency in progressing the patient through the programs. In some embodiments, for example, the method for managing a patient's progress through a program can include steps for prioritizing program services when a patient is placed in multiple programs. In some embodiments, for example, the method for managing a patient's progress through the program can include steps for prioritizing patients when multiple patients are included within a program. In some embodiments, the method for managing a patient's progress through a program can include steps for limiting and/or monitoring a user's access to patient information.

In one embodiment, the present disclosure provides a method for evaluating performance in progressing one or several patients through one or several programs. The method includes aggregating performance indicators, generating a performance metric, and displaying the performance metric. In some embodiments, generating the performance metric can include receiving a performance standard, comparing the performance indicators to the performance standard, generating a value indicative of the comparison of the performance indicators to the performance standard, and storing a value indicative of the results of the comparison of the performance indicators to the performance standard.

In one embodiment, the present disclosure provides a method for optimizing program outcomes. In some embodiments, the method for optimizing program outcomes includes receiving patient data, aggregating patient data, generating an indicator of patient outcomes, evaluating patient benefit based on the indicator of patient outcomes, and updating a program based on the evaluation of patient benefit.

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

Referring first to FIG. 1, a block diagram of one embodiment of a program optimization system 100 is shown. The program optimization system 100 facilitates the treatment of one or several patients by collecting and processing patient data, analyzing the patient data for trigger conditions, and admitting one or more patients into a program based on the existence of trigger conditions in the patient data. In some embodiments, the program optimization system 100 can further facilitate the treatment of one or several patients by communicating program information for one or several patients to one or several user devices. The program optimization system 100 includes one or several patient data sources 102, a patient database 104, one or several program databases 105 including, a trigger database 106, a schedule database 108, a program database 110, administrator database 112, an outcome database 114, and an access database 116. The program optimization system 100 further includes one or several user devices 118 and a processor 120. The components of the program optimization system 100 are connected by, for example, a network 122 and can thereby send and receive information.

The patient data sources 102 can be any source of data relating to a patient, a patient's history, a test performed on the patient, or any other medical data relating to the patient. The program optimization system 100 can include a plurality of patient data sources 102. In some embodiments, for example, one of the patient data sources 102 can be a medical facility such as, for example, a hospital, clinic, practice, or any other facility in which medical services are provided. One of the patient data sources 102 can be, for example, a computer terminal at which a patient or other individual enters data relating to the patient and/or the patient's medical history. In some embodiments, for example, one of the patient data sources 102 can be a test device including, for example, an echocardiogram, an MRI, an X-ray, a CT scan, an electrocardiogram, or any other medical device.

The patient data sources 102 can provide the data inputs for the program optimization system 100 that can be used to determine whether the patient is admissible into a program. These inputs can, in some embodiments, relate to a specific test received by the patient or medical data generated relating to a patient. These can include, for example, a patient's weight, height, blood pressure, cholesterol levels, platelet levels, low white blood cell counts, red blood cell counts, a biopsy result, a sonogram such as, for example, an echocardiogram, an MRI, an X-ray, a CT scan, an electrocardiogram, or any other medical data related to the patient.

The patient database 104 can include a compilation of information relating to the patient. This information can include, for example, data collected from the patient data sources 102, data input by a user, and/or data generated by the program optimization system 100. In some embodiments, for example, the data in the patient database 104 can be taken from the patient data sources 102 and converted into a standard format and/or into standard units. Thus, in some embodiments, the data stored in the patient database 104 can be normalized.

The patient data stored within the patient database 104 can be used by the program optimization system 100 to determine whether a patient is admissible into a program. In some embodiments, this determination can include, for example, the evaluation of patient data stored within the patient database 104 for the existence of one or several trigger conditions. In the event that the patient data stored in the patient database 104 includes one of the one or several trigger conditions, the patient can then be admitted into one or several programs. In some embodiments, the admission of the patient into one or several programs can be additionally stored within the patient database 104, as can the progress of the patient through the one or several programs.

The program databases 105 can comprise one or several databases that store and track information relating to a patient's admission and progress through the program and performance relating to the program and the patient's progress through the program. The program databases 105 include a trigger database 106. The trigger database 106 can store information relating to the conditions for patient admission into one or more of the programs. In some embodiments, for example, the information stored in the trigger database 106 can comprise criteria for evaluating medical data relating to the patient such as, for example, test results, medical history, or any other medical information. The information stored in the trigger database 106 can, for example, comprise information for evaluating the medical care received by the patient such as, for example, whether the patient has a primary care physician, whether the patient has a history of attending scheduled appointments and/or of taking prescribed medicines, work completing prescribed treatments, and/or the patient's insurance status.

In some embodiments, for example, information stored within the trigger database 106 can be organized into one or several trigger conditions, which can, for example, represent the complete and specific conditions for admission into a program. In some embodiments, the trigger conditions can relate to a single piece of medical data, to a single piece of information relating to the medical care received by the patient, or to a plurality and/or combination of medical data and information relating to the medical care received by the patient.

In some embodiments, the trigger conditions can comprise one or several trigger parameters. In some embodiments, the trigger parameters comprise conditions, the result of which causes the patient data to meet or fail to meet the associated trigger condition. In some embodiments, the patient data meets the trigger condition when the patient data meets one, some, or all of the trigger parameters associated with the trigger condition.

In some embodiments, the trigger parameter can comprise a logical expression. The logical expression can use the patient data as an input, and can compare the input patient data to a threshold value. If the patient data meets the threshold value, the trigger parameter can include instructions to add an indicator of the meeting of the threshold value to the patient data.

Similarly, the trigger condition can comprise a logical expression. In some embodiments, the trigger condition can use the patient data as an input, and can compare the input patient data to a threshold value. In other embodiments, the trigger condition can use the indicator associated with the one or several trigger parameters associated with the trigger condition as an input, and can compare the indicators associated with one or several trigger parameters associated with the trigger condition. If the one or several indicators, or the patient data meet the threshold value, the trigger condition can include instructions to add an indicator of the meeting of the threshold value to the patient data.

The schedule database 108 can include information relating to medical resources. In some embodiments, this information relating to medical resources can include the availability of the medical resources, and can include, for example, a facility availability, a medical service provider availability, an equipment availability, and/or the availability of any individual or thing that can provide a patient service. In some embodiments, for example, the schedule database 108 can include information relating to the availability of the doctor. This information, and or any other availability information in the schedule database 108 can be used to facilitate the creation of patient appointments and/or times to receive medical services. In some embodiments, for example, the schedule database 108 can additionally identify times of unavailability of a medical resource, and can, in the event that the unavailability is due to a scheduled appointment, indicate appointment information such as, for example, the nature of the appointment, any patient scheduled for an appointment, contact information for the patient scheduled for the appointment, payment information for the patient scheduled for the appointment, and any other patient data associated with the patient scheduled for an appointment. In some embodiments, for example, after the completion of the appointment, the schedule database 108 can receive information regarding the outcome of the appointment. This information can include, for example, whether the patient attended the appointment, the outcome of the appointment including, for example, any generated test results, medical data, or other patient data, information regarding payment for the appointment, and whether payment has been received.

In some embodiments, the information in the schedule database 108 relating to medical resource availability can include, for example, information relating to medical resources such as, an indication of the capability of the medical resource, of the nature of medical resource, the location of medical resource, and/or any other information useful in determining the suitability of the medical resource for specific purpose. In some embodiments, for example, the schedule database 108 can include information identifying a doctor's competencies and/or specialties, the location of a practice and/or medical facility, treatment and/or testing capabilities of the facility, and/or the capability of the medical resource to take on new patients.

The program database 110 includes protocols that are action items and/or steps within a program. In some embodiments, the protocols can be a list of steps and/or actions to be taken for each patient admitted into a program. These steps and/or actions can include tests that can be scheduled and performed, procedures that can be scheduled and performed, appointments that can be scheduled and performed, treatments that can be scheduled and/or administered, medications that can be administered and/or prescribed, and/or follow-up for any of the above or other steps or actions included in the protocol.

In some embodiments, the program database 110 can include one or several programs. The program can be, for example, a group of services such as treatments, tests, medications, or therapies associated with the condition and or ailment indicated by the meeting of a trigger condition. In one embodiment, the program can comprise patient follow-up that helps assure that the patient is receiving specified healthcare services associated with the conditions and/or ailments underlying the trigger condition.

In some embodiments, the program can comprise one or several protocols. The protocols can be configured to be performed serially or simultaneously. In some embodiments, the protocols can be configured to be performed in a certain order based on the relative benefit and/or risk associated with a given protocol.

In some embodiments, the program can comprise a set of static protocols, and in some embodiments, for example, the program can comprise a set of dynamic protocols. In some embodiments, the protocols can be static in that the outcomes of completed protocols do not affect the number and/or content of the remaining protocols within the program. In some embodiments, for example, the protocols can be dynamic in that the outcomes of completed protocols affect the number and/or content of the remaining protocols within the program.

In an example of one embodiment of a program comprising dynamic protocols, the program can include an initial set of protocols that can be recommended and followed when the patient is admitted into a program. Based on the results of the initial set of protocols, the program can include and/or further recommend an additional set of protocols. This additional set of protocols can include steps and/or actions to provide the patient further and/or more specific treatment based on the results of the first and/or subsequent protocols. In some such embodiments, further sets of protocols can be recommended to a patient until the patient has completed the program or has been removed from the program.

In some embodiments, for example, the program database can include information to allow the intelligent selection of protocols for application to a patient. By way of example, in some embodiments a protocol may not be applicable to a patient because of, for example, the patient's medical history, current health, or treatment location. In such embodiments, a protocol can be selected for use with the patient and/or can be administered based on some detail of the patient data such as, for example, the location of the patient, the patient's status such as designation as an inpatient or as an outpatient, the age of the patient, the location of the treatment provided to the patient, the severity of the ailment and/or deficiency resulting in the patient being admitted into the program, and/or any other desired information relating to the patient. Thus, the program protocol can include steps or actions tailored to the patient and/or the patient's needs.

The administrator database 112 can include data tracking certain aspects of a patient's progress through a program and/or admission into a program. This data can include, for example, data relating to the timing of the services provided to the patient such as, for example, the amount of time passed between when a patient is admitted into the program and when the program is completed and/or when the patient is removed from the program, the amount of time passed between when a patient is admitted into the program and when the first step towards completing a protocol is taken, the amount of time used to complete a protocol, and/or any other similar data. In some embodiments, for example, this data can relate to a single patient, a single user, a group of patients, a group of users, some or all the patients or users associated with the program, some or all of the patients or users associated with a specific facility, or any other desired individual or group. In some embodiments, the data included in the administrator database 112 can be used in tracking and managing the promptness and effectiveness of medical assets and resources.

The outcome database 114 can include data for evaluating program outcomes. In some embodiments, for example, the data for evaluating program outcomes can be patient specific, protocol specific, user specific, facility specific, and/or program specific. In some embodiments, for example, the data tracking program outcomes can include information relating to the effectiveness of the program in treating the underlying patient problem and/or ailment, the patient satisfaction with the program, the costs associated with the program, information relating to payment received for services provided in the program, or any other desired information. The data stored within the outcome database 114 can, in some embodiments, be used to evaluate the effectiveness of the program as a function of patient outcome, as a function of cost-benefit analysis, or as a function of any other effectiveness metric. This information can then be used to tailor the program and/or the program protocols to increase the effectiveness of the program in treating the underlying patient condition and/or ailment resulting in a patient admission to a program.

The access database 116 can include security information for the program optimization system 100. This information can include user information such as, for example, a username and password, the user access level, a program access level, or any other desired security feature. In some embodiments, for example, the access database 116 can include information relating to data accessed by a user. The information stored within the access database 116 can be used to prevent unauthorized individuals from accessing the program optimization system 100 and/or information stored within the program optimization system. The information stored within the access database 116 can be used to track and identify the user and/or individual who has access to and/or accesses patient data. The information stored within the access database 116 can also be used to restrict the amount and type of data that can be accessed by the user. In some embodiments, for example, these restrictions can be related to the user's job, the user's location, the patient associated with the user, the program associated with the user, a program protocol that has been completed by user, or a patient request.

The user devices 118 can include any device used to access the program optimization system 100. The user devices 118 can include any device capable of storing and analyzing data and providing information to and receiving instructions and information from a user. The user devices 118 can be, for example, a computing device such as a computer, a desktop computer, a laptop, a tablet, a smart phone, or any other similar device.

The user devices 118 can include, for example, an administrator device that can be, for example, used to access the program optimization system 100 to manage the program optimization system 100 and/or to evaluate the effectiveness of the program optimization system 100 and/or of the users, a provider device that can be, for example, used to access the program optimization system 100 to receive information relating to a patient, to a program and/or programs into which a patient has been admitted, and/or to provide information relating to a patient's progress within a program, and/or a nurse navigator device that can, for example, be used to access the program optimization system 100 to facilitate the management of a patient's progress through a program. The user devices 118, and specifically the nurse navigator will be discussed at greater detail below.

The processor 120 can provide instructions to and receive information from the other components of the program optimization system 100. The processor 120 can act according to stored instructions. The processor 120 can comprise a microprocessor, such as a microprocessor from Intel® or Advanced Micro Devices, Inc.®, or the like.

The network 122 allows communication between the components of the program optimization system 100. The network 122 can be, for example, a local area network (LAN), a wide area network (WAN), a wired network, wireless network, a telephone network such as, for example, a cellphone network, the Internet, the World Wide Web, or any other desired network. In some embodiments, the network can use any desired communication and/or network protocols.

Figure 2:
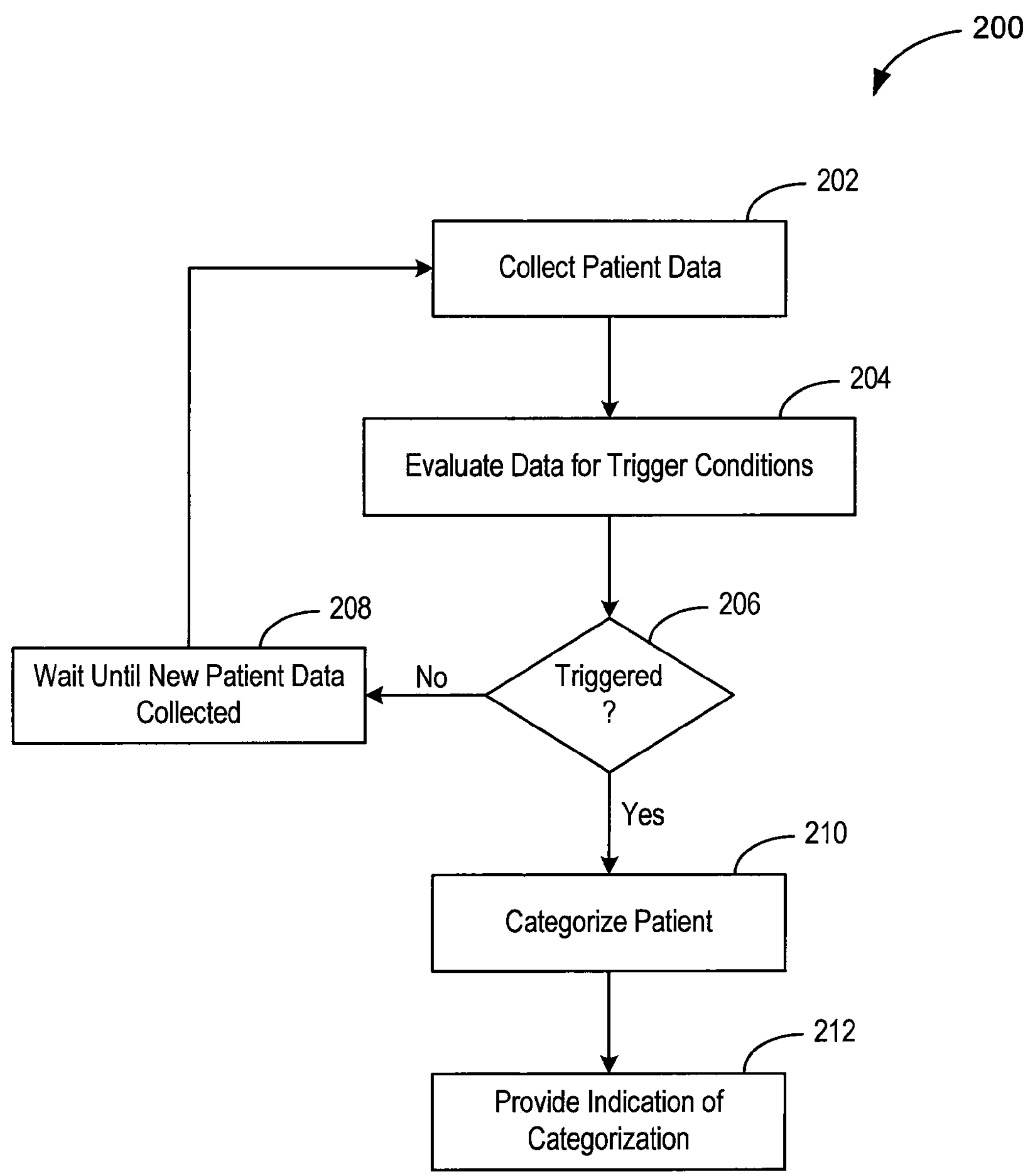
FIG. 2 is a flowchart illustrating one embodiment of a process for admitting patient into a program.

With reference now to FIG. 2, a flowchart of a process 200 for admitting a patient into a program is shown. The process 200 can be performed by the program optimization system 100 and/or by components of the program optimization system 100.

The process begins at block 202 wherein patient data is collected. In some embodiments, for example, the patient data can be collected from one or several patient data sources 102. In some embodiments, and as discussed above, the patient data sources 102 can comprise a medical facility, a computer terminal, or a medical device. In some embodiments, the patient data source can be memory or database connected to or located in any of the above-mentioned types of patient data sources 102. Thus, in some embodiments, collecting patient data can include communicating with the patient data sources 102 to query the patient data sources 102 for patient data and communicating with the patient data sources 102 in order to receive patient data.

After the patient data has been collected, the process 200 proceeds to block 204 wherein the patient data is evaluated for trigger conditions. In some embodiments, for example, the evaluation of the patient data for trigger conditions can include identifying conditions matching admission conditions for a program. The evaluation of the patient data for the existence of one or several trigger conditions can be performed by the processor 120 of the program optimization system 100.

The evaluation of the patient data for the existence of one or several trigger conditions can be initiated in a variety of ways. In some embodiments, for example, the evaluation of the patient data for the existence of one or several trigger conditions can be initiated by a user request for such an evaluation. In some embodiments, the evaluation of the patient data for the existence of one or several trigger conditions can be performed in response to the occurrence of a triggering event such as, for example, the receipt of new patient data, or the passing of a specified time interval.

After the patient data is evaluated for the existence of one or several trigger conditions, the process 200 proceeds to decision state 206 wherein it is determined whether the trigger conditions have been met by the patient data. If the conditions have not been met or triggered, then the process 200 proceeds to block 208 and waits until new patient data is collected, at which point the process 200 returns to block 202 wherein patient data is collected.

Returning to decision state 206, if the conditions have been met or triggered, the process 200 proceeds to block 210 wherein the patient is categorized. In some embodiments, for example, the categorization of the patient corresponds to admitting the patient into a program. In some embodiments, a patient may be admitted into a single program, and in some embodiments a patient may be admitted into multiple programs.

After the patient has been categorized, the process 200 proceeds to block 212 wherein an indication of the categorization is provided. In some embodiments, for example, the indication of the categorization can be provided in the patient database 104, and can be associated with a specific patient. In some embodiments, and as discussed above, a patient can be admitted into a single program or into multiple programs. As a result of this, in some embodiments, a single indicator of the categorization may be associated with patient and in some embodiments, multiple indicators of the categorization may be associated with patient. Thus, in some embodiments, the indication of the categorization can be associated with the patient, can be stored in the patient database 104, and can indicate into which programs the patient has been admitted.

Figure 3:
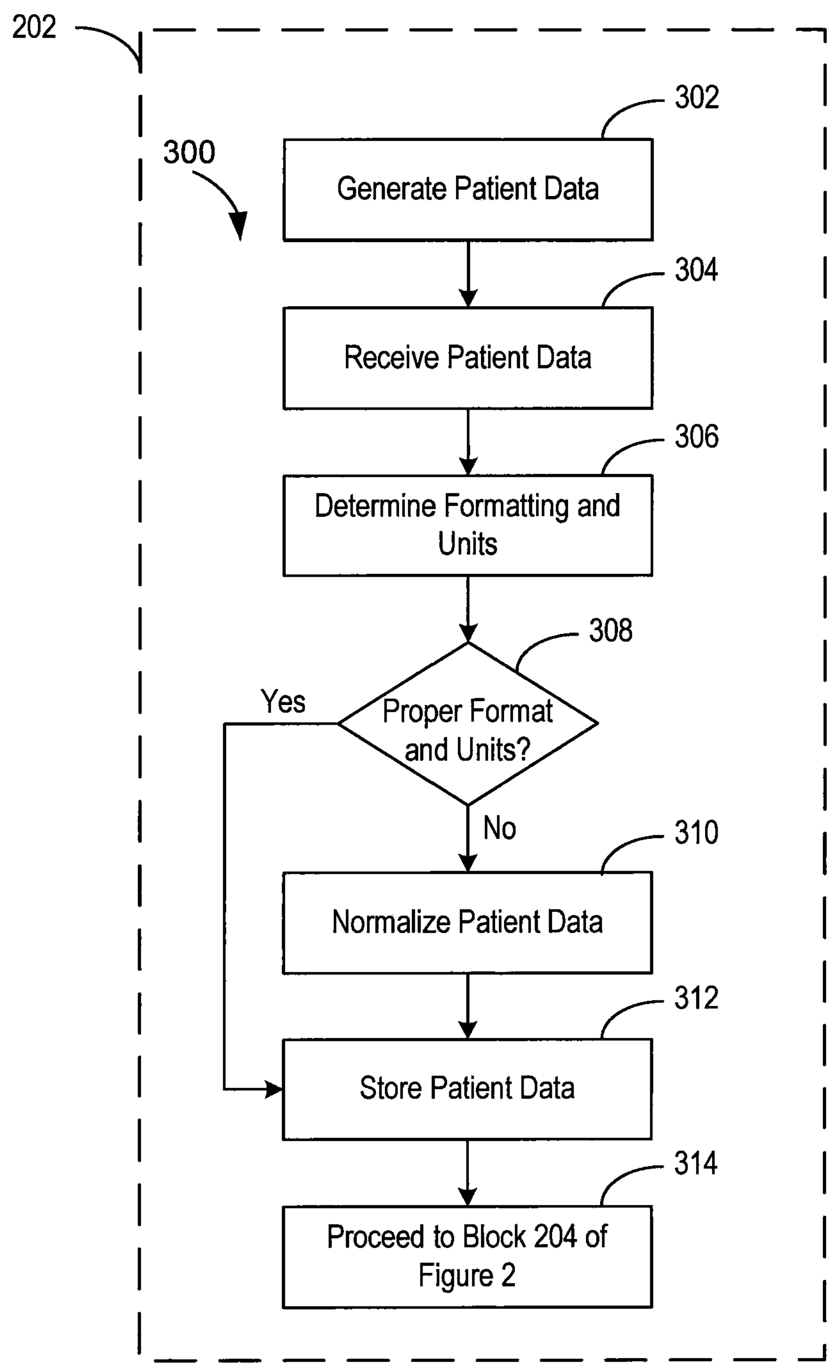
FIG. 3 is a flowchart illustrating one embodiment of a process for collecting patient data.

With reference now to FIG. 3, a flowchart of a process 300 for collecting patient data is shown. As indicated in FIG. 3, the process 300 can be performed in the place of block 202 as indicated in FIG. 2. The process 300 for collecting patient data can include the process of gathering patient data from one or several patient data sources 102, preparing that patient data for use by the program optimization system 100 in determining whether patients are admissible into a program, and storing the patient data.

The process 300 begins at block 302 wherein patient data is generated. As discussed above the patient data is generated at one or several of the patient data sources 102. The patient data can be generated by, for example, patient input, by input of a medical service provider such as, for example, a doctor or a nurse, by input of an insurance provider, or by a medical device and/or testing device. In some embodiments, the patient data can relate to a characteristic of the patient such as name, age, contact information, identification information, smoking habits, eating habits, drinking habits, sexual habits, risk indicators, medicine and/or drug use, gender, height, weight, cholesterol level, body mass index, blood composition, platelet count, white blood cell counts, red blood cell count, insurance status, association with a primary care physician or other medical service provider, such as, for example, a specialist such as a cardiologist, or any other characteristic of the patient. In some specific embodiments, the patient data can include the results of a test such as, for example, an electrocardiogram, an echocardiogram, a sonogram, an MRI, an X-ray, a CT scan, a blood test, a colonoscopy, or any other procedure that generates or gathers medical data relating to the patient. In some embodiments, the patient data can be generated from non-digital records. In some embodiments, information can be retrieved from non-digital records and converted to digital form by one of the patient data sources 102, and/or can be retrieved from non-digital records and converted to digital form by another component of the program optimization system 100 such as, for example, the processor 120. The converted information from the non-digital records can be stored in the patient database 104.

In some embodiments, patient data generated at block 302 may be stored in a database or memory located in, or associated with patient data sources 102. In some embodiments, for example, the database can be stored in an office and/or facility computer or server, or in an online repository associated with an office and/or facility, and in some embodiments, for example, the database can be stored in memory associated with a medical device or piece of medical equipment.

After the patient data is generated, the process 300 proceeds to block 304 wherein the patient data is received. In some embodiments, the patient data can be received by the processor 120, and can be received as a result of a process that determines whether new patient data is available. In some embodiments, for example, the process for determining whether new patient data is available can be performed by the processor 120, and in some embodiments, the process for determining whether new patient data is available can be performed by the patient data sources 102.

In one embodiment in which the process for determining whether the patient data is available is performed by the processor 120, the processor 120 can query one or several of the patient data sources 102 for patient data. This query can be prompted by a variety of circumstances, such as, for example by a user command, by the passage of an amount of time, or any other desired trigger. In response to the query for patient data, the patient data source 102 can provide a signal indicating whether the patient data source 102 has new patient data. If the patient data source 102 has new patient data, then the processor 120 can request the patient data and the patient data can be provided to the processor 120.

In some embodiments in which the process for determining whether the patient data is available is performed by the patient data source 102, the patient data source 102 can be configured to provide an indicator of new patient data when the patient data source 102 receives new patient data. This indicator of new patient data can be provided to the processor 120. In response receiving the indicator that new patient data is available, the processor 120 can request the patient data and can receive the patient data. Alternatively, in some embodiments, the indicator that new patient data is available can be accompanied by the new patient data.

After the patient data has been received, the process 300 proceeds to block 306 wherein the formatting and units of the patient data are determined. In some embodiments, the patient data from the patient data source 102 may include formatting and/or units that are different from the formatting and/or units used by other components of the program optimization system 100. In such an embodiment it can be advantageous to normalize the patient data to include the same formatting and/or units used by the other components of the program optimization system 100.

After the formatting units of the patient data are determined the process 300 can proceed to decision state 308 wherein it is determined whether or not the formatting and/or units of the patient data are proper. In some embodiments, for example, the patient database 104 can include information relating to formatting and/or units used by other components of the program optimization system 100. In some embodiments a block 306, the processor 120 can query, for example, the patient data source 102 for information relating to formatting and/or units used by the components of the program optimization system 100. Upon receiving this information, the processor 120 can compare the formatting and/or unit standards of the program optimization system 100 with the formatting and/or units associated with patient data received from the patient data source 102.

In the event that the patient data does not include the proper formatting and/or units, the process 300 can proceed to block 310 wherein the patient data is normalized. In some embodiments, for example, the normalization of the patient data can include converting the format of the patient data to match the format standards of the program optimization system 100. In some embodiments, for example, the normalization of the patient data can include converting the units used in the patient data to match the unit standards of the program optimization system 100. In some embodiments, the normalization of the patient data can include identifying a discrepancy between the patient data and the formatting and/or unit standards of the program optimization system 100, and converting the formatting and/or units of the patient data to match the standards of the program optimization system 100.

After the patient data has been normalized, or in the event that it is determined at decision state 308 that the patient data has the proper formatting and/or units, the process proceeds to block 312 wherein the patient data is stored. In some embodiments, for example, the patient data is stored in the patient database 104. After the patient data has been stored, the process 300 proceeds to block 314 and proceeds to block 204 of FIG. 2.

Figure 4:
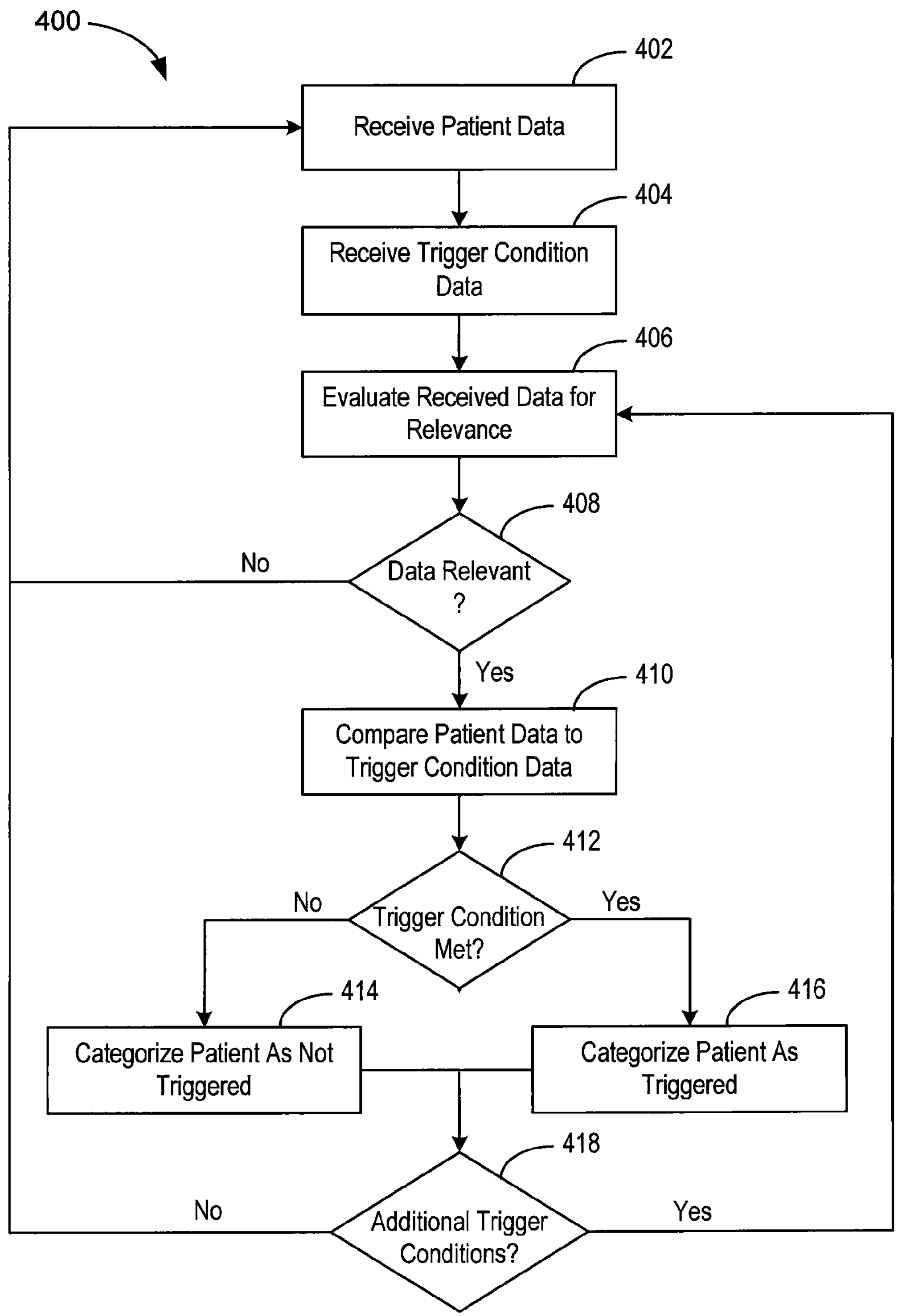
FIG. 4 is a flowchart illustrating one embodiment of a process for determining if a trigger condition exists in patient data.

With reference now to FIG. 4, a flowchart of a process 400 for determining if a trigger condition exists in patient data is shown. The process 400 begins at block 402 wherein the patient data is received. The patient data can be received from the patient database 104. In some embodiments, the patient data can be received in response to request for the patient data by the processor 120, and in some embodiments, the patient data can be received from the patient database 104 in response to an event such as, for example, the passage of a certain amount of time or the receipt of new patient data by the patient database 104.

After the patient data has been received the process 400 proceeds to block 404 wherein the trigger condition data is received. The trigger condition data can include data identifying a trigger condition that can give rise to a patient's admission into a program. The trigger condition data can be received from the trigger database 106. In some embodiments, the trigger data can be received from the trigger database 106 in response to a request for the trigger data by the processor 120.

The trigger date condition data can include one or several trigger conditions. The trigger condition can be any condition that allows distinguishing between a patient admissible into a program and a patient that is not admissible into a program. In some embodiments, the trigger condition can allow evaluation of all or a portion of the patient data to determine whether a patient is admissible into a program. In some embodiments, the trigger condition can allow the evaluation of a portion of the patient data to determine whether the patient is admissible into a program such as, for example, one or several test results, one or several parameters relating to the patient, one or several parameters relating to a patient's insurance status and/or care status.

The trigger condition can be based on any factors useful in evaluating a patient's need for admission into a program or need for care. In some embodiments, the trigger condition can be generated based on symptoms of one or several ailments and/or conditions associated with the program, on diagnosing procedures, or on risk indicators.

In some embodiments, for example, the trigger condition can, as discussed above, comprise one or several trigger parameters. The trigger parameter can, like the trigger condition, be based on any factors useful in evaluating a patient's need for admission into a program and/or need for care, and like the trigger condition, the trigger parameter can be used to analyze patient data in the determination of whether a patient can be admitted into a program.

In some embodiments, the trigger condition can be a default trigger condition, and in some embodiments, for example, the trigger condition can be a specific trigger condition. In some embodiments, for example, a specific trigger condition may be useful in circumstances in which a medical facility and/or medical practitioner does not have access to all the equipment used to evaluate a patient for admission into a program based on a default trigger condition, for evaluation purposes, or in a circumstance in which medical facility or medical practitioner prefers the specific trigger condition.

After the trigger condition data has been received, the process 400 proceeds to block 406 wherein the received data is evaluated for relevance. In some embodiments, for example, the received patient data and the received trigger condition data are evaluated by the processor 120 for their relevance to each other. Specifically, in some embodiments the patient data is evaluated to determine if it includes data applicable to the trigger condition data, and in some embodiments, for example, the patient data is evaluated to determine whether the patient data includes the proper formats and/or units for use with the trigger condition data. Similarly, in some embodiments the trigger condition data is evaluated for its applicability to the patient and/or the patient data. The evaluation of the patient data and that trigger condition data will be discussed in greater detail below.

After the received data is evaluated for relevance, the process 400 proceeds to decision state 408 wherein it is determined whether received data is relevant. If the received data is not relevant, then the process returns to block 402. If the received data is relevant, the process 400 proceeds to block 410 wherein the patient data is compared to the trigger condition data. In some embodiments, the comparison of the patient data to the trigger condition data can include the determination of whether the trigger condition is met in the patient data.

After the patient data is compared to the trigger condition data, the process 400 proceeds to decision state 412 wherein it is determined if the trigger condition is met. If the trigger condition is not met, the process proceeds to block 414 wherein the patient is categorized as not triggered. In some embodiments, for example, the patient can be categorized as not triggered by providing an indicator of the non-triggered status of the patient in the patient database 104.

Returning again to decision state 412, if it is determined the trigger condition is met, the process 400 proceeds to block 416 wherein the patient is categorized as triggered. In some embodiments, for example, the patient can be categorized as triggered by providing an indicator of the triggered status of the patient in the patient database 104.

After the patient is categorized as either triggered or not triggered, the process 400 proceeds to decision state 418 wherein it is determined whether the trigger condition data includes additional trigger conditions. In the event that the trigger condition data does not include additional trigger conditions, then the process 400 returns to block 402 and receives patient data. In the event that the trigger condition data does include additional trigger conditions, then the process 400 returns to block 406.

Figure 5:
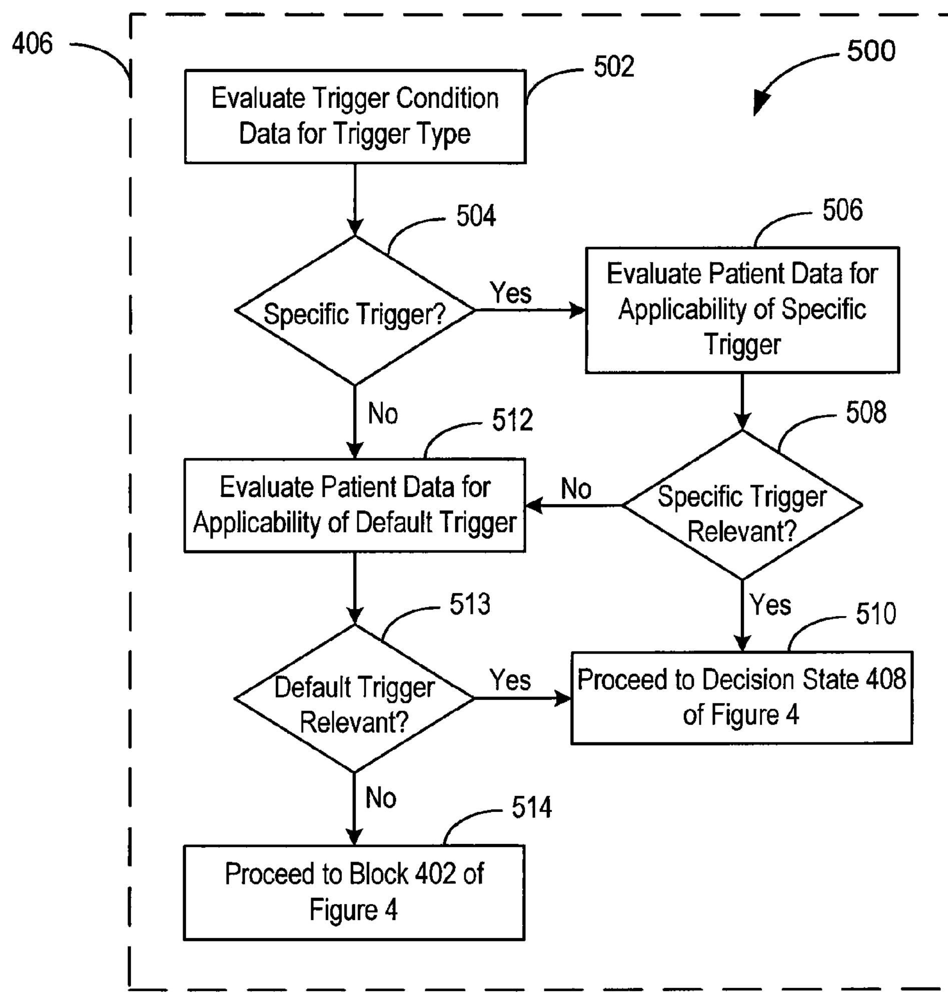
FIG. 5 is a flowchart illustrating one embodiment of a process for evaluating received data for relevance.

With reference now to FIG. 5, a flowchart depicting a process 500 for evaluating the received data for relevance is shown. The process 500 begins at block 502 wherein the trigger condition data is evaluated for the trigger type. In some embodiments, for example, the evaluation of the trigger condition data for the trigger type can include providing the trigger condition data with an indicator of whether the trigger condition data represents a specific trigger or a default trigger. In some embodiments, the evaluation of the trigger condition data can be performed by, for example, the processor 120. After the trigger condition data is valued in for trigger type, the process 500 proceeds to decision state 504 wherein it is determined if the trigger condition data is a specific trigger.

If the trigger condition data is a specific trigger, then the process 500 proceeds to block 506 wherein the patient data is evaluated for the applicability of the specific trigger. In some embodiments, the evaluation the patient data for the applicability of the specific trigger can include evaluating the patient data to determine whether the patient data includes all of the information, data, and formatting used in the application of the specific trigger. In some embodiments, for example, this evaluation can include determining whether the specific trigger is relevant to the patient data. Thus, for example, in some embodiments in which the specific trigger relates to a program that is unrelated to information contained within the patient data, the specific trigger may be inapplicable to the received patient data.

After the patient data is evaluated for the applicability to the specific trigger, the process 500 proceeds to decision state 508 wherein it is determined if the specific trigger is relevant. The determination of the relevance of the specific trigger can be performed by the processor 120 and can be based on the results of the evaluation of the applicability of the patient data to the specific trigger performed in block 506. If the specific trigger is relevant to the patient data, the process 500 proceeds to block 510 and proceeds to decision state 408 of FIG. 4.

Returning again to decision state 504, if it is determined the trigger condition data is not a specific trigger, then the process 500 proceeds to block 512 and evaluates the patient data for applicability to the default trigger. In some embodiments, the evaluation the patient data for the applicability to the default trigger can include evaluating the patient data to determine whether the patient data includes all of the information, data, units, and formatting used in the application of the default trigger. In some embodiments, for example, this evaluation can include determining whether that default trigger is relevant to the patient data. Thus, for example, in some embodiments in which the default trigger relates to a program that is unrelated to information contained within the patient data, the default trigger may be inapplicable to the receipt of patient data.

After the patient data is evaluated for the applicability of the default trigger, the process 500 proceeds to decision state 513 wherein it is determined if the default trigger is relevant. The determination of the relevance of the default trigger can be performed by the processor 120 and can be based on the results of the evaluation of the applicability of the patient data to the default trigger performed in block 512. If the default trigger is not relevant to the patient data, the process 500 proceeds to block 514 and then proceeds to block 402 of FIG. 4. If the default trigger is relevant to the patient data, the process 500 proceeds to block 510 and proceeds to block 408 of FIG. 4.

Figure 6:
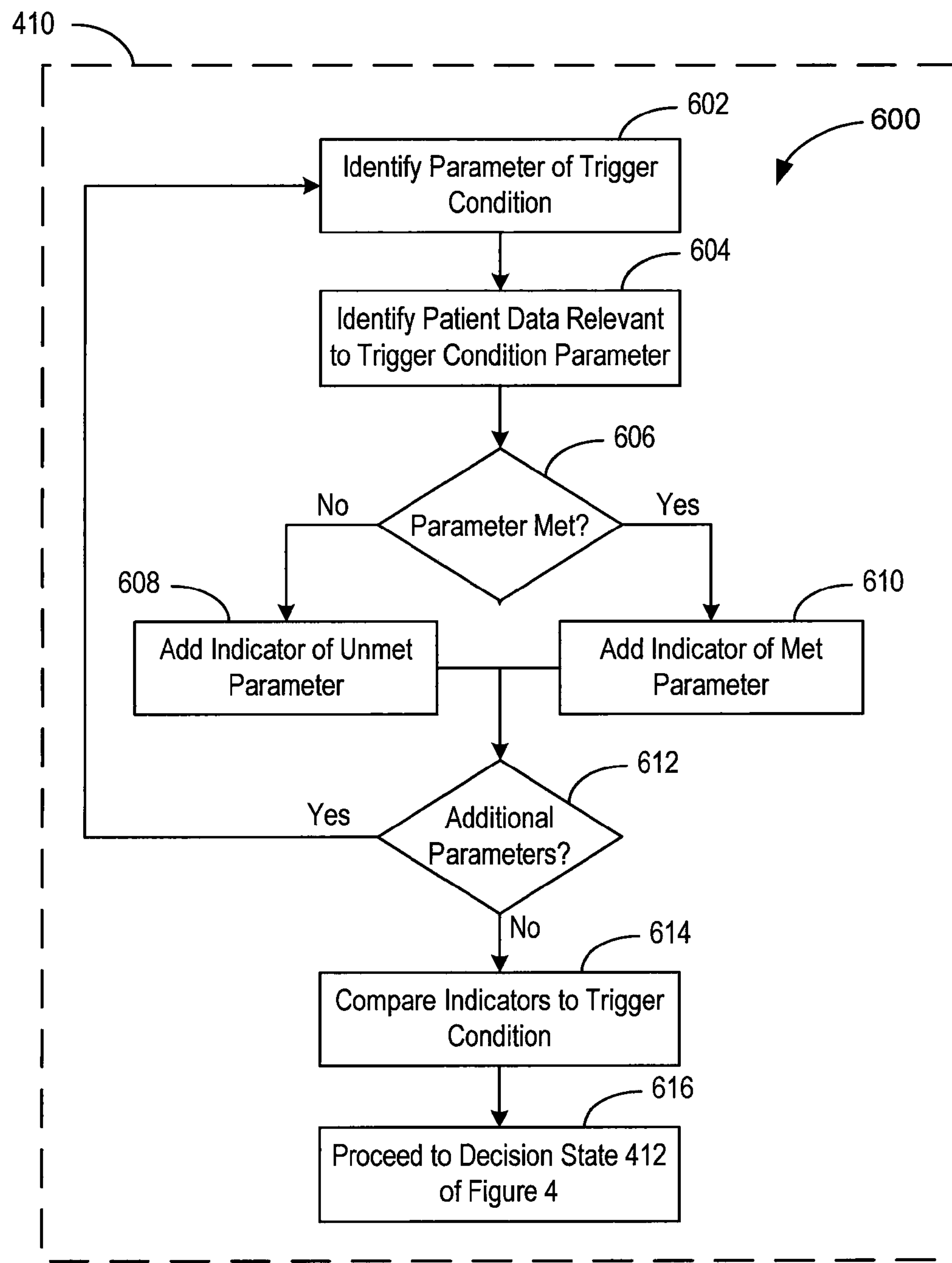
FIG. 6 is a flowchart illustrating one embodiment of a process for comparing patient data to trigger condition data.

With reference now to FIG. 6, a process 600 for comparing patient data to trigger condition data is shown. As indicated by the dotted line labeled 410 around the process 600, the process 600 can be performed in the place of block 410 in FIG. 4.

The process 600 begins in block 602 wherein a parameter of the trigger condition is identified. As discussed above, the trigger condition can include one or several parameters. The parameters of the trigger condition can include criteria that can be used, in aggregate, to determine whether the trigger condition is met and whether a patient is admissible into a program.

After the parameter of the trigger condition has been identified, the process 600 proceeds to block 604 wherein the patient data relevant to the trigger condition parameter is identified. In some of embodiments, the identification of patient data relevant to the trigger condition parameter can include identifying the type of data and/or the portion of the patient data applicable to the trigger condition parameter. Thus, for example, in embodiments in which the trigger condition parameter relates to electrocardiogram data, the identification of patient data relevant to the trigger condition parameter can include the identification and selection of electrocardiogram data from the patient data.

After the patient data relevant to the trigger condition parameter has been identified, the process 600 proceeds to decision state 606 wherein it is determined if the trigger condition parameter is met. In some embodiments, this determination can be made by the processor 120.

If the trigger condition parameter is not met, then the process 600 proceeds to block 608 and an indicator of the unmet parameter is added. In some embodiments, for example, the indicator of the unmet parameter can be added to the patient data and can, for example, be stored in the patient database 104. Returning again to decision state 606, if it is determined that the trigger condition parameter is met, then the process proceeds to block 610 wherein an indicator of the met parameter is added. In some embodiments, for example, the indicator of the met parameter can be added to the patient data and can, for example, be stored in the patient database 104.

After the indicator has been added, the process 600 proceeds to decision state 612 wherein it is determined if there are additional parameters associated with the trigger condition. In some embodiments, for example, this determination can be made by the processor 120 by evaluating the trigger condition data. If the trigger condition data includes additional parameters, then the process proceeds to block 602.

If the trigger condition data does not include additional parameters, then the process proceeds to block 614 wherein the one or several added indicators are compared to the trigger condition. In some embodiments, the comparison of one or several added indicators to the trigger condition can be performed by the processor 120, and can include determining whether or not the added indicators identify a patient as admissible to a program. After the one or several indicators are compared to the trigger condition, the process 600 proceeds to block 616 wherein the process proceeds to decision state 412 of FIG. 4.

Figure 7:
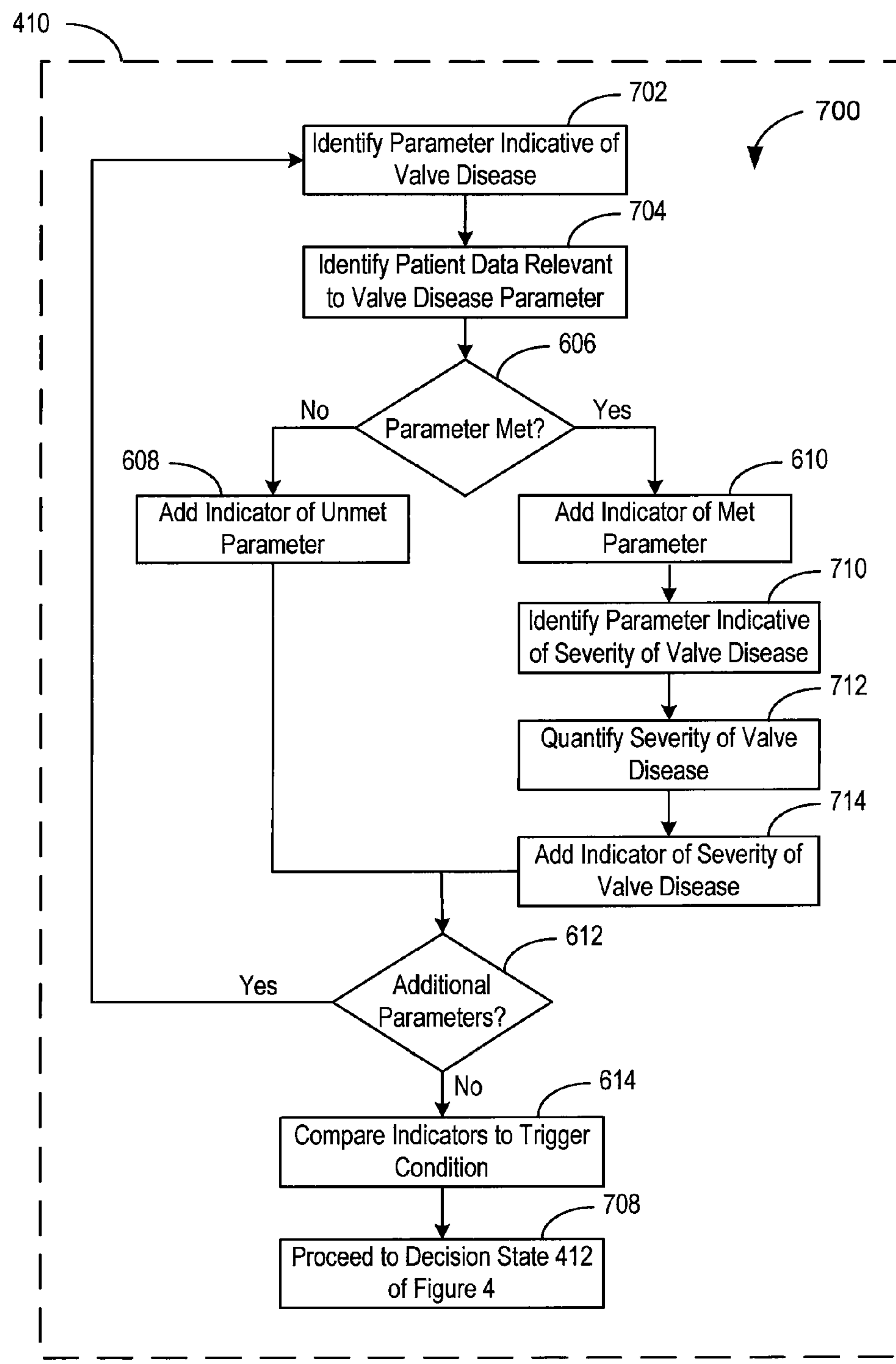
FIG. 7 is a flowchart illustrating one embodiment of a process for comparing patient data to trigger condition data for valve disease.

With reference now to FIG. 7, the process 700 for comparing patient data to trigger condition data for valve disease is shown. As indicated by the dotted line labeled 410 around the process 700, the process 700 can be performed as part of block 410 of FIG. 4.

The process 700 begins in block 702 wherein a parameter of the trigger condition indicative of valve disease is identified. As discussed above, the trigger condition can include one or several parameters. The parameters of the trigger condition can include criteria that can be used alone or in aggregate to determine whether the trigger condition is met, and whether patient is admissible into a program relating to valve disease.

After the parameter indicative of valve disease has been identified, the process 700 proceeds to block 704 wherein the patient data relevant to the parameter indicative of valve disease is identified. In some embodiments, the identification of patient data relevant to the trigger condition parameter of valve disease can include identifying the type of data and/or the portion of the patient data applicable to the trigger condition parameter. Thus, for example, patient data including information providing an indicator of potential valve disease can be identified.

After the patient data relevant to the trigger condition parameter has been identified, the process 700 proceeds to decision state 606 wherein it is determined if the trigger condition parameter is met. Further details relating to decision state 606 can be found described above.

If the trigger condition parameter is not met, then the process 700 proceeds to block 608 wherein an indicator of the unmet parameter is added. If the trigger condition parameter is met, then the process 700 proceeds to block 610 wherein an indicator of the met parameter is added. Further details relating to blocks 608 and 610 can be found described above.

Returning again to block 608 after the indicator of the unmet parameter has been added, the process 700 proceeds to decision state 612, wherein it is determined if trigger condition includes additional parameters. Further details relating to decision state 612 can be found described above. If the trigger condition includes additional parameters, the process 700 returns to block 702.

If the trigger condition does not include additional parameters, then the process 700 proceeds to block 614 wherein the one or several added indicators are compared to the trigger condition. This comparison can be used to determine whether patient is admissible into the program relating to valve disease. Greater details about block 614 can be found described above. After the indicators are compared to the trigger condition, the process 700 proceeds to block 708 wherein the process 700 proceeds to decision state 412 of FIG. 4.

Returning again to block 610, after indicator of the met parameter has been added, the process 700 proceeds to block 710 wherein parameter indicative of the severity of valve disease is identified. In some embodiments, for example, a determination of the severity of an ailment such as, for example, the severity of valve disease can be useful in prioritizing a patient and/or program for treatment and/or for determining a program and/or treatment applicable to the patient. In some embodiments, for example, a parameter indicative of the severity of an ailment or condition associated with the program can be stored in, for example, the trigger database 106. Like the trigger condition, the parameter indicative of the severity of the ailment can relate to patient data and can be used in comparison with patient data to determine the severity of the patient ailment.

In some embodiments, the parameter indicative of the severity of an ailment such as, for example, valve disease can be received simultaneous with the trigger condition data. In some embodiments, the parameter indicative of the severity of an ailment such as, for example, valve disease can be received separate from the trigger condition data. In such an embodiment, processor 120 can request parameter indicative of the severity of the ailment after determining that a parameter has been met.

After the parameter indicative of the severity of valve disease been identified, the process 700 proceeds to block 712 wherein the severity of the valve disease is quantified. In some embodiments, for example, the severity of the valve disease can be quantified by comparing the patient data relevant to the parameter indicative of valve disease to the parameter indicative of the severity of the valve disease. The severity of an ailment, such as of valve disease, can be quantified in a variety of fashions. In some embodiments, for example, the quantification of the severity of the valve disease can be relatively quantified so as to allow the prioritization of patients within a program relative to other patients. In some embodiments, for example, the quantification of the severity of an ailment such as valve disease can include placing a patient admitted into the program relating to valve disease into a group. In one such exemplary embodiment, the quantification of the severity of valve disease can include, for example, dividing patients admissible to the program into one of four groups, each of which groups corresponds to a defined severity of an ailment such as of valve disease.

After the severity of valve disease has been quantified, the process 700 proceeds to block 714 wherein an indicator of the severity of valve disease or other ailment is added. In some embodiments, for example, the indicator of the severity of valve disease can be added to the patient data and can, for example, be stored in the patient database 104.

After the indicator of the severity of valve disease has been added, the process 700 proceeds to decision state 612 wherein it is determined if there are additional parameters associated with the trigger condition. If additional parameters are associated with the trigger condition, then the process 700 returns to block 702. If no additional parameters are associated with the trigger condition, then the process 700 proceeds to block 614 wherein the indicators are compared to the trigger condition, and wherein it is determined if the patient is admissible into a program. After the indicators are compared to the trigger condition, the process 700 proceeds to block 708 wherein the process 700 proceeds to decision state 412 of FIG. 4.

With reference now to FIG. 8, an exemplary chart 800 listing valve diseases and parameters for the characterization of those valve diseases is depicted. In some embodiments, for example, these parameters can be measured in an echocardiogram or other test. As seen in chart 800 patients can be admitted into programs for a variety of valve diseases including, for example, mitral regurgitation, mitral stenosis, and/or aortic stenosis. As further seen in chart 800, a variety of different parameters can be used for admitting a patient into a program for valve disease. In some embodiments, for example, a patient may admitted into the valve disease program if they have met the trigger condition for each of the parameters of valve disease, and in other embodiments, for example, a patient may be admitted into the valve disease program if they have met the trigger condition for one or more of the parameters of valve disease.

As also seen in chart 800, the parameters for the characterization of valve disease can be divided according to the severity of the condition indicated by different measured performance levels. Specifically, chart 800 device parameters for the characterization of valve disease into the categories of mild, moderate, and severe. In some embodiments, for example, the trigger condition for admission into the valve disease program can correspond to any desired threshold level including, for example, a mild condition, a moderate condition, and/or severe condition.

Figure 9:
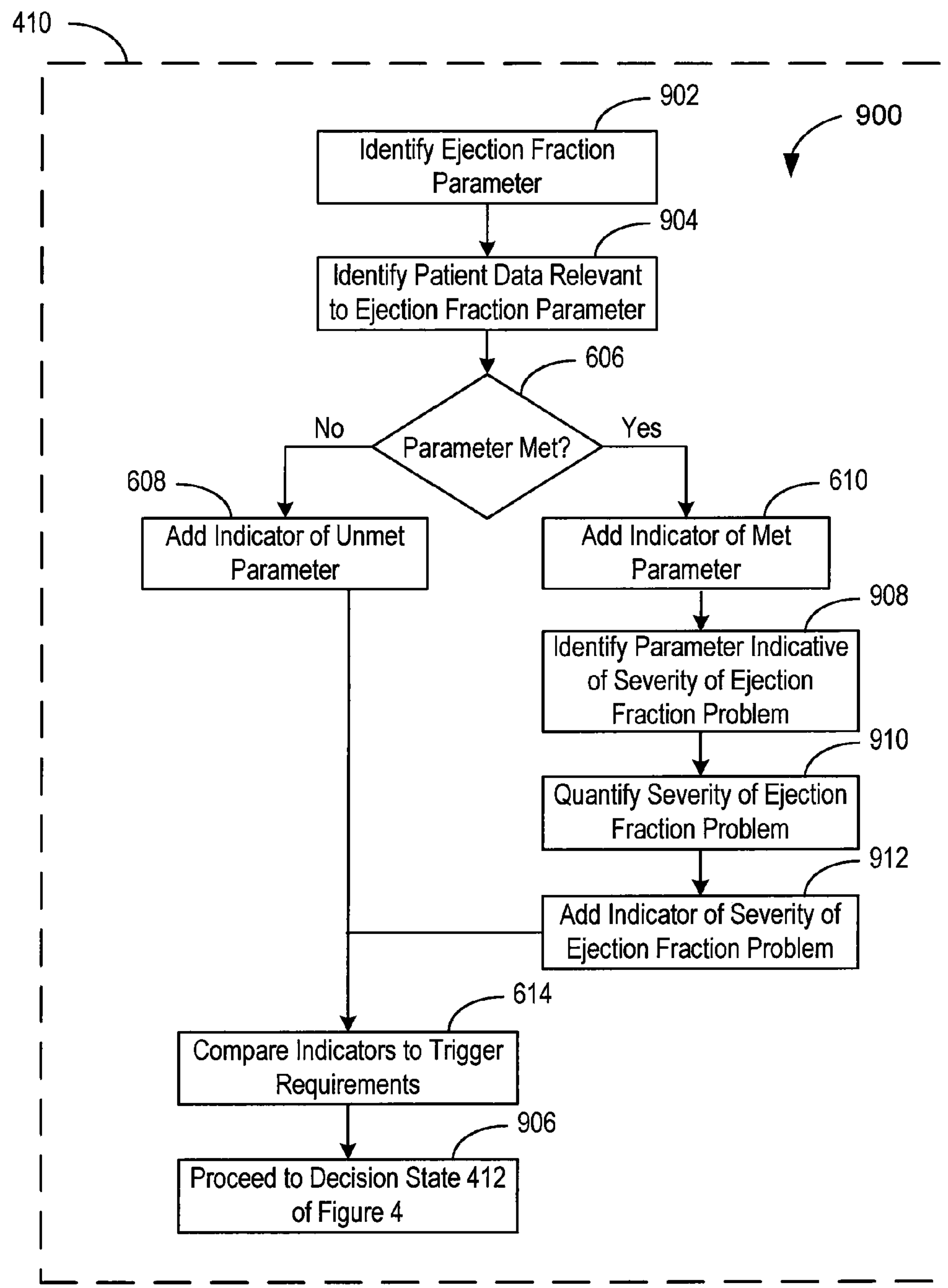
FIG. 9 is a flowchart illustrating one embodiment of a process for comparing patient data to trigger condition data for ejection fraction.

With reference now to FIG. 9, the process 900 for comparing patient data to trigger condition data for ejection fraction is shown. As indicated by the dotted line labeled 410 around the process 900, the process 900 can be performed as part of block 410 of FIG. 4.

The process 900 begins in block 902 wherein a parameter of the trigger condition indicative of an inadequate ejection fraction, the volumetric fraction of blood pumped out of the ventricle (heart) with each heart beat or cardiac cycle, is identified. As discussed above, the trigger condition can include one or several parameters, and the parameters of the trigger condition can include criteria that can be used common aggregate, to determine whether the trigger condition is met, and whether patient is admissible into a program relating to ejection fraction.

After the parameter indicative of inadequate ejection fraction has been identified, the process 900 proceeds to block 904 wherein the patient data relevant to the parameter indicative of inadequate ejection fraction is identified. In some embodiments, the identification of patient data relevant to the trigger condition parameter of inadequate ejection fraction can include identifying the type of data and/or the portion of the patient data applicable to the trigger condition parameter. Thus, for example, patient data including information providing an indicator of potential inadequate ejection fraction can be identified.

After the patient data relevant to the trigger condition parameter has been identified, the process 900 proceeds to decision state 606 wherein it is determined if the trigger condition parameter is met. Greater details relating to decision state 606 can be found described above.

If the trigger condition parameter is not met, then the process 900 proceeds to block 608 wherein an indicator of the unmet parameter is added. If the trigger condition parameter is met, then the process 900 proceeds to block 610 wherein an indicator of the met parameter is added. Further details relating to blocks 608 and 610 can be found described above.

Returning again to block 608 after the indicator of the unmet parameter has been added, the process 900 proceeds to block 614 wherein the one or several added indicators are compared to the trigger condition. This comparison can be used to determine whether patient is admissible into the program relating to inadequate ejection fraction. Greater details about block 614 can be found described above. After the indicators are compared to the trigger condition, the process 900 proceeds to block 906 wherein the process 900 further proceeds to decision state 412 of FIG. 4.

Returning again to block 610, after indicator of the met parameter has been added, the process 900 proceeds to block 908 wherein parameter indicative of the severity of ejection fraction problem is identified.

After the parameter indicative of the severity of the ejection fraction problem has been identified, the process 900 proceeds to block 910 wherein the severity of the ejection fraction problem is quantified. In some embodiments, for example, the patient data relevant to the parameter indicative of the ejection fraction problem can be compared to the parameter indicative of the severity of the ejection fraction problem to quantify the severity of ejection fraction problem. The severity of the ejection fraction problem can be quantified as discussed above.

After the severity of the ejection fraction problem has been quantified, the process 900 proceeds to block 912, wherein an indicator of the severity of the ejection fraction problem or other ailment is added. In some embodiments, for example, the indicator of the severity of ejection fraction problem can be added to the patient data and can, for example, be stored in the patient database 104.

After an indicator of the severity of the ejection fraction problem has been added, the process 900 proceeds to block 614 wherein the indicators are compared to the trigger condition, and wherein it is determined whether patient is admissible into the program. After the indicators are compared to the trigger condition, the process 900 proceeds to block 906 wherein the process 900 proceeds to decision state 412 of FIG. 4.

Figure 10:
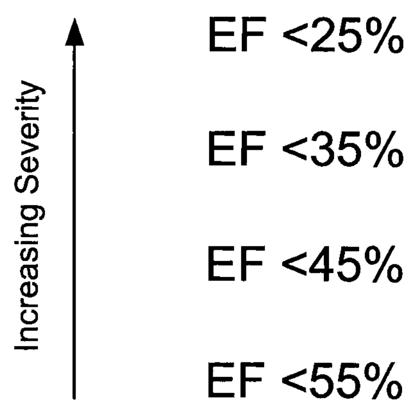
FIG. 10 is a chart listing exemplary parameters for the characterization of ejection fraction problems.

With reference now to FIG. 10, an exemplary chart 1000 listing parameters for the characterization of ejection fraction problems is shown. In some embodiments, for example, these parameters can be measured in an echocardiogram or other test. As seen in chart 1000 patients can be admitted into programs for example, when they have an ejection fraction less than a desired value such as, for example, 25%, 35%, 45%, or 55%. In some embodiments, for example, the parameters for the characterization of ejection fraction problems can be divided according to the severity of the condition. Thus, for example, a patient exhibiting an ejection fraction of 25% may have a problem that is more severe than a patient exhibiting an ejection fraction of 35% or 45%. Thus, the ejection fraction exhibited by the patient can be used to quantify the severity of the patient's ejection fraction problem. While chart 1000 lists specific values for characterization of ejection fraction problems, any other or intermediate value can be used for this characterization.

Figure 11:
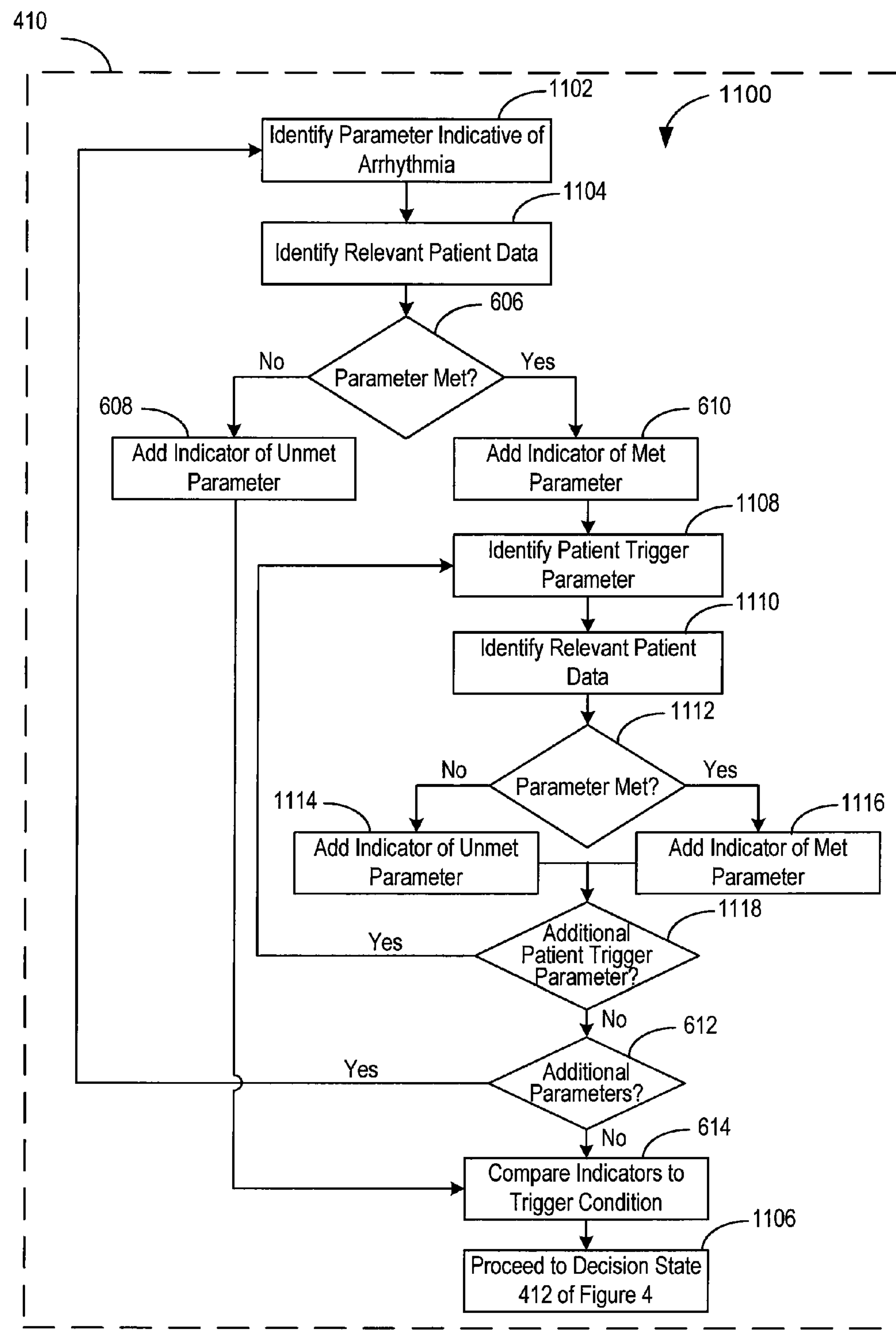
FIG. 11 is a flowchart illustrating one embodiment of a process for comparing patient data to trigger condition data for arrhythmia.

With reference now to FIG. 11, the process 1100 for comparing patient data to trigger condition data for arrhythmia is shown. As indicated by the dotted line labeled 410 around the process 1100, the process 1100 can be performed as part of block 410 of FIG. 4.

The process 1100 begins in block 1102 wherein a parameter of the trigger condition indicative of arrhythmia, an irregular heartbeat, is identified. As discussed above, the trigger condition can include one or several parameters. The parameters of the trigger condition can include criteria that can be used alone or in aggregate, to determine whether the trigger condition is met, and whether the patient is admissible into the arrhythmia program.

After the parameter indicative of arrhythmia has been identified, the process 1100 proceeds to block 1104 wherein the patient data relevant to the parameter indicative of arrhythmia is identified. In some embodiments, the identification of patient data relevant to the trigger condition parameter for arrhythmia can include identifying the type of data and/or the portion of the patient data applicable to the trigger condition parameter. Thus, for example, patient data including information providing an indicator of potential arrhythmia can be identified.

After the patient data relevant to the trigger condition parameter has been identified, the process 1100 proceeds to decision state 606 wherein it is determined if the trigger condition parameter is met. Greater details relating to decision state 606 can be found described above.

If the trigger condition parameter is not met, then the process 1100 proceeds to block 608 wherein an indicator of the unmet parameter is added. If the trigger condition parameter is met, then the process 1100 proceeds to block 610 wherein an indicator of the met parameter is added. Further details relating to blocks 608 and 610 can be found described above.

Returning again to block 608 after the indicator of the unmet parameter has been added, the process 1100 proceeds to block 614 wherein the one or several added indicators are compared to the trigger condition. This comparison can be used to determine whether the patient is admissible into the program for arrhythmia. Greater details about block 614 can be found described above. After the indicators are compared to the trigger condition, the process 1100 proceeds to block 1106 wherein the process 1100 further proceeds to decision state 412 of FIG. 4.

Returning again to block 610, after indicator of the met parameter has been added, the process 1100 proceeds to block 1108 wherein the patient trigger parameter is identified. In some embodiments, for example, the patient trigger parameter can relate to an aspect of the patient such as, for example, the age of the patient, or treatments received by the patient in some embodiments, the patient trigger parameter can be retrieved from, for example, the trigger database 106. In some embodiments, the process 1100 may not include a patient trigger parameter, in which case, the process 1100 proceeds to decision state 612.

After the patient trigger parameter has been received from the processor 120, the process 1100 proceeds to block 1110 wherein relevant patient data is identified. In some embodiments, relevant patient data can be identified in the same manner discussed above with respect to block 1104.

After the relevant patient has been identified, the process 1100 proceeds to decision state 1112 wherein it is determined if the parameter is met. If the parameter is not met, the process 1100 proceeds to block 1114 wherein an indicator of the unmet parameter is added. Returning to decision state 1112, if the parameter is met, the process 1100 proceeds to block 1116 wherein an indicator of the met parameter is added. The details of the function of the decision state 1112 and of blocks 1114, 1116 can be found above with respect to the discussion of decision state 606 and blocks 608, 610.

After the indicator has been added, the process 1100 proceeds to decision state 1118 wherein it is determined if there is an additional patient trigger parameter. This determination can be made by the processor 120 based on the evaluation of the trigger condition data. If it is determined that there is an additional patient trigger parameter, the process 1100 can return to block 1108. If it is determined that there is not an additional patient trigger parameter, then the process 1100 proceeds to decision state 612, wherein it is determined if there are additional parameters associated with the trigger condition. If additional parameters are associated with the trigger condition, then the process 1100 returns to block 1102. If there are no additional parameters associated with the trigger condition, then the process 1100 proceeds to block 614 wherein the indicators are compared to the trigger condition, and wherein it is determined whether the patient is admissible into the arrhythmia program. After the indicators are compared to the trigger condition, the process 1100 proceeds to block 1106 wherein the process 1100 proceeds to decision state 412 of FIG. 4.

Figure 12:
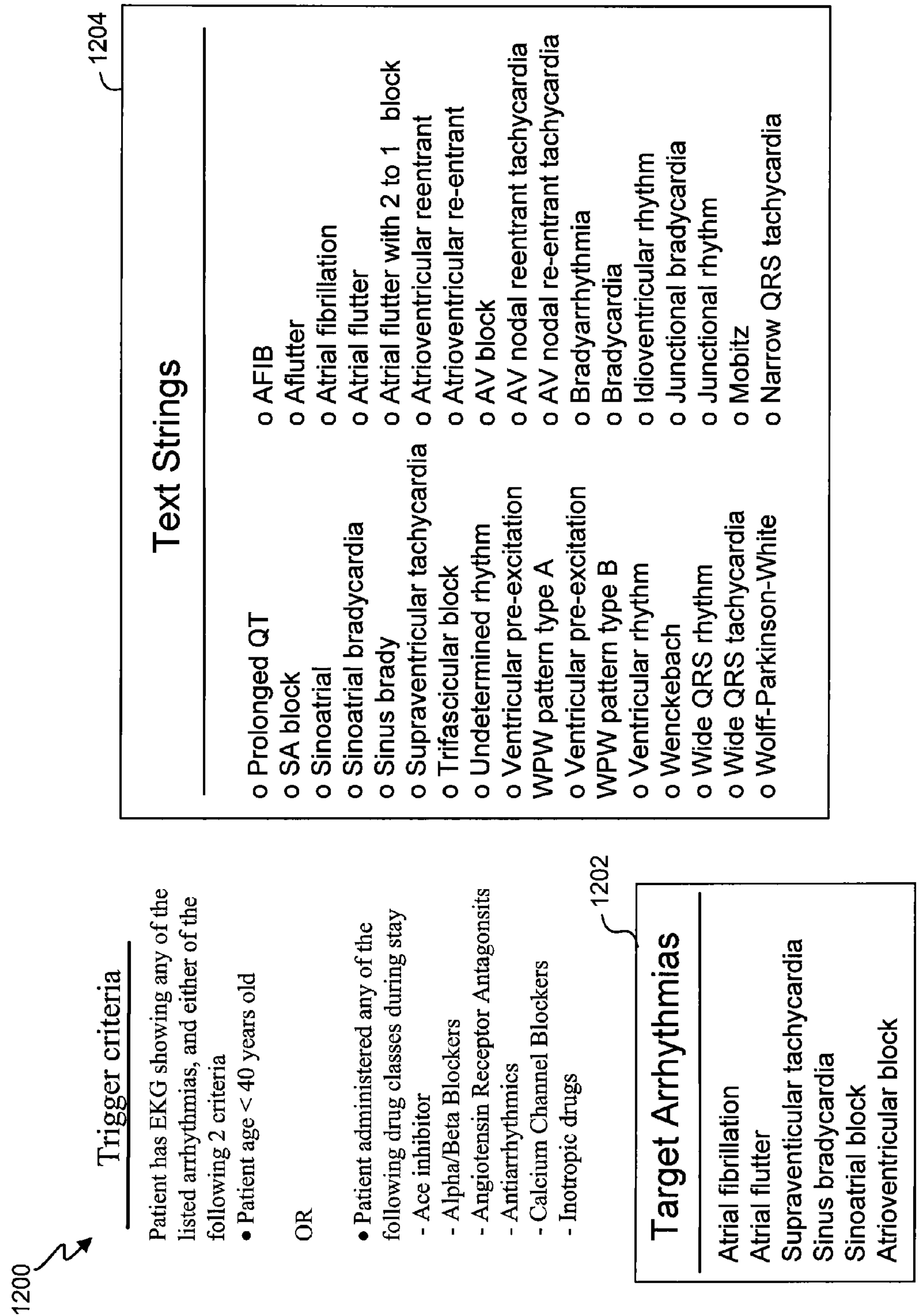
FIG. 12 is a chart listing exemplary parameters for the characterization of arrhythmia.

With reference now to FIG. 12, an exemplary chart 1200 listing parameters for the characterization of arrhythmia is shown. In some embodiments, for example, these parameters can be measured in an electrocardiogram or other test. As seen in chart 1200, patients can be admitted into programs, for example, when they have an electrocardiogram showing any of the exemplary arrhythmias shown in block 1202, and when they are either a patient over a certain age such as, for example, 30 years, 40 years, 50 years, 60 years, 70 years, or any other or intermediate age, when the patient has been administered any of the following drug classes during a recent treatment including, for example, an ace inhibitor, alpha/beta blockers, angiotensin receptor antagonists, antiarrhythmics, calcium channel blockers, or inotropic drugs. In some embodiments, for example, the severity of the arrhythmia can be determined based on the type of exhibit arrhythmia or the magnitude of the exhibit arrhythmia. Block 1204 additionally lists several exemplary text strings associated with the exemplary arrhythmias. In some embodiments, one or several of the text strings can be retrieved from the patient data and or retrieved from non-digital records that can be, for example, stored in one or several of the patient data sources 102. In some embodiments, text strings in addition to those listed in FIG. 12 can be associated with one or several arrhythmias. Exemplary text strings of these additional text strings can include, for example, Atrial fibrillation.

Figure 13:
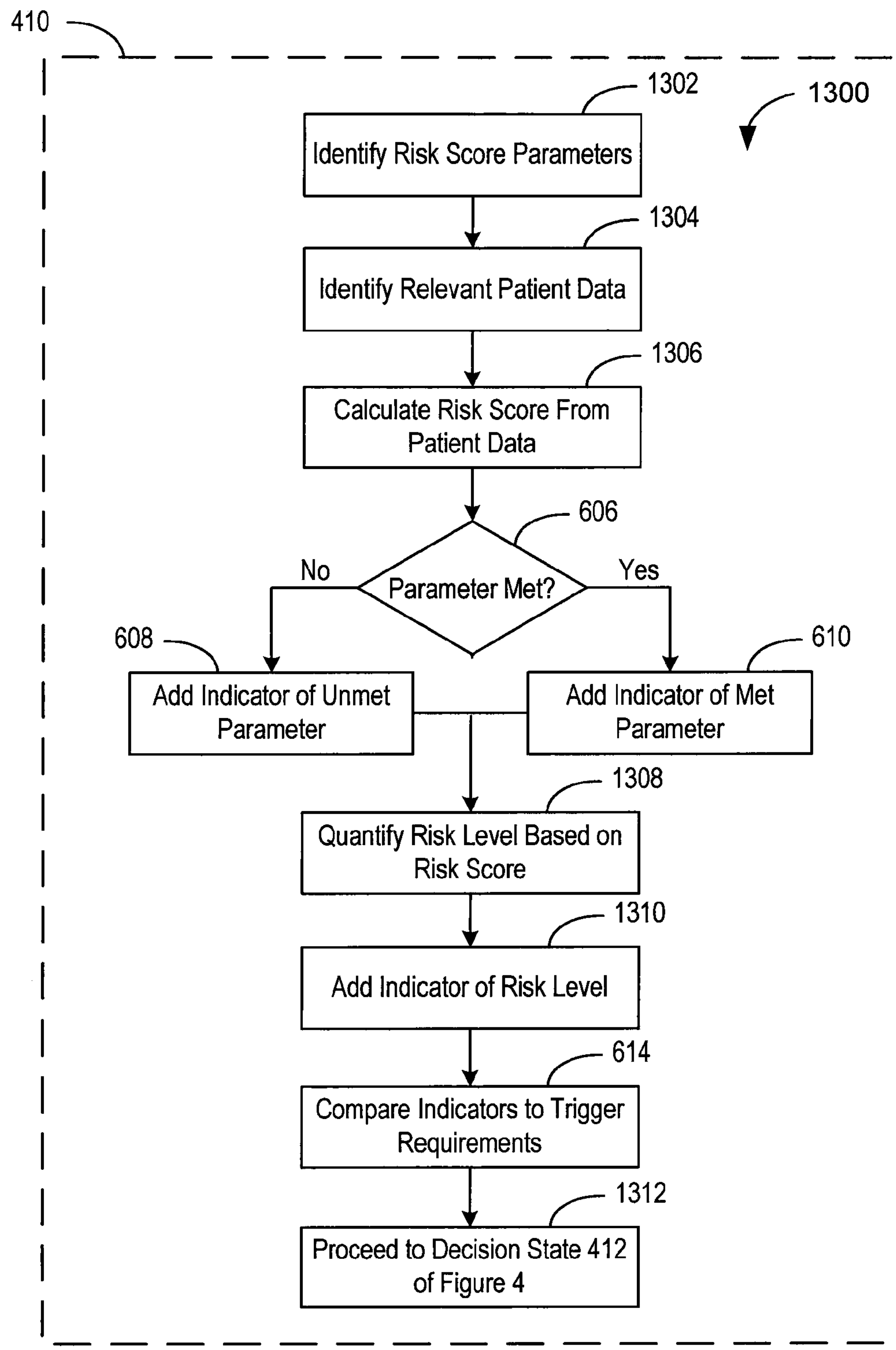
FIG. 13 is a flowchart illustrating one embodiment of a process for comparing patient data to trigger condition data for risk score parameters.

With reference now to FIG. 13, the process 1300 for comparing patient data to trigger condition data for risk score parameters is shown. As indicated by the dotted line labeled 410 around the process 1300, the process 1300 can be performed as part of block 410 of FIG. 4.

The process 1300 begins in block 1302 wherein the risk score parameters are identified. As discussed above, the trigger condition can include one or several parameters. The parameters of the trigger condition can include criteria that can be used alone or in aggregate, to determine whether the trigger condition is met, and whether patient is admissible into a program relating to ejection fraction.

After the risk score parameters have been identified, the process 1300 proceeds to block 1304 wherein the patient data relevant to the risk score parameters is identified. In some embodiments, the identification patient data relevant to the trigger condition parameter can include identifying the type of data and/or the portion of the patient data applicable to the trigger condition parameter.

After the patient data relevant to the trigger condition parameter has been identified, the process 1300 proceeds to block 1306 wherein the one or several risk scores are calculated from the patient data. In some embodiments, the one or several risk scores can be related to a general risk and/or a specific risk. In some embodiments, for example, the one or several risk scores can be related to a specific ailment, such as, for example, a cardiac risk score, a vascular risk score, a cancer risk score, a respiratory risk score, a diabetes risk score, or any other desired risk score. In some embodiments, the risk score can correspond to a Framingham score and/or a modified Framingham score. The risk score can be calculated by the processor 120. In some embodiments, the risk score can be calculated using patient data corresponding to one or several characteristics used in risk score calculation. In some embodiments, the patient data corresponding to the one or several characteristics used in the risk score calculation can be identified. In some embodiments, the patient data can then be converted to the desired form for use in the risk score calculation. In some embodiments, for example, the identified patient data can be converted to the desired form. The identified patient data can then be entered into a risk score algorithm that can calculate a risk score based on the input patient data. In some embodiments, for example, the algorithm can give each patient data input a weight, and the weighted input patient data can be collected into a risk score. In some embodiments, the input patient data can be multiplied by a weighting factor, and the weighted inputs can then be added together to form a risk score. In some embodiments, for example, if one or several of the inputs is missing, the risk score calculation can assign a risk neutral value for the missing input and then calculate a risk score. In some embodiments, the risk score calculation can eliminate the missing input from the calculation and calculate the risk score based on the received inputs. In some embodiments, for example, in which a Framingham score is calculated, this calculation can be performed based on known techniques and relations.

After the risk scores have been calculated, the process 1300 proceeds to decision state 606 wherein it is determined if the trigger condition parameter is met. Greater details relating to decision state 606 can be found described above.

If the trigger condition parameter is not met, then the process 1300 proceeds to block 608 wherein an indicator of the unmet parameter is added. If the trigger condition parameter is met, then the process 1300 proceeds to block 610 wherein an indicator of the met parameter is added. Further details relating to blocks 608 and 610 can be found described above.

Returning again to block 608 after the indicator of the unmet parameter has been added, and returning to block 610 after the indicator of the met parameter has been added, the process 1300 proceeds to block 1308 wherein the patient risk level is quantified based on the risk score. In some embodiments, for example, the patient's risk level can be quantified based on the risk score by comparing the calculated risk score generated from the patient data in block 1306 with the risk score parameters. In some embodiments, for example, the risk level can increase with the increase in the magnitude of the extent to which the calculated risk score exceeds the risk score parameters.

After the risk level based on the risk scores are quantified, the process 1300 proceeds to block 1310 wherein an indicator of the risk level is added. In some embodiments, for example, the indicator of the risk level can be added to the patient database 104.

After indicator of the risk level has been added, the process 1300 proceeds to block 614 wherein the indicators are compared to the trigger condition, and wherein it is determined whether patient is admissible into the program. After the indicators are compared to the trigger condition, the process 1300 proceeds to block 1312 wherein the process 1300 proceeds to decision state 412 of FIG. 4.

Figure 14:
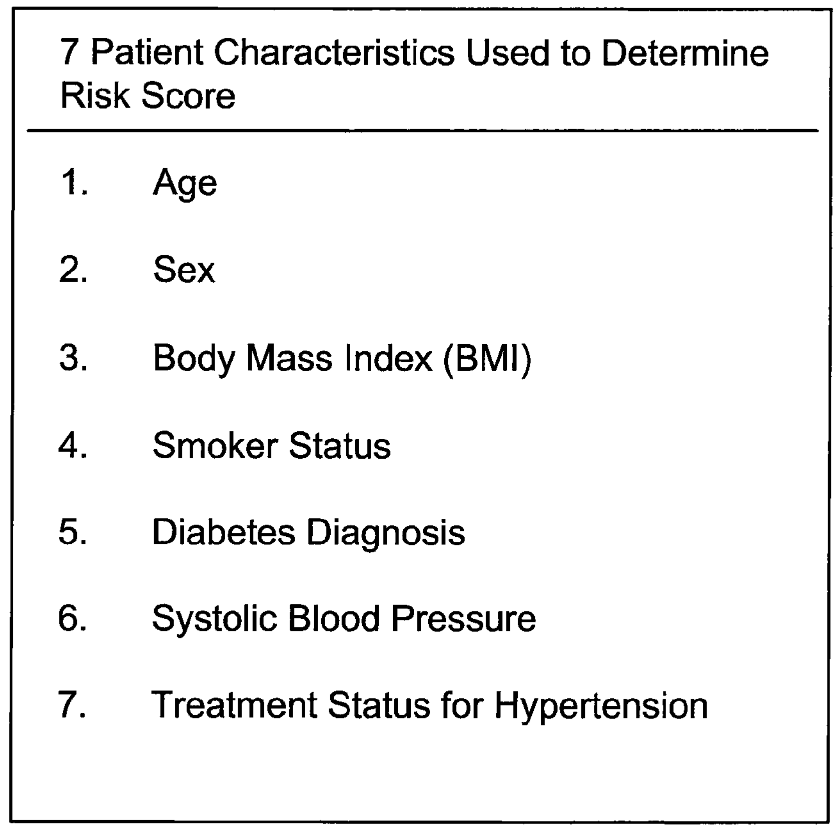
FIG. 14 is a chart listing exemplary factors for calculating a risk score.

With reference now to FIG. 14, an exemplary chart 1400 listing factors for calculating a risk score is shown. In some embodiments, seven patient characteristics can be used to determine the risk score. In some embodiments, more or fewer factors than those listed in chart 1400 can be used in the determination and/or calculation of a risk score. These characteristics include, for example, age, sex, body mass index, smoker status, diabetes diagnosis, systolic blood pressure, and treatment status for hypertension. In some embodiments, for example, different factors can be used to calculate and/or determine the risk score.

Figure 15:
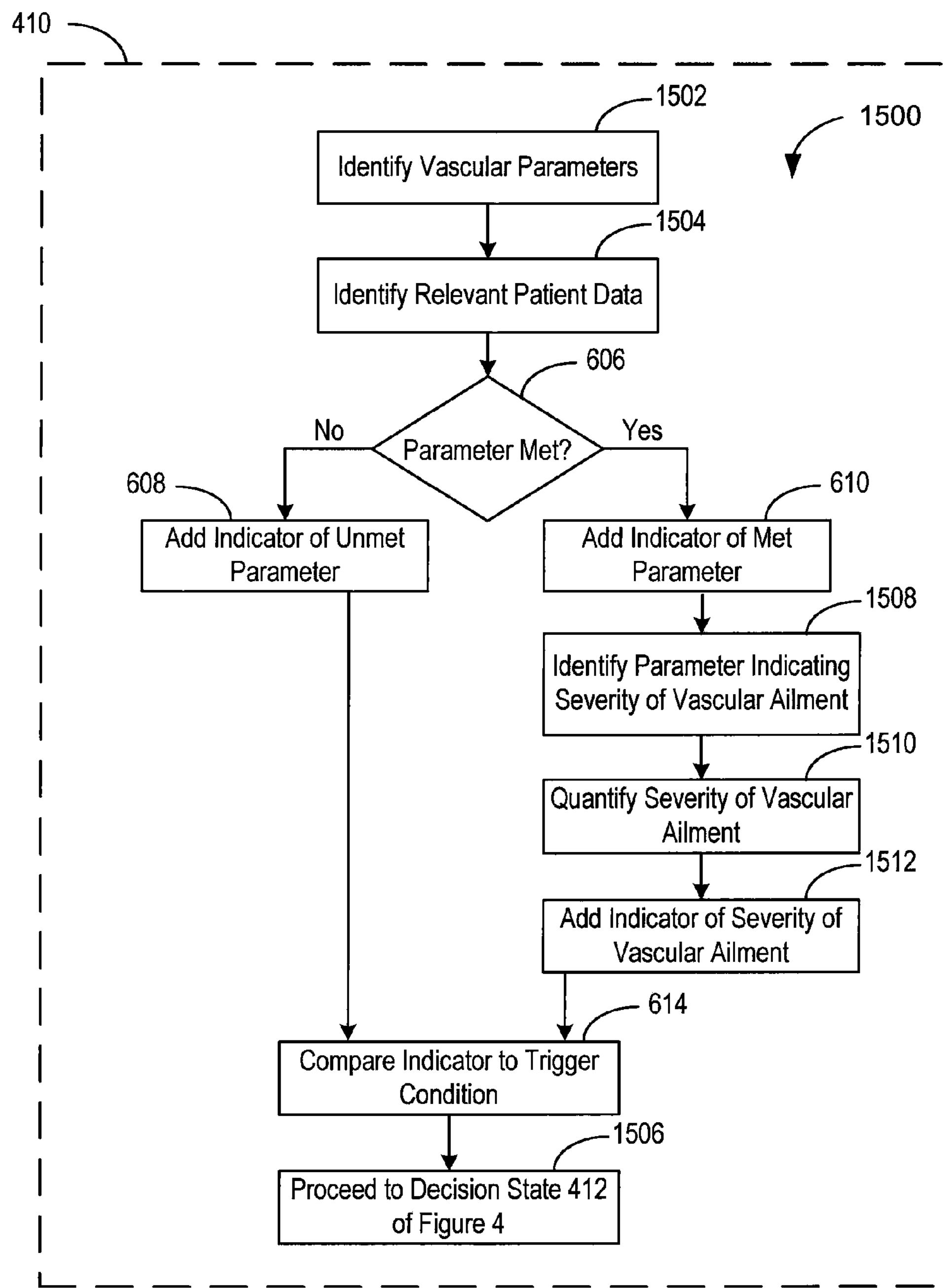
FIG. 15 is a flowchart illustrating one embodiment of a process for comparing patient data to trigger condition data for vascular disease.

With reference now to FIG. 15, the process 1500 for comparing patient data to trigger condition data for vascular disease is shown. As indicated by the dotted line labeled 410 around the process 1500, the process 1500 can be performed as part of block 410 of FIG. 4.

The process 1500 begins in block 1502 wherein a parameter of the trigger condition for vascular disease is identified. As discussed above, the trigger condition can include one or several parameters. The parameters of the trigger condition can include criteria that can be used alone or in aggregate, to determine whether the trigger condition is met, and whether patient is admissible into a program relating to ejection fraction.

After the parameter indicative of vascular disease has been identified, the process 1500 proceeds to block 1504 wherein the patient data relevant to the parameter indicative of vascular disease is identified. In some embodiments, the identification patient data relevant to the trigger condition parameter of vascular disease can include identifying the type of data and/or the portion of the patient data applicable to the trigger condition parameter. Thus, for example, patient data including information providing an indicator of potential vascular disease can be identified.

After the patient data relevant to the trigger condition parameter has been identified, the process 1500 proceeds to decision state 606 wherein it is determined if the trigger condition parameter is met. Greater details relating to decision state 606 can be found described above.

If the trigger condition parameter is not met, then the process 1500 proceeds to block 608 wherein an indicator of the unmet parameter is added. If the trigger condition parameter is met, then the process 1500 proceeds to block 610 wherein an indicator of the met parameter is added. Further details relating to blocks 608 and 610 can be found described above.

Returning again to block 608 after the indicator of the unmet parameter has been added, the process 1500 proceeds to block 614 wherein the one or several added indicators are compared to the trigger condition. This comparison can be used to determine whether patient is admissible into the program for vascular disease. Greater details relating to block 614 can be found described above. After the indicators are compared to the trigger condition, the process 1500 proceeds to block 1506 wherein the process 1500 further proceeds to decision state 412 of FIG. 4.

Returning again to block 610, after the indicator of the met parameter has been added, the process 1500 proceeds to block 1508 wherein a parameter indicative of the severity of the vascular disease is identified. In some embodiments, the parameter indicative of the severity of the vascular disease can be included in the trigger condition data stored in the trigger database 106.

After the parameter indicative of the severity of the vascular disease has been identified, the process 1500 proceeds to block 1510 wherein the severity of the vascular disease is quantified. In some embodiments, for example, the patient data relevant to the parameter indicative of the vascular disease can be compared to the parameter indicative of the severity of the vascular disease to quantify the severity of the vascular disease. The severity of the vascular disease can be quantified as discussed above.

After the severity of the vascular disease has been quantified, the process 1500 proceeds to block 1512 wherein an indicator of the severity of the vascular disease or other ailment is added. In some embodiments, for example, the indicator of the severity of the vascular disease can be added to the patient data and can, for example, be stored in the patient database 104.

After an indicator of the severity of the vascular disease has been added, the process 1500 proceeds to block 614 wherein the indicators are compared to the trigger condition, and wherein it is determined whether patient is admissible into the program. After the indicators are compared to the trigger condition, the process 1500 proceeds to block 1506 and proceeds to decision state 412 of FIG. 4.

With reference now to FIG. 16, an exemplary chart 1600 identifying categories identifying the severity of vascular disease is shown. In some embodiments, a patient that is admitted into the vascular disease program is associated with one of the categories depicted in chart 1600. In some embodiments, the categories can be defined by a parameter of the vascular disease, by a parameter of the response to and/or desired treatment of the vascular disease, or any other desired parameter. Chart 1600 provides parameters of the response to the vascular disease that can be used in categorizing the severity of the vascular disease. Specifically, chart 1600 depicts four categories: a first category for patients designated to receive surveillance and serial monitoring, a second category for patients designated to receive additional diagnostic imaging, a third category for patients designated to be considered for therapeutic intervention, and a fourth category for patients designated for recommended immediate intervention. In some embodiments, patients in the first and second category can receive the services recommended in connection with their category from a primary care physician, and in some embodiments, patients in the third and fourth categories can receive the services recommended in connection with their category from a specialist.

Figure 17:
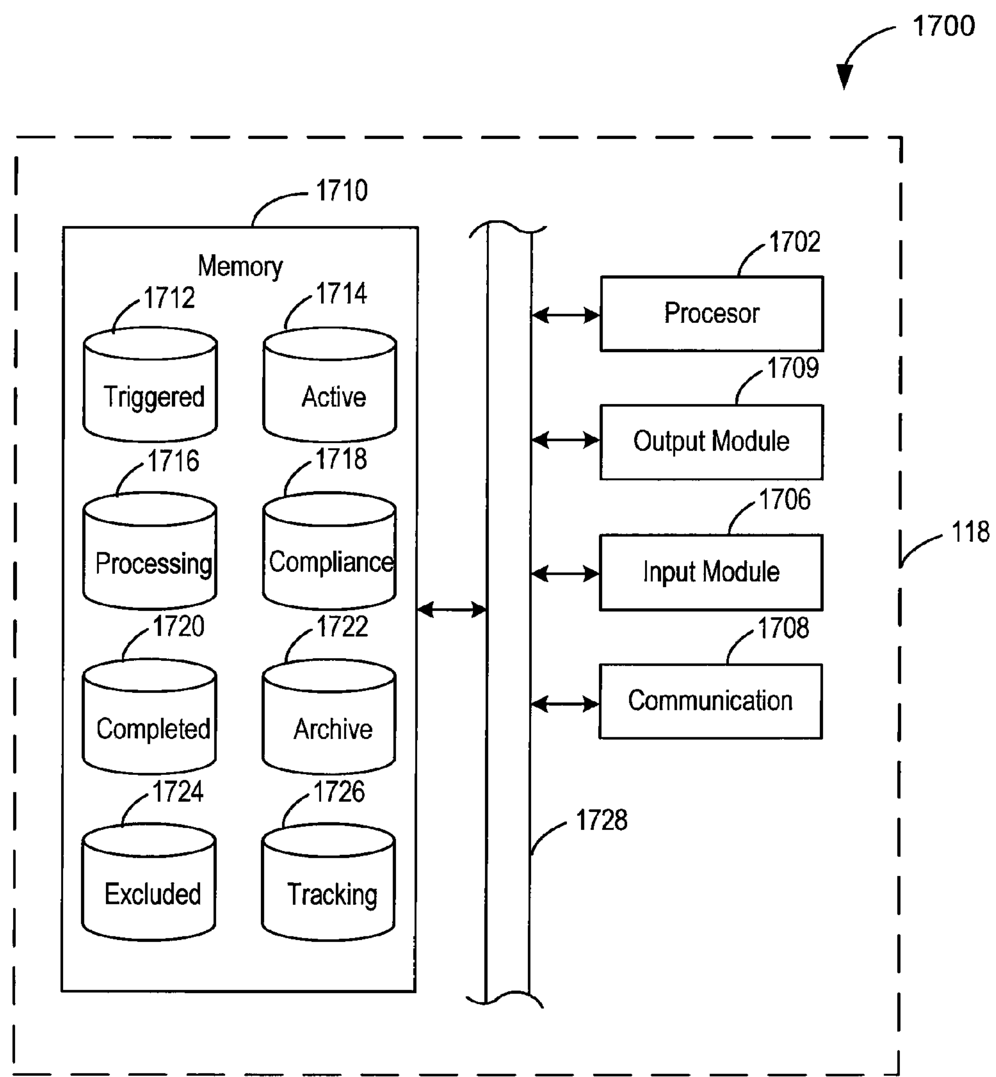
FIG. 17 is a schematic illustration of one exemplary embodiment of a nurse navigator.

With reference now to FIG. 17, a schematic illustration of a nurse navigator 1700 is shown. The nurse navigator 1700 is a system for tracking a patient's progress through a program. The nurse navigator 1700 can be one of the user devices 118 that are part of the program optimization system 100.

The nurse navigator 1700 can comprise a variety of components configured to perform a variety of functions. As depicted in FIG. 17, the nurse navigator 1700 comprises a processor 1702. The processor 1702 can provide instructions and information to, and receive information from the other components of the nurse navigator 1700. The function of the processor 1702 can be controlled by stored instructions. The processor 1702 can comprise a microprocessor, such as a microprocessor from Intel® or Advanced Micro Devices, Inc.®, or the like.

The nurse navigator 1700 can include an output module 1704. The output module 1704 can be configured to provide information to the user from the nurse navigator 1700. The output module 1704 can include features configured to provide information to the user from the nurse navigator 1700. These features can include, for example, a screen, a monitor, a speaker, a display, or any other feature configured to provide information to a user.

The nurse navigator 1700 can include an input module 1706. The input module 1706 can be configured to receive information from the user, and provide that information to the other components of the nurse navigator 1700. The input module 1706 can include features configured to allow a user to provide information to the nurse navigator 1700, such as, for example, a mouse, a button, a keyboard, a keypad, a microphone, a trackball, or any other feature that allows a user to input information.

The nurse navigator 1700 can include a memory 1710. The memory 1710 can include instructions to direct the operation of the nurse navigator 1700. Specifically, the memory 1710 can include the stored instructions that direct the operation the of processor 1702.

The memory 1710 can include one or several databases that can store information relating to the operation of the nurse navigator 1700. As seen in FIG. 17, the memory 1710 includes a triggered database 1712. The triggered database 1712 can include information relating to triggered patients. The information stored within the triggered database 1712 can be gathered from the patient database 104 of the program optimization system 100 and can be sent to the nurse navigator 1700 when a patient is categorized as admissible into a program. In some embodiments, the triggered database 1712 serves as a repository for patients that have not received any further processing from the nurse navigator 1700. Thus, for example, when patient data is received by the nurse navigator 1700, the patient is tracked within the triggered database 1712 until further action has been taken with respect to the patient.

The memory 1710 includes an active database 1714. The active database 1714 includes information indicating the program into which a patient has been admitted, information relating to patients admitted into the program, and information relating to the services provided as part of the program.

The memory 1710 includes a processing database 1716. The processing database 1716 includes information relating to a patient's progress through the program. The information in the processing database 1716 can also be stored in the patient database 104.

The memory 1710 includes a compliance database 1718. The compliance database 1718 can store information relating to how program services are provided relative to program service standards. This information can include, for example, whether services have been provided, the timeliness of the service, the quality of the service, or any other similar information. In some embodiments, for example, the compliance database 1718 can include information relating to the patient and their compliance with one or several programs. This information can include, for example, information relating to whether the patient keeps their appointments, follows lifestyle change recommendations, takes recommended medications according to directions, or any other similar information. The information in the compliance database 1718 can also be stored in the patient database 104.

Memory 1710 includes a completed database 1720. The completed database 1720 includes information identifying patients who have completed a program. This information can include the identification of a program services that the patient has received or the timeliness with which the program services were received and/or if the program was completed. The information in the completed database 1720 can also be stored in the patient database 104.

Memory 1710 includes an archive database 1722. The archive database 1722 can include information regarding patients who have not completed the program to which they been admitted, and for which no progress towards completion of the program to which they have been admitted is presently expected. These people can include, for example, individuals who have decided against receiving the services provided by a program to which they've been admitted or patients who are no longer receiving treatment from the facility associated with the program optimization system 100. The information stored within the archive database 1722 can be received from another component of the nurse navigator 1700 such as, for example, the processor 1702, the input module 1706, and/or the communication module 1708. In some embodiments, for example, this information can be received from a user via the input module 1706. In some embodiments, for example, this information can be received from other components of the program optimization system 100 via the communication module 1708. The information in the archive database 1722 can also be stored in the patient database 104.

Memory 1710 includes an excluded database 1724. Excluded database 1724 can include information relating to patients who have been admitted into the program but, to whom the services associated with the program will not be provided. These patients can include, for example, patients who died before the program could be completed, patients who are rapidly nearing death, patients who refuse the services, and/or any other patient to whom the services associated with the program will not be provided. In some embodiments, for example, a patient can be placed in the excluded database 1724 when their life expectancy is shorter than a designated threshold. In some embodiments, for example, a patient's illness and/or ailment may result in them having a truncated life expectancy. In some embodiments, the life expectancy of the patient is less than a specified threshold such as, for example, one week, one month, two months, three months, six months, nine months, 12 months, three years, five years, and/or any other or intermediate life expectancy. In such an embodiment in which the patient has a life expectancy less than the threshold value, the patient may be categorized in the excluded database 1724. The identification of a patient qualifying for classification in the excluded database 1724 can, in some embodiments, be performed by the nurse navigator 1700 and/or components of the nurse navigator 1700, and in some embodiments, identification of a patient qualifying for classification in the excluded database 1724 can, in some embodiments, be performed by the program optimization system 100 and/or other components of the program optimization system 100. The information in the excluded database 1724 can also be stored in the patient database 104.

The memory 1710 can include, for example, a tracking database 1726. The tracking database 1726 can include information identifying the patient's progress through the program and parameters associated with the patient's progress through the program. In some embodiments, the tracking database 1726 can include information such as, for example, the amount of time passed between when the patient was admitted to the program and when the program is completed, when the first service associated with the program was provided, the number and/or percentage of patients completing the program, or any other information relating to the patient's progress through the program As seen in FIG. 17 the nurse navigator 1700 includes a communication feature 1728. The communication feature 1728 can communicatingly link the components of the nurse navigator 1700 to each other. In some embodiments, the communicating feature 1728 can comprise, for example, a bus.

Figure 18:
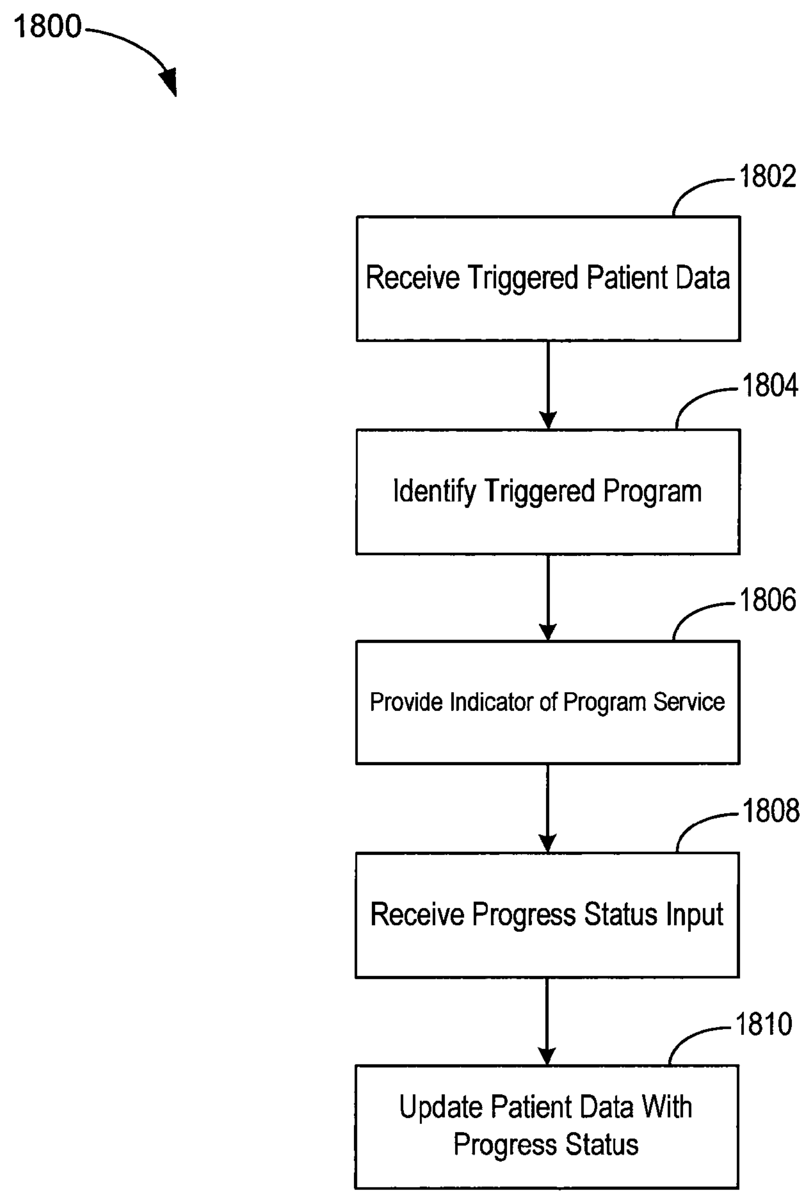
FIG. 18 is a flowchart illustrating one embodiment of a process for providing program services.

With reference now to FIG. 18, a process 1800 for providing program services is shown. In some embodiments the process 1800 can be performed by the nurse navigator 1700 and/or by components of the nurse navigator 1700.

The process 1800 begins at block 1802 wherein the triggered patient data is received. In some embodiments, for example, the triggered patient data can be received by the communications module 1708 of the nurse navigator 1700. The triggered patient data can be received from other components of the program optimization system 100 such as, for example, patient database 104, and/or the processor 120. In some embodiments, for example, the triggered patient data can be stored in the triggered database 1712.

After the triggered patient data has been received, the process 1800 proceeds to block 1804 wherein the triggered program is identified. In some embodiments, for example, the identification of the triggered program can be performed by analyzing the received triggered patient data for an indicator of the program and/or programs which have been triggered. In some embodiments, this analysis can be performed, for example, by the processor 1702 of the nurse navigator 1700.

After the triggered program has been identified, the process 1800 proceeds to block 1806 wherein an indicator of the program service and/or program protocol associated with the program is provided. In some embodiments, for example, information relating to services associated with the program can be retrieved from the active database 1714. In some embodiments, for example, this information can include stored data including instructions for providing the services related to the program such as, for example, a listing of services provided as part of the program and the steps taken to provide those services. In some embodiments, for example, providing an indicator of the program service associated with the program can include providing an indicator of the listing of services provided as part of the program and/or providing an indicator of the steps taken to provide those services. In some embodiments, for example, this indicator can be provided to a user via the output module 1704.

After the indicator of the program services provided, the process 1800 proceeds to block 1808 wherein a progress status input is received. In some embodiments, for example, the progress status input can be received by the nurse navigator 1700, and specifically by the input module 1706 and/or the communication module 1708 and can be stored within, for example, the processing database 1716, the completed database 1720, the archive database 1722, and/or the excluded database 1724. In some embodiments, for example, the progress status input can be provided by user to the nurse navigator 1700. In some embodiments, for example, the progress subset input can be generated by one or several of the patient data sources 102. In some embodiments, this information generated by one or several of the patient data sources 102 can be collected and stored within the patient database 104, and then be provided to the nurse navigator 1700.

After the progress status input has been received, the process 1800 proceeds to block 1810 wherein the patient data is updated with progress status. In some embodiments, for example, the updated patient data can include the nurse navigator 1700 sending update information to the patient database 104, and/or the nurse navigator 1700 internally updating one or more of the databases in the memory 1710 including, for example, the active database 1714, the processing database 1716, the compliance database 1718, the completed database 1720, the archive database 1722, the excluded database 1724, and/or the tracking database 1726.

Figure 19:
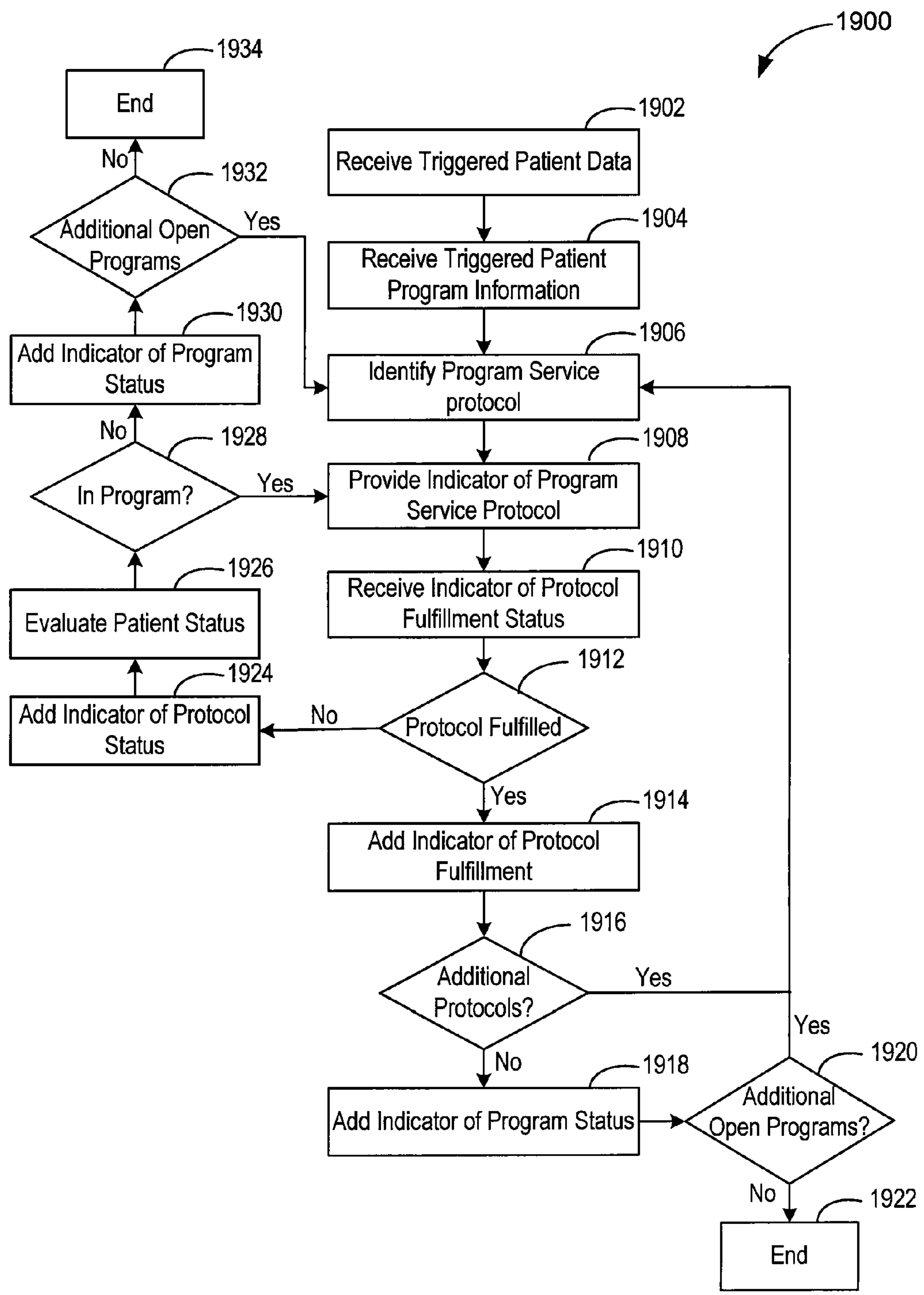
FIG. 19 is a flowchart illustrating one embodiment of a detailed process for providing services to patients within a program.

With reference now to FIG. 19, a detailed process 1900 for providing services to patients within a program is shown. Process 1900 includes the use of received patient data in determining which services to provide to the patient based on the programs into which the patient associated with the patient data has been admitted. Process 1900 additionally can include steps to determine if the patient has been admitted into multiple programs. Process 1900 can be performed by the nurse navigator 1700 and/or the components of the nurse navigator 1700.

Process 1900 begins at block 1902 wherein triggered patient data is received. The triggered patient data can be received from, for example, the triggered database 1712. The triggered patient data can include, for example, an indication of the program and/or programs into which the patient has been admitted, as well as other information relating to the patient.

After the triggered patient data has been received, the process 1900 proceeds to block 1904 wherein the triggered patient program information is received. In some embodiments, for example, the triggered patient program information can be received from the active database 1714. This information can include, for example, information relating to the program into which the patient has been admitted such as, the conditions for admission into the program, the services provided as part of the program, and any protocols associated with those services.

After the triggered patient program information has been received, the process 1900 proceeds to block 1906 wherein a program service protocol is identified. The identification of the program service protocol can be performed by, for example, the processor 1702. In some embodiments, for example, the identification of the program service protocol can include the identification of the only program service protocol within the program, and in some embodiments, the identification of program service can include the identification of one or more than one program service protocols associated with the triggered program. As discussed above, in some embodiments, for example, these protocols can correspond to individual action items associated with the program to which the patient has been admitted. In some embodiments, the triggering of the program, and or the identification of the program service protocol can be based on a component of the patient data such as, for example, the patient's status, including inpatient or outpatient status, the patient's care status, including for example, whether the patient has a primary care physician and/or specialist, or any other desired information from the patient data.

After the program service protocol has been identified, the process 1900 proceeds to block 1908 wherein an indicator of the program service protocol is provided. In some embodiments, for example, the indicator of the program service protocol can be provided, for example, to the user. In some embodiments in which the indicator of the program service protocol is provided to the user, the program service protocol can be provided to the user via the output module 1704 of the nurse navigator 1700. In some embodiments, the providing of an indicator of the program service protocol can include, for example, providing a listing of protocols and/or services to be provided in association with the program and/or a listing of action items associated with a specific protocol.

After the indicator of the program service protocol has been provided, the process 1900 proceeds to block 1910 wherein an indicator of the protocol fulfillment status is received. In some embodiments, for example, the indicator of the protocol fulfillment status can provide information relating to whether the identified protocol has been fulfilled. In some embodiments, the indicator of the protocol fulfillment status can be provided by a user to the program optimization system 100 and/or to the nurse navigator 1700. In some embodiments, for example, the indicator the protocol fulfillment status can be provided by one or several of the patient data sources 102. In the event that the indicator of the protocol film status is provided to or by a component of the program optimization system 100 other than the nurse navigator 1700, the indicator of the protocol fulfillment status can be communicated to, and stored in the patient database 104, and provided to the nurse navigator 1700. Similarly, in the event that the indicator of the protocol fulfillment status is provided to the nurse navigator 1700 via, for example, the input module 1706, the nurse navigator 1700 can communicate the indicator of the protocol fulfillment status to other components of the program optimization system 100 via the communication module 1708. In some embodiments, for example, the indicator of the protocol fulfillment status can then be stored, for example, in the patient database 104.

After the indicator of the protocol fulfillment status as been received, the process 1900 proceeds to decision state 1912 wherein it is determined if the protocol has been fulfilled. This determination can be made by the processor 1702 of the nurse navigator 1700, and can be based on the received indicator of the protocol fulfillment status. If it is determined that the protocol has been fulfilled, then the process 1900 proceeds to block 1914 wherein an indicator of the protocol fulfillment is added. In some embodiments, for example, the indicator of the protocol fulfillment can be added to, the memory 1710 of the nurse navigator 1700 including, for example, one or more of the processing database 1716, the compliance database 1718, or the tracking database 1726. In some embodiments, for example, the indicator of the protocol fulfillment can be communicated from the nurse navigator 1700 to other components of the program optimization system 100 via the communication module 1708, and, in some embodiments, the indicator of the protocol fulfillment can be added to one of the databases of the program optimization system 1100, including, for example, the patient database 104.

After the indicator of the protocol fulfillment has been added, the process 1900 proceeds to decision state 1916 wherein it is determined if there are additional protocols. In some embodiments, and as discussed above, a program may include multiple protocols. In such an embodiment, after the completion of one of the protocols, the process 1900 determines if there are additional protocols that can be completed as part of the completion of the program. This determination can be made, for example, by the processor 1702 of the nurse navigator 1700 by comparing the indicator of protocol fulfillment to the protocols received with the triggered patient program information.

If it is determined there are additional protocols, then the process 1900 returns to block 1906. If it is determined there are no additional protocols, then the process 1900 proceeds to block 1918 wherein an indicator of the program status is added. In some embodiments, the indicator of the program status can be added to the program optimization system 100, and specifically to one or more of the databases of the program optimization system 100 such as, for example, the patient database 104. In some embodiments, the indicator of program status can be added to the memory 1710 of the nurse navigator 1700, and specifically to one or more of the databases of the member in memory 1710 of the nurse navigator 1700. In one such embodiment, for example, the indicator of the program status can be added to one or more of the processing database 1716, the compliance database 1718, the completed database 1720, and/or the tracking database 1726.

After the indicator of the program status has been added, the process 1900 proceeds to decision state 1920 wherein it is determined if there are additional open programs. As discussed above, in some embodiments, a patient may be admitted into multiple programs. In some embodiments, for example, patient data gathered as part of one program may lead to the patient being admitted into an additional program. In some embodiments, for example, the patient's admission into the additional program can be directly related to the patient's progress in the original program, and in some embodiments, the patient's admission into the additional program can be unrelated to the patient's progress in the original program.

In embodiments in which the patient is admitted into multiple programs the process 1900 is configured to complete a program and then determine the existence of an additional program. If there is an additional program, the process 1900 completes that additional program. In the event that an additional program is identified, the process 1900 proceeds to block 1906, wherein program service protocol is identified. If it is determined that there are no additional open programs, then the process 1900 terminates at block 1922.

Returning again to decision state 1912, if it is determined that the protocol is not fulfilled, the process 1900 proceeds to block 1924 wherein an indicator of protocol status is added. As discussed in other paragraphs relating to FIG. 19, the indicator of the protocol status can be added to a database of the program optimization system 100 such as, for example, the patient database 104, and can be added to the memory 1710 of the nurse navigator 1700 and specifically to one or more of the databases located in memory 1710 of the nurse navigator 1700 such as, for example, processing database 1716, the compliance database 1718, or the tracking database 1726.

After the indicator of the protocol status has been added, the process 1900 proceeds to block 1926 wherein the patient status is evaluated. In some embodiments, the evaluation of the patient status can include the determination of whether the patient will continue within the program. This determination can include, for example, determining whether the patient is deceased, determining whether the patient's lifespan is too short to warrant further admission into the program, determining whether the patient has refused care through the program, determining whether the patient still wants to participate in the program, determining whether the patient is sufficiently healthy to continue in the program, determining that the ailment giving rise to a patient's admission in the program has been resolved, and/or any other determination relevant to the patient's admissibility into the program. This evaluation of the patient status can be made, for example, by the processor 1702 of the nurse navigator 1700 or by a component of the program optimization system 100 such as, for example, the processor 120.

After the patient status is evaluated, the process 1900 proceeds to decision state 1928 wherein it is determined if the patient is still in the program and still active in the program. If it is determined that the patient is still active and admitted into the program, the process 1900 proceeds to block 1908 wherein an indicator of program service protocol is provided. In the event that the patient is not still in the program and/or is not still active in the program, then the process 1900 proceeds to block 1930 wherein an indicator of the program status is added. In some embodiments, for example, the indicator of program status can be added to a database of the program optimization system 100 such as, for example, patient database 104, or the outcome database 114. In some embodiments, for example, the indicator of program status can be added to the memory 1710 of the nurse navigator 1700, and specifically to one of the databases located in the memory 1710 of the nurse navigator 1700 such as, for example, the processing database 1716, the compliance database 1718, the archive database 1722, the excluded database 1724 and/or the tracking database 1726.

After the indicator of the program status has been added, the process 1900 proceeds to decision state 1932 wherein it is determined if there are additional open programs. In some embodiments, and as discussed above, a program may include multiple protocols. In such a case, after the completion of one of the protocols, it is determined if there are additional protocols that can be completed as part of the completion of the program. This determination can be made, for example, by the processor 1702 of the nurse navigator 1700 by comparing the indicator of protocol fulfillment to the protocols received with the triggered patient program information. If it is determined that there are additional open programs, then the process 1900 proceeds to block 1906 wherein a program service protocol is identified. If it is determined there are no additional programs, then the process 1900 terminates at block 1934.

Figure 20:
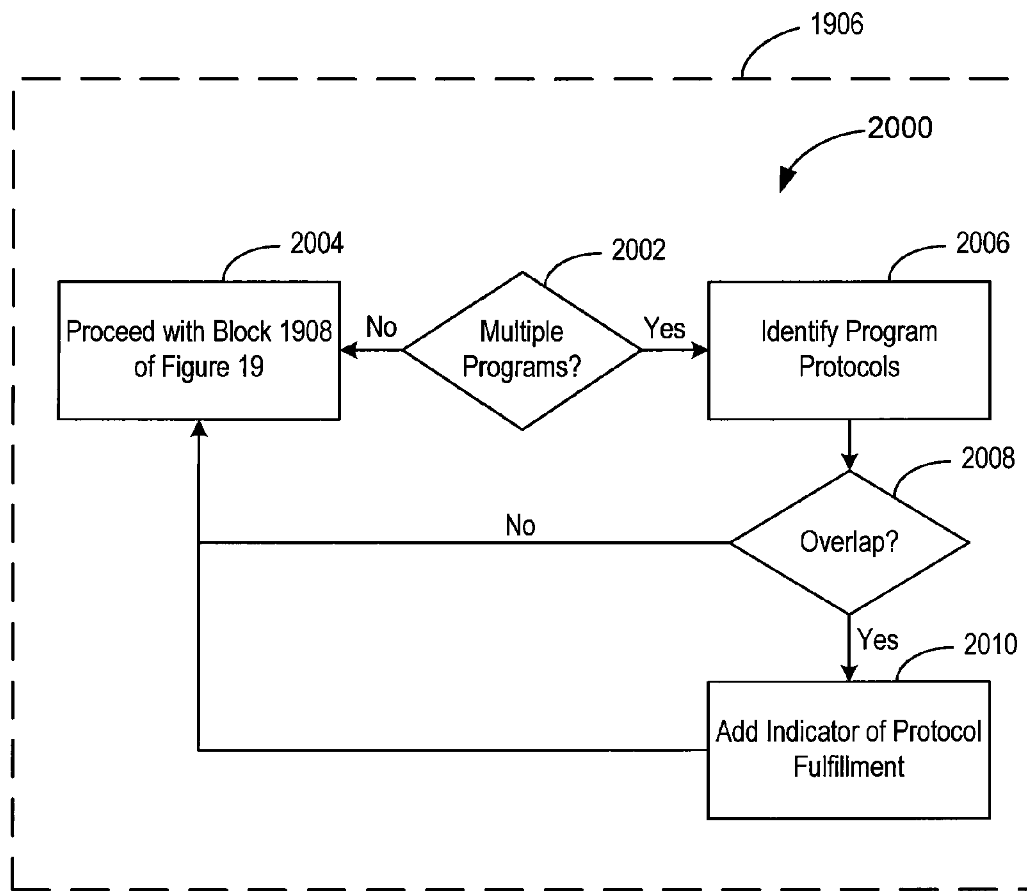
FIG. 20 is a flowchart illustrating one embodiment of a process for identifying a program service protocol.

With reference now to FIG. 20, a flowchart illustrating a process 2000 for identifying a program service protocol is depicted. The process 2000 can be configured to facilitating optimizing resource use in identifying overlapping actions between multiple programs into which a patient has been admitted. In some embodiments, for example, this can include identifying protocols in each of the programs that include the same action, and thus overlap. Advantageously, the identification of such overlap efficiently manages resources and decreases the costs associated with providing services associated with a program. Further, the identification of such overlap between multiple programs into which the patient has been admitted decreases the burden placed on the patient in dealing with healthcare providers. As indicated by the dotted line labeled 1906 around the process 2000, the process 2000 can be performed as part of block 1906 of FIG. 19.

The process 2000 begins at decision state 2002 wherein it is determined if the patient has been admitted into multiple programs. In some embodiments, for example, this determination as to whether the patient has been admitted into multiple programs can be based on the received triggered patient data, and can be made by the processor 1702. If the patient has not been admitted into multiple programs, then the process 2000 proceeds to block 2004 and proceeds to block 1908 of FIG. 19.

If the patient has been admitted into multiple programs, then the process 2000 proceeds to block 2006 wherein the program protocols for each of the programs to which the patient has been admitted are identified. In some embodiments, for example, this identification can include the evaluation of the received triggered patient data for protocol information. In some embodiments, for example, the identification of the program protocols for each of the programs into which the patient has been admitted can be performed by the processor 1702.

After the program protocols for each of the programs into which the patient has been admitted have been identified, the process 2000 proceeds to decision state 2008 wherein it is determined if there is overlap between the protocols, which is to say whether some or all of the protocols for the programs into which the patient has been admitted are the same. In some embodiments, for example, this determination can be made by the processor 1702 and can include the comparison of each of the protocols with the protocols of the other programs into which the patient has been admitted. If there is no overlap between the protocols of the programs into which the patient has been admitted, then the process 2000 proceeds to block 2004 and proceeds to block 1908 of FIG. 19.

If it is determined that there is overlap between the protocols of the programs into which the patient has been admitted, then the process 2000 proceeds to block 2010 wherein an indicator linking the overlapping program protocols is added. In some embodiments, for example, the indicator linking the overlapping program protocols can be an indicator added to the patient data linking the programs and the overlapping protocols to each other. In some embodiments, this addition to the patient data can be made in the patient database 104 of the program optimization system 100 and/or in the memory 1710 of the nurse navigator 1700 including, for example, in one or more of the databases located in the memory 1710 of the nurse navigator 1700 such as, for example, the processing database 1716. After the indicator linking the overlapping program protocols has been added, the process 2000 proceeds to block 2004 and proceeds to block 1908 of FIG. 19.

Figure 21:
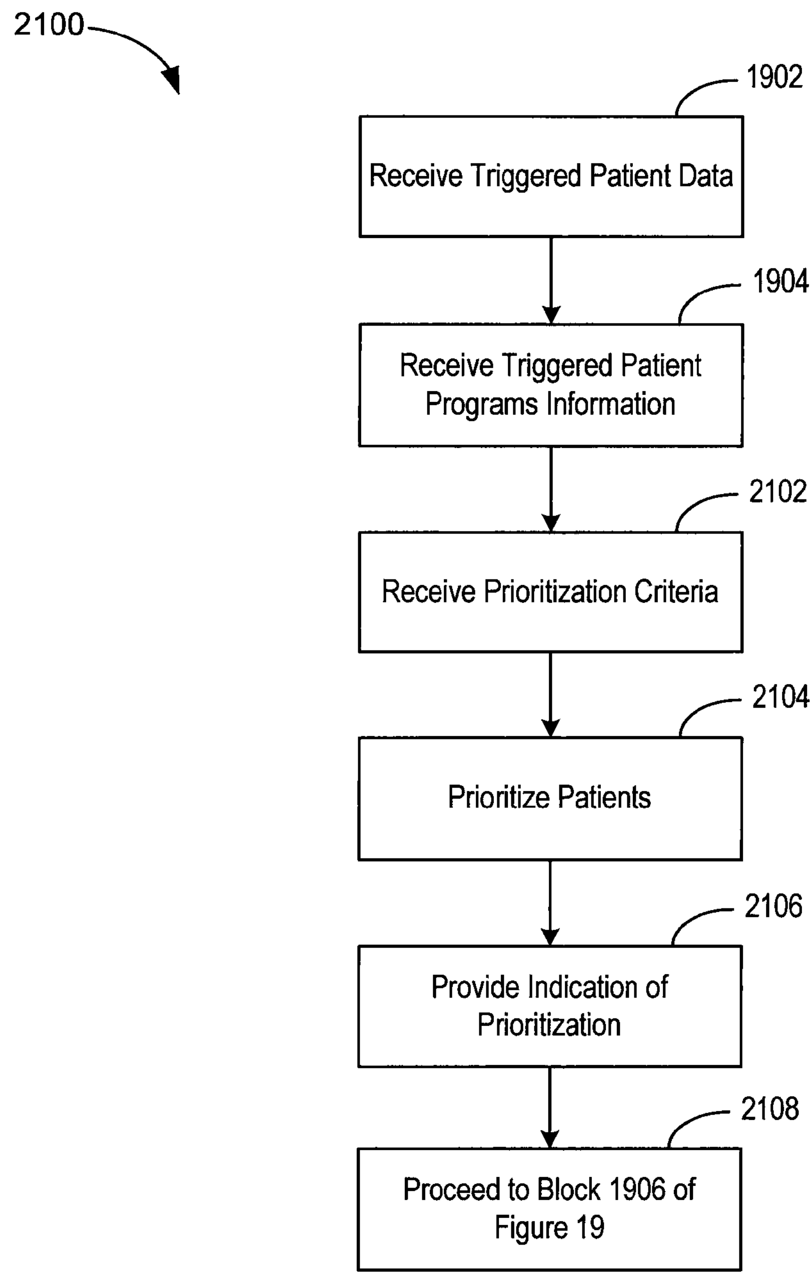
FIG. 21 is a flowchart illustrating one embodiment of a process for prioritizing patients.

With reference now to FIG. 21, a flowchart illustrating process 2100 for prioritizing patients is shown. In some embodiments, the process 2100 for prioritizing patients can facilitate in the management and in the providing of care to a large number of patients by prioritizing the patients having the most immediate need for care. In some embodiments, for example, the prioritization of the patients can include the relative prioritization of one patient to another, and in some embodiments, for example, the prioritization of the patient can include the relative prioritization of the programs into which the patient has been admitted.

The process 2100 begins at block 1902 wherein the triggered patient data is received. The triggered patient data can be received from, for example, the triggered database 1712. The triggered patient data can include, for example, an indication of the program and/or programs into which the patient has been admitted, as well as other information relating to the patient.

After the triggered patient data has been received, the process 2100 proceeds to block 1904 wherein the triggered patient programs information is received. In some embodiments, for example, the triggered patient program information can be received from the active database 1714. This information can include, for example, information relating to the program into which the patient has been admitted such as, the conditions for admission into the program, the services provided as part of the program, and any protocols associated with those services.

After the triggered patient program information has been received, the process 2100 proceeds to block 2102 wherein the prioritization criteria is received. In some embodiments, for example, the prioritization data can be received from a database of the program optimization system 100 such as, for example, the trigger database 106 and/or from the memory 1710 of the nurse navigator 1700 including, for example, one of the databases of the memory 1710 of the nurse navigator 1700 such as, for example, the triggered database 1712.

In some embodiments, the prioritization criteria can include information for prioritizing the patients. This can include information for prioritizing the severity of a patient's ailment that resulted in their admission into a program, and can, in some embodiments, include information for the relative ranking of multiple programs into which a patient has been admitted.

After the prioritization criteria have been received, the process 2100 proceeds to block 2104 wherein the patients are prioritized. In some embodiments, for example, the patients can be prioritized relative to other patients within a single program. These prioritizations can be based on, for example, the severity of the reason for the admission of the patient into the program, the risk levels of the patients admitted into a program, or any other desired factors. In some embodiments, for example, the programs into which a patient has been admitted can be prioritized relative to each other. In some embodiments, for example, this relative prioritization of the programs into which the patient has been admitted can be based on, for example, the relative severity of the underlying causes giving rise to the admission into the multiple programs and/or the relative severity of the ailments that are addressed in the programs into which the patient has been admitted. In some embodiments, for example, the prioritization of the patients can be performed by the processor 1702 of the nurse navigator 1700.

After the patients have been prioritized, the process 2100 proceeds to block 2106 wherein an indication of the prioritization is provided. In some embodiments, for example, the indication of the prioritization can be provided by adding an indication of the prioritization to the patient data of the patients affected by the prioritization. In some embodiments, for example, the indication of prioritization can be added to the patient data stored in the patient database 104 of the program optimization system 100, and in some embodiments, for example, the indication of prioritization can be added to the patient data stored in the triggered database 1712, the active database 1714, the processing database 1716, the compliance database 1718, the completed database 1720, the archive database 1722, and/or the excluded database 1724. After the indication of prioritization has been added, the process 2100 proceeds to block 2108 and proceeds to block 1906 of FIG. 19.

Figure 22:
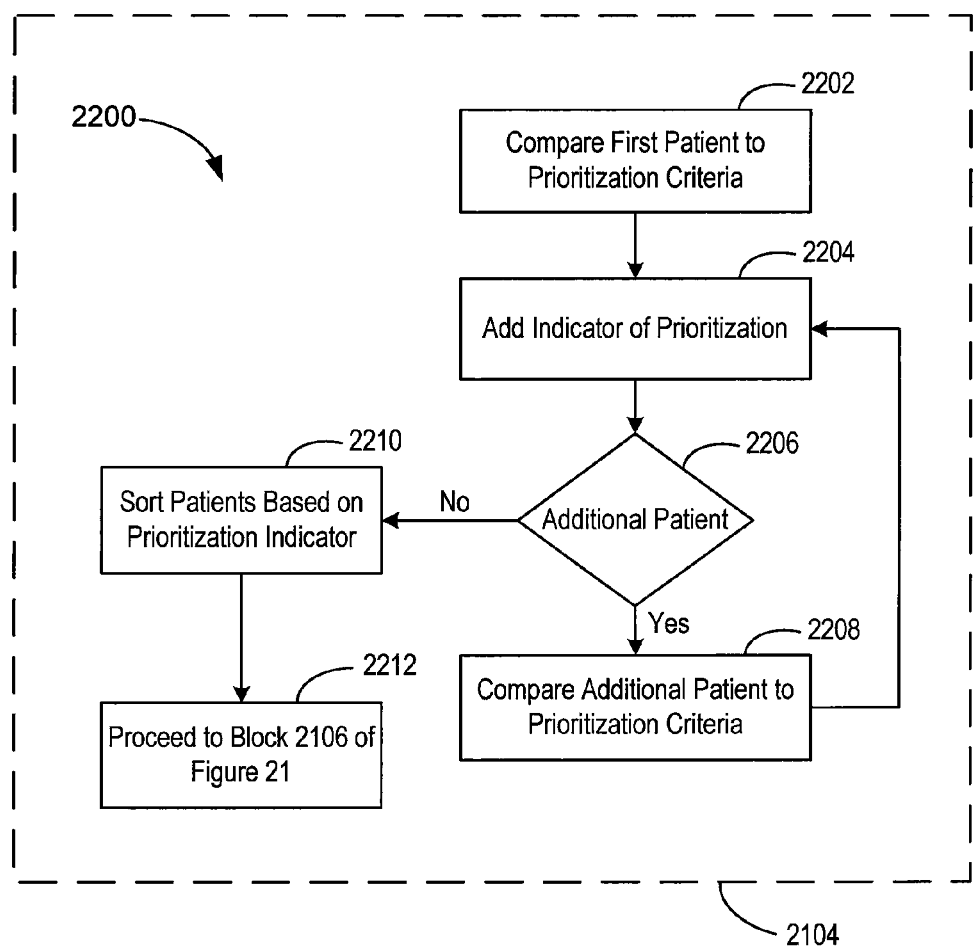
FIG. 22 is a flowchart illustrating one embodiment of aspects of the process for prioritizing patients.

With reference now to FIG. 22, a flowchart illustrating a process 2200 for prioritizing patients is shown. As indicated by the dotted line labeled 2104 around the process 2200, the process 2200 can be performed as part of block 2104 of FIG. 21.

Process 2200 begins at block 2202 wherein the first patient is compared to the prioritization criteria. In some embodiments, for example, the comparison of the first patient to the prioritization criteria can be performed by the processor 1702 of the nurse navigator 1700. In some embodiments, for example, this comparison can include comparing any factor relating to the patient's admission into the program with the prioritization criteria. This comparison can result, for example, in the creation of a prioritization score and/or an indicator of prioritization.

After the first patient is compared to the prioritization criteria, the process 2200 proceeds to block 2204 wherein an indicator of the prioritization is added. In some embodiments, for example, the indicator of prioritization can be added to the patient data and can be, for example, stored in the patient database 104 of the program optimization system 100, or in the memory 1710 of the nurse navigator 1700. In some embodiments, the indicator of prioritization can be stored in one of the databases of the memory 1710 of the nurse navigator 1700 such as, for example, the triggered database 1712, the active database 1714, the processing database 1716, the compliance database 1718, the completed database 1720, the archive database 1722, the excluded database 1724, and/or the tracking database 1726.

After the indicator of the prioritization has been added, the process 2200 proceeds to decision state 2206 wherein it is determined if there is an additional patient. In some embodiments, for example, the determination of whether there is an additional patient can include determining whether the program into which the patient has been admitted includes multiple patients. This determination can include evaluating patient data, triggered patient data, and/or program data such as, the data stored within one of the databases of the program optimization system 100 or the nurse navigator 1700. In some embodiments, these databases can include, for example, the patient database 104, the active database 1714, the processing database 1716, the compliance database 1718, the completed database 1720, the archive database 1722, the excluded database 1724, and/or the tracking database 1726.

If it is determined that the program into which the patient has been admitted includes additional patients, then the process 2200 proceeds to block 2208 wherein the additional patient is compared to the prioritization criteria. In some embodiments, for example, the comparison of the additional patient to the prioritization criteria can be performed by the processor 1702 of the nurse navigator 1700. In some embodiments, for example, this comparison can include comparing any factor relating to the patient's admission into the program with the prioritization criteria, which comparison can result, for example, in the creation of a prioritization score and/or prioritization indicator. After the additional patient has been compared to the prioritization criteria, the process 2200 proceeds to block 2204 wherein the indicator of the prioritization is added.

Returning again to decision state 2206, if it is determined that there is no additional patient, the process 2200 proceeds to block 2210 wherein the patients in the program are sorted based on their prioritization indicators. In some embodiments, for example, this sorting can be performed by the processor 1702 of the nurse navigator 1700. In some embodiments, for example, the sorting of the patients based on the prioritization indicator can result in sorting the patients such that those requiring the most immediate attention comparatively receive services associated with the programs into which the patient has been admitted earlier than those patients admitted into the program and requiring less immediate attention. After the patients are sorted based on the prioritization indicators, the process 2200 proceeds to block 2212 and proceeds to block 2106 of FIG. 21.

Figure 23:
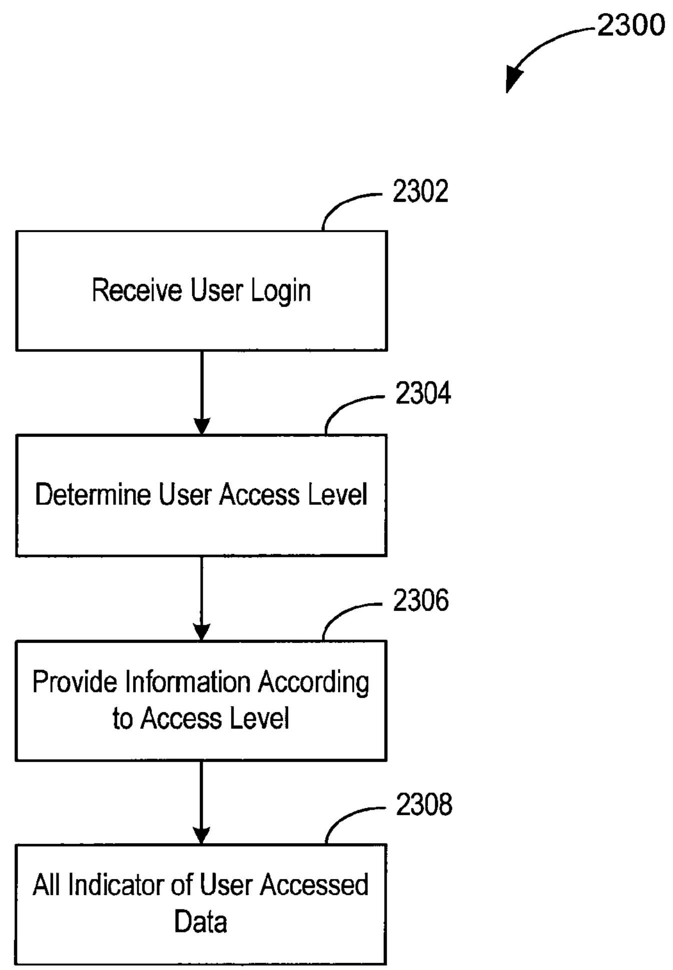
FIG. 23 is a flowchart illustrating one embodiment of a process for providing data security.

With reference now to FIG. 23, a flowchart illustrating a process 2300 for providing data security is provided. In some embodiments, the process 2300 can provide access to data based on an access level and track a user receiving access to data. Advantageously, by limiting access to data according to an access level, a user's access to patient data can be limited and security can be increased. Further advantageously, by tracking a user receiving access to data, users can be held accountable for the misuse and/or misappropriation of patient data. The process 2300 can be performed by, for example, the program optimization system 100 and/or the nurse navigator 1700.

The process 2300 begins at block 2302 wherein the user login is received. In some embodiments, the user login can uniquely identify the user. In some embodiments, for example, the user login can be received at the nurse navigator 1700, and specifically, in some embodiments, for example, a user can use the input module 1706 of the nurse navigator 1700 to provide the user login. The user login can be verified by comparing the user login to login information stored in the access database 116 to verify that the user login is correct. If the provided user login is correct, then access to the program optimization system 100 can be granted. If the provided user login is incorrect, then access to the program optimization system 100 can be prevented.

After the user login is received, the process 2300 proceeds to block 2304 wherein the user access level is determined. In some embodiments, for example, the processor 120 can query the access database 116 with the user login information and/or other parameter related to the user, and can receive the access level associated with the user and corresponding to the amount and type of patient data that the user can access.

After the user access level is determined, the process 2300 proceeds to block 2306 wherein information is provided to the user according to the access level. In some embodiments, for example, the patient data can be filtered according to the access level so that the user's access to the patient data is limited based on his access level. Thus, when the user's access level is based on the patient data used by the user in fulfilling his program related responsibilities, the user's access to patient data is limited to the patient data that is used in the performance of those responsibilities. Specifically, in one embodiment, the user may receive patient data excluding, for example, the patient's address and the patient's social security number when this information is not used by the user in the performance of his program related responsibilities.

After information is provided according to the user's access level, the process 2300 proceeds to block 2308 and an indicator of the data accessed by the user is added. In some embodiments, for example, the indicator of the data accessed by the user can be added to, for example, the access database 116 of the program optimization system 100. In some embodiments, for example, the indicator of the data accessed by the user can include information relating to the time and location that the data was accessed, the duration of the time for which the data was accessed, any changes made to the patient data, and whether all or a portion of the patient data was copied, transmitted, printed, or misappropriated in any way.

Figure 24:
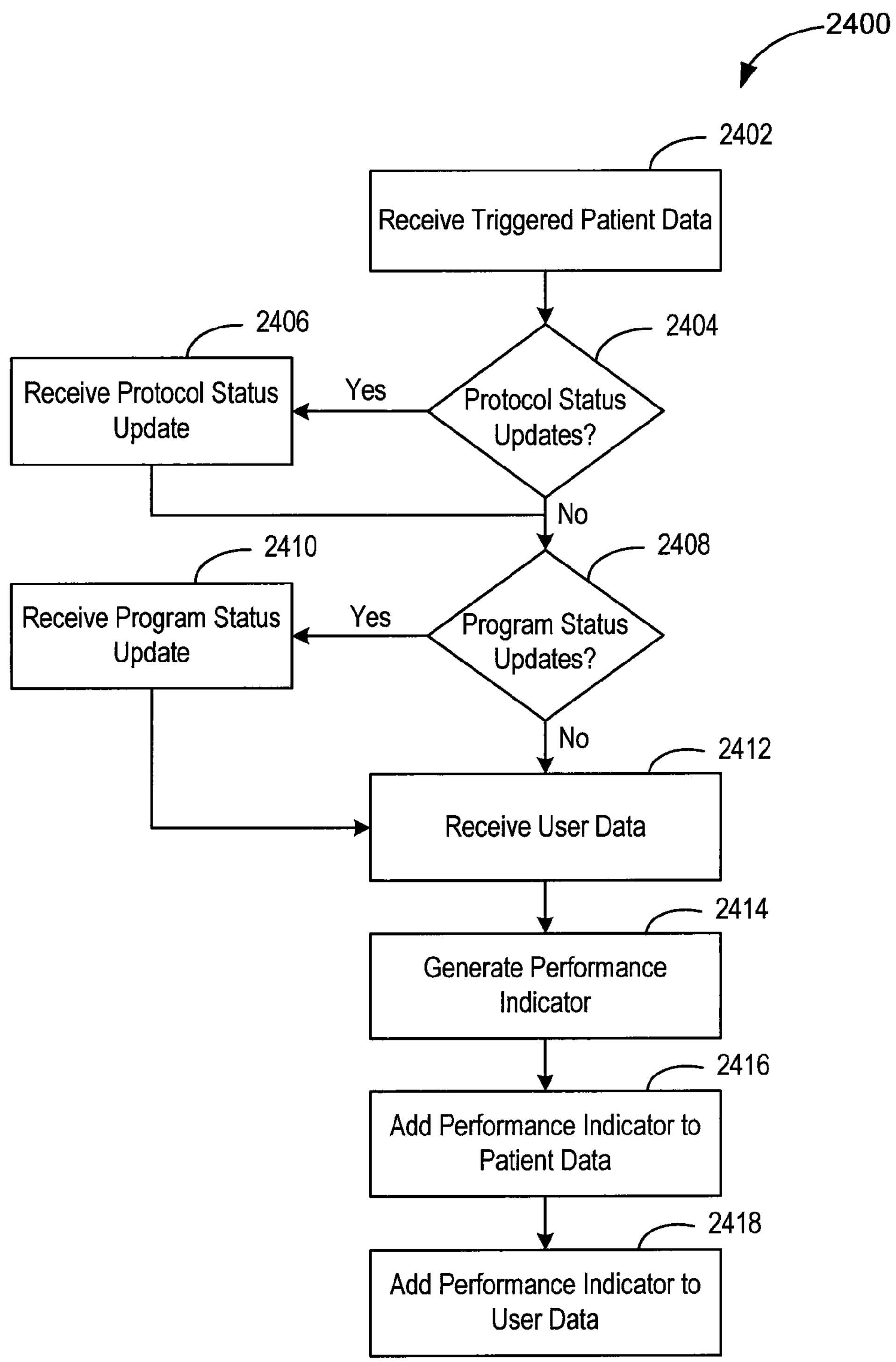
FIG. 24 is a flowchart illustrating one embodiment of a process for tracking user performance.

With reference now to FIG. 24, a flowchart illustrating a process 2400 for tracking user performance is depicted. In some embodiments, the process 2400 for tracking user performance can be used to generate data relating to user. This data can be used in a variety of ways including, for example, to improve user performance or to improve the quality services provided to the patient. In some embodiments, for example, the program optimization system 100 can collect data from a variety of sources and/or components of the program optimization system 100 in order to track user performance.

The process 2400 begins at block 2402 wherein triggered patient data is received. The received triggered patient data can include information relating to the patient and to the programs into which the patient has been admitted. In some embodiments, for example, the triggered patient data can include information relating to, for example, a target timeframe in which the patient is expected to have completed the program and/or the programs into which he has been admitted, and in some embodiments, for example, this timeframe can be based on the prioritization of the patient and/or the prioritization of the program or the risk associated with the underlying patient condition or conditions giving rise to the patient's admission into the one or several programs.

In some embodiments, for example, the triggered patient data can include an indicator of the time at which the patient was admitted into the program. This indicator can identify the time of day, the day, the week, the month, or any other desired period of time that identifies when the patient is admitted into the program. The triggered patient data can be stored in, for example, the patient database 104, the outcome database 114, the triggered database 1712, the tracking database 1726, or any other desired database.

After the triggered patient data has been received, the process 2400 proceeds to decision state 2404 wherein it is determined if there are protocol status updates. In some embodiments, for example, the determination of whether there is a protocol status update can be made by the processors 120 and 1702 querying the database wherein protocol status updates are stored and receiving an indicator of whether a protocol status update has been received in a designated time period. In some embodiments, the process 2400 can wait until the protocol status update is received, and when the protocol status update has been received, determine that there is a protocol status update. If there is a protocol status update, then the process 2400 proceeds to block 2406 wherein the protocol status update is received. The protocol status update can be received from, for example, one of the user devices 118 such as, for example, the nurse navigator 1700.

If it is determined in decision state 2404 that there is no protocol status update, then the process 2400 proceeds to decision state 2408 wherein it is determined if there are program status updates. In some embodiments, for example, the determination of whether there is a program status update can be made by the processor 120, 1702 querying the database wherein the program status updates are stored and receiving an indicator of whether a program status update has been received in a designated time. In some embodiments, the process 2400 can wait until the program status update is received, and then, when the program status update has been received, determine that there is a program status update. If there is a program status update, then the process 2400 can proceed to block 2410 wherein the program status update is received. The program status update can be received, for example, from one of the user devices 118 such as, for example, the nurse navigator 1700.

After the program status update has been received, the process 2400 proceeds to block 2412 wherein the user data is received. In some embodiments, for example, the user data can identify the user associated with the program and/or associated with the patient. This data can include, for example, the user's name, the username, an identification number, an employee identification number, or any other information that identifies the user. This data can further include user performance information. The user performance information can, for example, provide information relating to the past performance of the user. This past performance of user can relate to, for example, the average amount time taken by that user to complete one or several protocols within a program and/or complete one or several programs. In some embodiments, the past performance of the user can further include data such as, for example, the number and/or percentage of patients who complete and/or graduate from a program, the number and/or percentage of patients who do not complete a program, and the number and/or percentage of patients having a specified reason for not completing a program such as, for example, death, approaching death, refusal to accept services, or inability to receive services. In some embodiments the user data can be received from, for example, the access database 116.

After the user data is received, the process 2400 proceeds to block 2414 wherein a performance indicator is generated. In some embodiments, for example, the performance indicator can be a value that reflects the user's performance with regards to a patient, to several patients, to a protocol, to several protocols, to a program, or to several programs. The performance indicator can reflect, for example, the amount of time taken by the user to complete one or several protocols, one or several programs, and/or to provide services to one or several patients. In some embodiments, the performance indicator can reflect, for example, a user's protocol completion percentage and/or the user's program completion percentage. In some embodiments, for example, the performance indicator can be generated by the processor 120, 1702.

After the performance indicator has been generated, the process 2400 proceeds to block 2416 wherein the performance indicator is added to the patient data. In some embodiments, for example, the performance indicator can be added to the patient data by the processor 120, 1702, and, in some embodiments, the performance indicator can be stored in one of the databases in the program optimization system 100 and/or in one of the databases of the nurse navigator 1700. In one embodiment, for example, the performance indicator can be stored, for example, in the patient database 104.

After the performance indicator has been added to the patient data, the process 2400 proceeds to block 2418 wherein the performance indicator is added to the user data. In some embodiments, for example, the performance indicator can be added to the user data by the processor 120, 1702. In some embodiments, for example, the performance indicator can be stored in one of the databases in the program optimization system 100 and/or in one of the databases of the nurse navigator 1700. In one embodiment, for example, the performance indicator can be stored, for example, in the administrator database 112 and/or in the access database 116.

Figure 25:
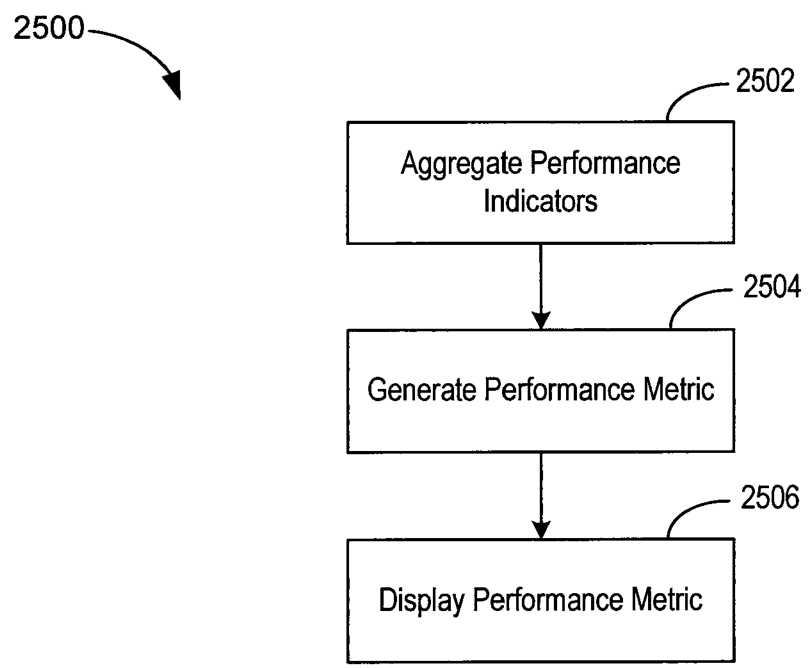
FIG. 25 is a flowchart illustrating one embodiment of a process for generating a performance metric.

With reference now to FIG. 25, a flowchart illustrating a process 2500 for generating a performance metric is shown. In some embodiments, for example, the performance indicators generated by process 2400 can be used to generate the performance metric. The performance metric can provide information relating to the performance of a number of users. In some embodiments, the performance metric characterizes the performance of a group of users that are associated by working on the same program, with the same protocols, at the same location, and/or with any other desired association. A person of skill in the art will realize that the performance metric can be used to capture performance data relating to any group of users and/or any data useful in characterizing the performance of the users. In some embodiments, for example, the process 2500 for generating the performance metric can be performed by the program optimization system 100.

Process 2500 begins at block 2502 wherein performance indicators are aggregated. In some embodiments, for example, performance indicators are aggregated from the group of users for which the performance metric is to be generated. In some embodiments, for example, the aggregation of the performance indicators can include querying databases for user data and/or patient data related to the users. These queried databases can include, for example, the patient database 104, the administrator database 112, the outcome database 114, the access database 116, or the tracking database 1726. This information can be received from the databases and can be aggregated within, for example, one of the databases of the program optimization system 100 or the nurse navigator system 1700 including, for example, the administrator database 112, the outcome database 114, the access database 116, or the tracking database 1726.

After the performance indicators have been aggregated, the process 2500 proceeds to block 2504 wherein the performance metric is generated. In some embodiments, for example, the performance metric can be a relative metric indicating performance relative to some standard, and in some embodiments, the performance metric can be an absolute metric. In some embodiments, for example, a relative metric may include information categorizing user performance as unsatisfactory, satisfactory, or excellent. In some embodiments, for example, the absolute metric may include information relating to the user performance such as, for example, statistics relating to the average time taken to complete one or several protocols, one or several programs, or complete providing care for one or several patients. The calculation of the absolute metric may include the aggregation of one or several performance indicators and performing statistical analysis on the one or several performance indicators in order to achieve the desired metric. In some embodiments, for example, this analysis can include determining a mean time for completing one or several protocols, completing one or several programs, and/or completing the providing of care for one or several patients. In some embodiments, for example this analysis can include similarly calculating a median time, standard deviation, or any other desired value based on performance indicators. In some embodiments, for example, the performance metric can be generated by the processor 120, 1702.

After the performance metric has been generated, the process 2500 proceeds to block 2506 wherein the performance metric is displayed. In some embodiments, for example, the performance metric can be displayed on one or several of the user devices 118, including, for example, an administrator device and/or the nurse navigator 1700.

Figure 26:
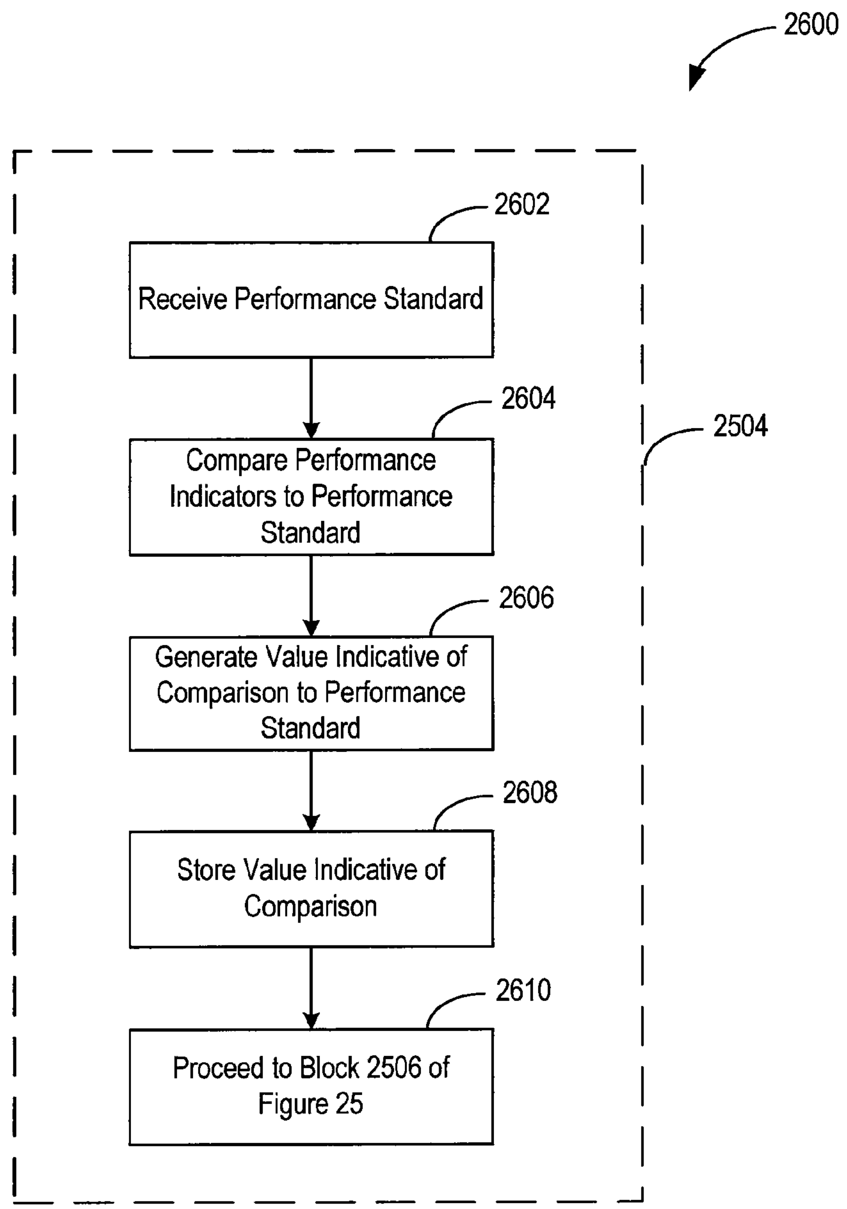
FIG. 26 is a flowchart illustrating one embodiment of a process for generating a relative performance metric.

With reference now to FIG. 26, a flowchart illustrating a process 2600 for generating a relative performance metric is shown. As indicated by the dotted line labeled 2504 around the process 2600, the process 2600 can be performed in the place of block 2504 shown in FIG. 25.

The process 2600 begins in block 2602 wherein a performance standard is received. In some embodiments, for example, the performance standard can provide thresholds to qualify user performance. In some embodiments, the performance standard can be received from, for example, the administrator database 112.

After the performance standard has been received, the process 2600 proceeds to block 2604 wherein performance indicators are compared to the performance standard. In some embodiments, for example, the comparison of a plurality of performance indicators to the performance standard can allow the evaluation of the aggregated user group. In some embodiments, the comparison of the performance indicators to the performance standard can include the serial comparison of a single indicator to the performance standard until a group of indicators has been compared to the performance standard, or the aggregation of a plurality of indicators into a single indicator and comparing the aggregated indicator to the performance standard. In some embodiments, for example, the comparison of the performance indicators to the performance standard can result in the determination of the performance characterized by the indicators being, for example, unsatisfactory, satisfactory, or exceptional. The comparison of the performance indicators to the performance standard can be performed by the processor 120.

After the performance indicators are compared to the performance standard, the process 2600 proceeds to block 2606 wherein a value indicative of the comparison of the performance indicators to the performance standard is generated. In some embodiments, for example, the value indicative of the comparison of the performance indicators to the performance standard can be generated by the processor 120. After the value indicative of the comparison of the performance indicators to the performance standard is generated, the process 2600 proceeds to block 2608 wherein the value indicative of the comparison of the performance indicators to the performance standard is stored. In some embodiments, for example, the value indicative of the comparison of the performance indicators to the performance standard can be stored, for example, in one of the databases of the program optimization system 100 such as, for example, the administrator database 112. After the value indicative of the comparison of the performance indicators to the performance standard is stored, the process 2600 proceeds to block 2610 and proceeds to block 2506 of FIG. 25.

Figure 27:
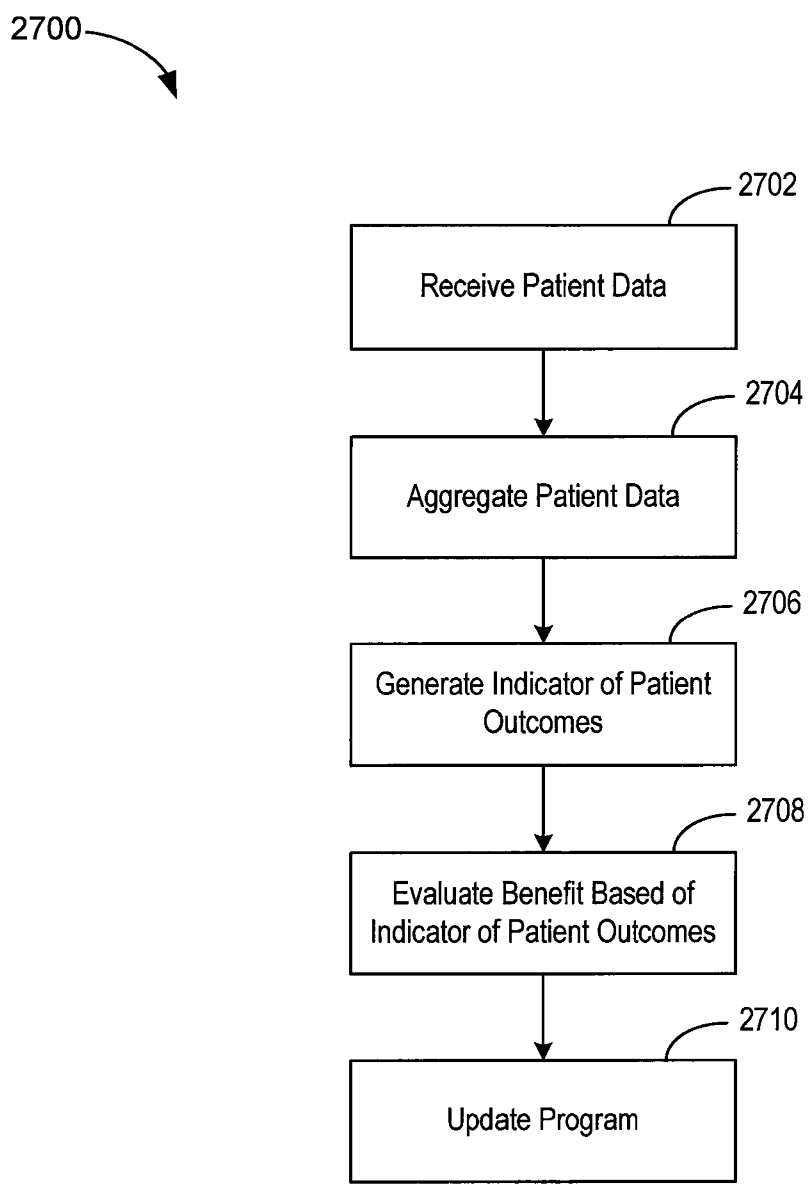
FIG. 27 is a flowchart illustrating one embodiment of a process for program optimization.

With reference now to FIG. 27, a flowchart illustrating one embodiment of a process 2700 for program optimization is shown. In some embodiments, the process 2700 for program optimization can collect data from the program optimization system 100 relating to program and patient outcomes. This information can be used, for example, to evaluate the benefit of the program and/or of one or several program protocols, and can, in some embodiments, be used to update and/or change the program and/or one or several program protocols based on the evaluation. The process 2700 for program optimization can be performed by the program optimization system 100.

Process 2700 for program optimization begins at block 2702 wherein patient data is received. In some embodiments, the patient data can be received from the patient database 104. The patient data can include information relating to one or more programs into which the patient has been admitted, the completion status of the one or more programs into which the patient has been admitted, and/or the patient condition following the completion of the one or more programs.

After the patient data has been received, the process 2700 proceeds to block 2704 wherein the patient data is aggregated. In some embodiments, for example, patient data can be aggregated according to the scope of the evaluation of the process 2700 for program optimization. Thus, for example, in some embodiments in which a program protocol is to be evaluated, patient data can be aggregated for patients who have completed the specified program protocol. Similarly, for example, in some embodiments in which a program is to be evaluated, patient data can be aggregated for patients who have completed the specified program. The patient data can be aggregated by the processor 120 of the program optimization system 100.

After the patient data has been aggregated the process 2700 proceeds to block 2706, wherein an indicator of the patient outcomes is generated. In some embodiments, for example, the indicator of the patient outcomes can be an indicator providing information relating to any changes in patients' patient data from before one or more of the protocols and/or programs to after one or more of the protocols and/or programs. In some embodiments, for example, the indicator of the patient outcomes can track any changes in patient data of a single patient, and/or any changes in patient data of a plurality of patients. The indicator of the patient outcomes can be generated by, for example, the processor 120.

After the indicator of the patient outcomes has been generated, the process 2700 proceeds to block 2708 wherein the benefit of the one or several protocols and/or programs is evaluated based on the indicator of the patient outcomes. In some embodiments, for example, the evaluation of the benefit of the one or several protocols and/or programs can be an evaluation of the absolute benefit and/or on evaluation of the relative benefit of the one or several protocols and/or programs.

In some embodiments, for example, the evaluation of the benefit of the one or several protocols and/or programs can involve the determination of the most effective protocols and/or programs in treating an ailment and/or condition giving rise to a patient's admission into one or more of the programs. In some embodiments, for example, a plurality of programs can be used to address a single ailment and/or condition giving rise to admission into each of the plurality of the programs. In such an embodiment, the evaluation of the benefit of the plurality of programs can include a comparison of the benefits of the plurality of programs to each other to thereby determine which program most effectively addresses the underlying ailment and/or condition giving rise to the patient's admissibility into the plurality of programs. In some embodiments, for example, the evaluation of the benefit of the one or several protocols and/or programs can include the normalization of the benefit based on the cost of the one or several protocols and/or programs. In some embodiments, for example, the cost of the one or several protocols and/or programs can include the dollar cost, the cost in resources, the cost in time, and/or any other cost associated with the one or several protocols and/or programs. In some embodiments, for example, the benefit of the one or several protocols and/or programs can be evaluated by the processor 120.

After the benefit of the one or several protocols and/or programs has been evaluated, the process 2700 proceeds to block 2710, wherein the one or several protocols and/or programs are updated. In some embodiments, for example, the updated one or several protocols and/or programs can include the elimination and/or change to the least effective and/or ineffective of the one or several protocols and/or programs. In some embodiments, for example, the updated one or several protocols and/or programs can include the addition of new protocols, sub protocols, and/or programs. In some embodiments, for example, the updated protocols and/or programs can be stored in, for example, one of the databases of the program optimization system 100 and/or of the nurse navigator 1700. In some embodiments, for example, these databases can include, for example, the program database 110 and/or the active database 1714.

Figure 28:
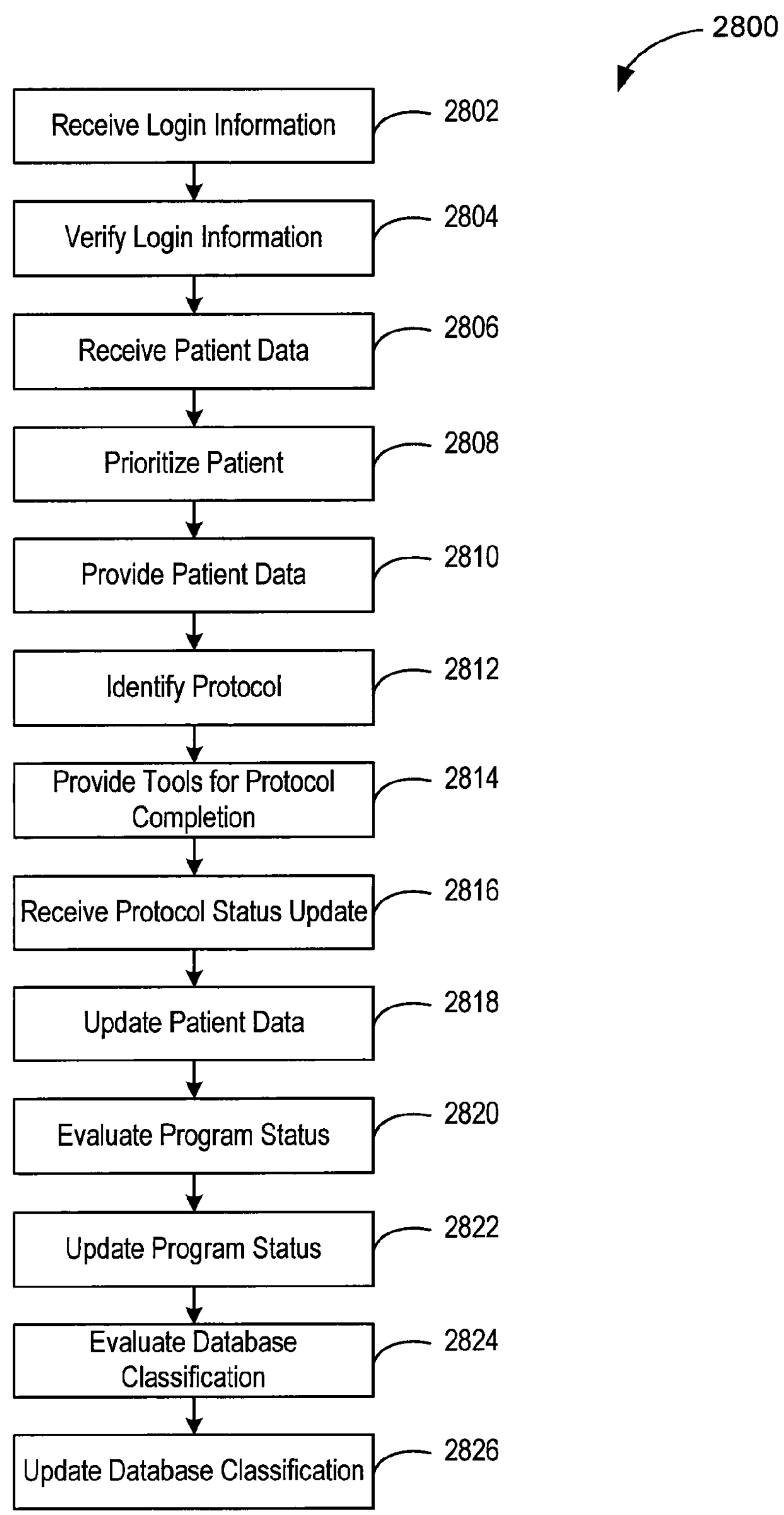
FIG. 28 is a flowchart illustrating one embodiment of a process for providing program services.

With reference now to FIG. 28, a flowchart illustrating one embodiment of a process 2800 for providing program services is shown. The process 2800 for providing program services can be performed with one of the user devices 118, and specifically with the nurse navigator 1700. In some embodiments, the process 2800 for providing program services can include receiving triggered patient data, prioritizing the patients and/or patients associated with the patient data, providing protocol information for the program and/or programs identified in the patient data, and receiving a protocol into a program status update.

Process 2800 begins at block 2802 wherein the user login information is received. In some embodiments, for example, the user login information can identify the user. User login information can include any information that identifies the user such as, for example, a username and password, an employee or other identification number, or biometric information. In some embodiments, the user login information can be received by a component of the program optimization system 100 including, for example, one of the user devices 118 such as the nurse navigator 1700. In one embodiment, for example, the login information can be received by the input module 1706 of the nurse navigator 1700.

After the user login information is received, the process 2800 proceeds to block 2804 wherein the login information is verified. In some embodiments, for example, the login information can be verified by comparing the received login information to information stored in the access database 116 of the program optimization system 100. In the event that the login information is verified, the user submitting the login information can be identified and granted access. In some embodiments of the verification of login information, the identification of the user, and the granting of access can also be accompanied by the updating of the access database 116 to track the user access to the program optimization system 100.

In some embodiments, the verification of login information can further include the identification of security information associated with the user such as, for example, an access level. In some embodiments, for example, the access level of a user can determine the amount of patient data and/or other data within the program optimization system 100 that the user can access. In some embodiments, the access level of the user can be determined based on the duties of the user and the information used by the user in fulfilling those duties. Thus, for example, in embodiments in which a user's duties are unrelated to a patient's personal information such as, for example the patient's contact information, the patient's billing information, the patient's name, or social security number, the user access level can indicate that the user does not have access to this information.

After the login information has been verified, the process proceeds to block 2806 wherein the patient data is received. In some embodiments, for example, the patient data can be received from the patient database 104, and can comprise triggered patient data. In some embodiments, for example, the triggered patient data can identify a patient, identify the one or more programs into which the patient has been admitted, and/or provide medical information relating to the patient and/or the patient's admission into the one or more programs.

In some embodiments, for example, the triggered patient data can include an indicator of the patient's progress towards completion of the program. In some embodiments, the nurse navigator 1700 can identify the patient's progress towards completion of the program when the patient data is received. In some embodiments, the nurse navigator 1700 can assign the patient data to one of the databases in the memory 1710 of the nurse navigator 1700 according to the patient's progress towards completion of the program.

In some embodiments, after receiving the patient data, the nurse navigator 1700 can use the above identified access level to determine the amount of patient data to which the user has access. In some embodiments, the nurse navigator 1700 can provide the user with an indication of the access level and the patient data that the user is allowed to access and/or the patient data that the user is prohibited from accessing. In some embodiments, the nurse navigator 1700 can use the user access level to filter the patient data to thereby restrict the user's access to only the allowed patient data.

After the patient data is received, the process 2800 proceeds to block 2808 wherein the one or more patients associated with the patient data are prioritized. In some embodiments, for example, the one or more patients associated with the patient data can be prioritized by the processor 1702 of the nurse navigator 1700. In some embodiments in which patient data identifying a plurality of patients is received, the prioritization of the patients can, for example, include the relative prioritization of the patients with respect to each other, and in some embodiments in which patient data identifying a patient admitted into a plurality of programs is received, the prioritization of the patient can include, for example, the relative prioritization of the programs into which the patient has been admitted.

In some embodiments the one or more patients can be prioritized by identifying one or several indicators of the prioritization of the one or more patients in the patient data. In some embodiments the one or more patients can be prioritized, for example, by comparing the received patient data to trigger condition data including prioritization information. These prioritizations can be performed, for example, by the processor 1702 of the nurse navigator 1700.

After the one or more patients have been prioritized, the process 2800 proceeds to block 2810 wherein the patient data is provided to the user. In some embodiments, for example, patient data can be provided to the user via the output module 1704, and can in some embodiments, be displayed on a screen. The patient data can be provided to the user in a variety of formats and organized in a variety of ways. In some embodiments, for example, the patient data can be provided to the user in the form of a listing of patients, which listing can be according to the determined priority. In some embodiments, the patient data can be provided to the user in the form of a listing of programs and the patients associated with the program, which listing of programs can be according to the determined priority.

In some embodiments, for example, the patient data for a single patient can be provided to the user. This patient data can, for example, be selected by the nurse navigator 1700 based on the prioritization of the one or more patients, be selected by an input provided by user, or be selected in any other desired fashion.

After the patient data is provided, the process 2800 proceeds to block 2812 wherein the program service protocol associated with the patient in the program and to which the patient has been admitted is identified. In some embodiments, for example, the identification of the program service protocol associated with the patient can include querying the active database 1714 for the program service protocols associated with one or several programs and receiving program service protocols associated with one or several programs. In some embodiments, for example, the identification of the program service protocol can include providing the program service protocol and/or protocols to the user. In some embodiments, the program service protocol and/or protocols can be provided to the user via the output module 1704 of the nurse navigator 1700, and can, for example be provided to the user by being displayed on the screen.

In some embodiments, and as discussed above, the program service protocols can correspond to action items and or tasks leading to the completion of the program. In one specific embodiment, for example, the program service protocols can include the scheduling or confirmation of an appointment and/or treatment, the tracking of the status of the appointment and/or treatment, and/or following up on the completion of the appointment and/or treatment. In one embodiment, the one or several program service protocols can be based on some aspect of the patient data, including, for example, the patient's condition, the patient's treatment status, including the patient's status as either inpatient or outpatient, whether the patient already has and/or is receiving, or will receive care from a primary care physician and/or a specialist such as a cardiologist, or any other aspect of the patient data.

After the program service protocol and/or protocols have been identified, the process 2800 proceeds to block 2814 wherein tools for protocol completion are provided. In some embodiments, for example, the tools for protocol completion can include the information necessary to complete a protocol. By way of example, in one embodiment in which scheduling of an appointment is requested to complete the program service protocol, the tool for protocol completion can include, for example, access to information regarding patient availability, access to information regarding medical resource availability, and information and/or features configured to facilitate sending information to and receiving information from the patient and the medical resource.

In one embodiment in which the tool for protocol completion comprises access to information regarding the patient's availability, patient database 104 can include patient availability information. This information can include, for example, general availability information for the patient such as, for example, a preference for certain times of the day, certain days of the week, certain parts of the month, and/or certain seasons and/or months of the year. In some embodiments, for example the patient availability information can be specific and can include, for example, patient availability indicated in dates and times. In some embodiments, this patient availability information can be collected by a medical service provider and input into the program optimization system 100 via the nurse navigator 1700 and/or other user devices 118, and in some embodiments, this patient availability information can be input into the program optimization system 100 via one of the user devices 118 by the patient.

In one embodiment in which the tool for program service protocol completion comprises access to information regarding medical resource availability, the schedule database 108 can include information relating to the medical resources. Specifically, in some embodiments, for example, the information regarding medical resources can include an indication of the capability of the medical resource, the nature of medical resource, the location of medical resource, and/or any other information useful in determining the suitability of the medical resource for specific purpose. This information can be used to select and/or assist in selecting an ideal medical resource for program service protocol. In some embodiments, the selection of an ideal medical resource can include determining whether the medical resource is located within a designated distance of the patient. This designated distance can, for example, be patient specific or patient generic. In some embodiments, the selection of an ideal medical resource can include determining whether the medical resource is capable of performing the services associated with the program service protocol. In some embodiments, the selection of an ideal medical resource can include determining whether the patient can be scheduled for an appointment within a designated timeframe, which timeframe can be based on the prioritization of the patient.

In one embodiment, the tool for program service protocol completion can provide data to facilitate sending information to and receiving information from the patient and/or medical resource. In some embodiments, for example, this data can comprise contact information for the patient and/or for the medical resource such as, for example, telephone number, mailing address, and email address, or any other desired contact information. In one embodiment, the tool for program service protocol completion can provide one or several features to facilitate sending information to and/or receiving information from the patient and/or the medical service provider. In some embodiments, for example, the one or several features can include an application configured to access the calendar and/or schedule for the patient and/or for the medical resource. Thus, in some embodiments, the user can directly access the calendar and/or schedule of the patient and/or medical resource to schedule an appointment for the patient.

After tools for the program service protocol completion are provided, the process 2800 proceeds to block 2816 wherein a program service protocol status update is received. In some embodiments, for example, the program service protocol status update can include information indicating the completion of a program service protocol or the non-completion of the program service protocol. In some embodiments, this status update can be received from one of the user devices 118 and can be specifically received, for example, from the input module 1706 of the nurse navigator 1700. In some embodiments in which the medical resource is directly linked to the program optimization system 100, the status update can be received directly from the medical research. Thus, in such an embodiment, an indication that the patient has attended a scheduled appointment can be received directly from the medical resource after the patient has attended the scheduled appointment.

In some embodiments in which the program service protocol status update indicates that the program service protocol has not been completed, the user can be provided with a follow-up protocol. The follow-up protocol can be stored in the program database 110 and can be retrieved by the user device 118, and specifically by the nurse navigator 1700 to facilitate follow-up. In some embodiments, for example, the follow-up protocol can include instructions to determine if the program service protocol is still progressing towards completion or if remedial action can be taken to help progress the program service protocol towards completion. In some embodiments, this can include, contacting the patient to verify availability for coming appointment, contact the patient to determine why an appointment was missed and/or to reschedule an appointment, and/or contact medical resource to verify the availability and confirm the appointment. If it is determined that remedial action can be taken to help progress the program service protocol towards completion, the follow-up protocol can include instructions and/or action items corresponding to that remedial action.

After the program service protocol status update has been received, the process 2800 proceeds to block 2818 wherein the patient data is updated. In some embodiments, the patient data can be updated to reflect the status update of the program service protocol. This update to the patient data can be made in, for example, the patient database 104, the schedule database 108, the administrator database 112, processing database 1716, the compliance database 1718, the completed database 1720, the archive database 1722, the excluded database 1724 and/or the tracking database 1726.

After the patient data has been updated, the process 2800 proceeds to block 2820 wherein the program status is evaluated. In some embodiments, for example, the program status can be evaluated to determine whether the patient has completed the program. In some embodiments, the program status can be evaluated as described in blocks 1912 through 1934 of FIG. 19 and the therewith associated text.

After the program status has been evaluated, the process 2800 proceeds to block 2822, wherein the program status is updated. In some embodiments, for example, the program status can be updated in the patient data. In some embodiments, the updated patient data and/or the update program status can be stored in, for example, the patient database 104, the schedule database 108, the administrator database 112, processing database 1716, the compliance database 1718, the completed database 1720, the archive database 1722, the excluded database 1724 and/or the tracking database 1726.

After the program status as been updated, the process 2800 proceeds to block 2824 wherein the database classification of the patient is evaluated. In some embodiments, for example, the evaluation of the database classification of the patient can include identifying the current classification of the patient regarding the databases 1712 to 1726 of the nurse navigator 1700, determining the proper database classification of the patient based on a comparison of the current patient program status to the criteria for inclusion in the databases 1712 to 1726 of the nurse navigator 1700, and comparing the proper database classification of the patient with the current classification of the patient. In some embodiments, for example, an indicator can be added to the patient data indicating the current patient database classification in the proper database classification.

After the patient database classification has been evaluated, the process 2800 proceeds to block 2826 wherein the database classification is updated. In some embodiments, for example, the update of the database classification can include retrieving the indicator of the proper database classification from the patient data, identifying the proper database classification based on the indicator, and placing the patient data in the identified proper database.

Figure 29:
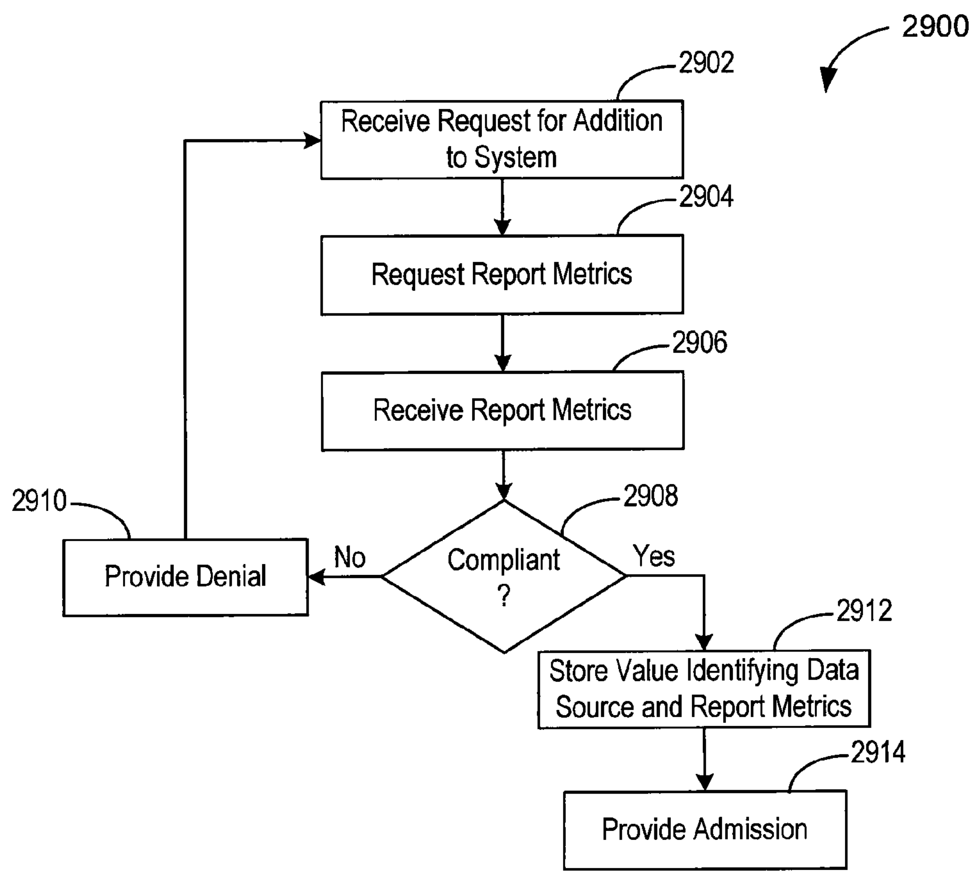
FIG. 29 is a flowchart illustrating one embodiment of a process for determining the admissibility of a data source to the program optimization system.

With reference now to FIG. 29, a flowchart illustrating one embodiment of a process 2900 for determining the admissibility of a data source to the program optimization system 100 is shown. In some embodiments, the process 2900 can be used to admit a new patient data source 102 into the program optimization system 100. The process 2900 can begin at block 2902 where request for the addition of a patient data source 102 to the program optimization system 100 is received. In some embodiments, this request can be received by a component of the program optimization system 100 including, for example, the processor 120.

After the request for addition of the patient data source 102 to the program optimization system 100 has been received, the process 2900 proceeds to block 2904 wherein report metrics are requested from the patient data source 102. In some embodiments, the report metrics can identify information relating to the data source 102 such as, for example, the type of the data source, the result of the data source which can include, for example, the clinical result of the data source, and/or information relating to the clinical result of the data source. In some embodiments, the information relating to the clinical result of the data source can include, for example, information relating to the format of the clinical result and/or the units or methods of expression of the clinical result. In some embodiments, the request for report metrics can be made by the processor 120 and/or another component of program optimization system 100.

After the report metrics have been requested, the process 2900 proceeds to block 2906 wherein report metrics are received. In some embodiments, the report metrics can be received directly from the patient data source 102 via communication between the patient data source 102 and other components of the program optimization system 100, and in some embodiments, the report metrics can be received indirectly from the patient data source 102 such as, for example, via human interaction with the program optimization system 100 to enter and/or provide the report metrics.

After the report metrics have been received, the process 2900 proceeds to decision state 2908 wherein it is determined if the received report metrics comply with requirements and/or parameters of the program optimization system 100. In some embodiments, this determination can include determining whether the type of clinical result generated by the patient data source 102, the format of the clinical result, the content of the clinical result, and/or the units used in expressing the clinical result comply with standards, parameters, and/or requirements of the program optimization system. In some embodiments, this determination can be made by the processor 120 and can include the evaluation of the received report metrics.

If it is determined that the report metrics are not compliant with the requirements, standards, and/or parameters of the program optimization system 100, then the process 2900 proceeds to block 2910 wherein a denial is provided. In some embodiments, the denial can be provided directly to the patient data source 102 and/or can be indirectly provided to the patient data source 102 via, for example, a human interfacing with the program optimization system 100. In some embodiments, the denial can further include information relating to how the patient data source 102 can be brought into compliance with the standards, parameters, and/or requirements of the program optimization system 100.

Returning again to decision state 2908, if it is determined that the report metrics are compliant with the requirements, standards, and/or parameters of the program optimization system 100, then the process 2900 proceeds to block 2912 wherein a value identifying the data source and/or the report metrics associated with the data source is stored in the patient database 104 and/or in one of the program databases 105 such as, for example, the administration database 112 and/or the access database 116.

After value identifying the patient data source 102 and/or the report metrics associated with the patient data source 102 has been stored, the process 2900 proceeds to block 2914 wherein admission to the program optimization system 100 is provided to the patient data source 102. In some embodiments, the admission of the patient data source 102 into the program optimization system 100 can be provided directly to the patient data source 102 and/or can be indirectly provided to the patient data source 102 via, for example, a human interfacing with the program optimization system 100. In some embodiments, the admission can include request for one or several clinical results generated by the patient data source 102 for previous patients.

Figure 30:
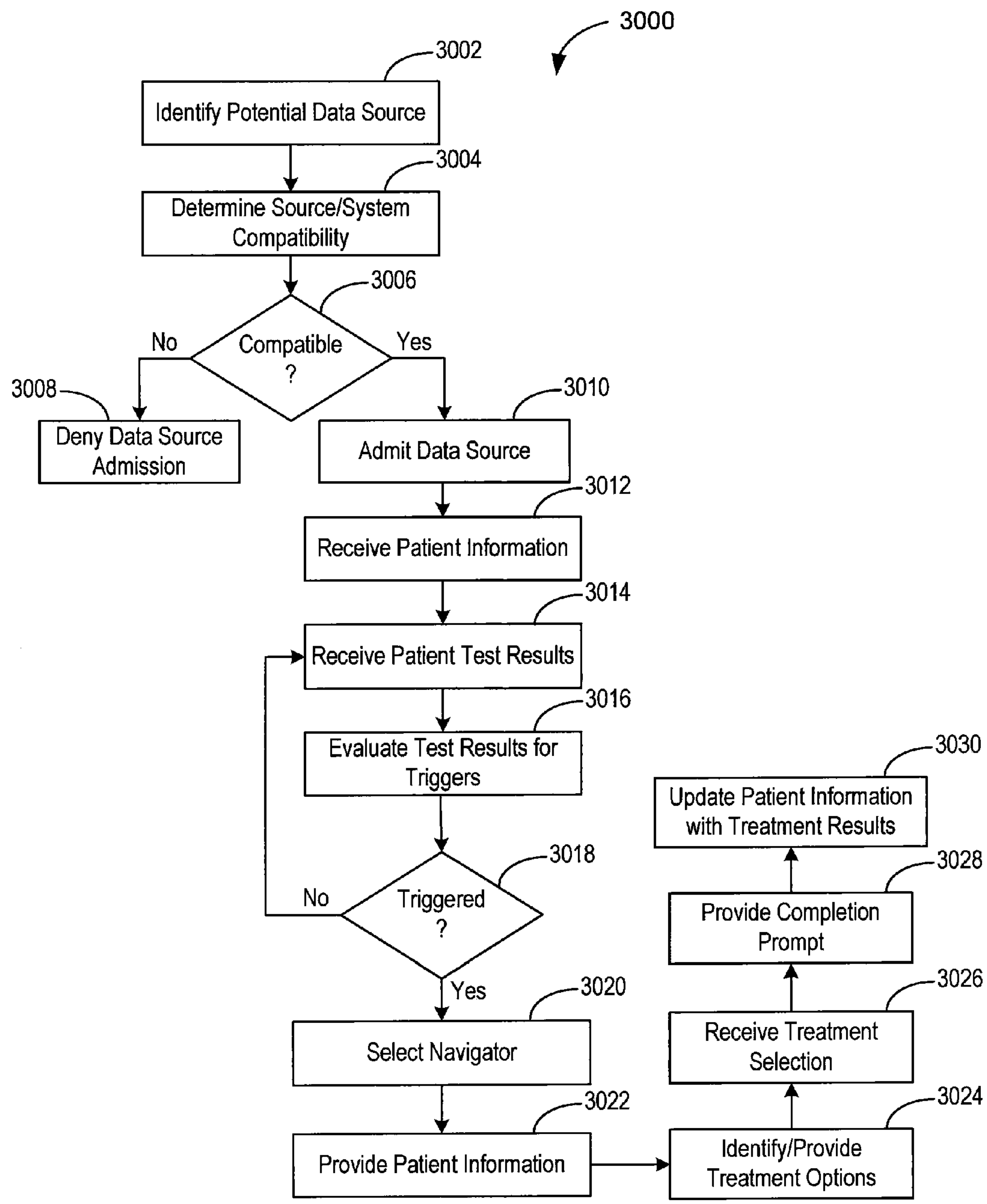
FIG. 30 is a flowchart illustrating one embodiment of a process for the operation of the program optimization system.

With reference now to FIG. 30, a flowchart illustrating one embodiment of a process 3000 for the operation of the program optimization system 100 is shown. In some embodiments, the process 3000 can be performed by one or several of the components of the program optimization system 100. The process can begin at block 3002 wherein a potential patient data source 102 is identified. In one embodiment, the potential patient data source 102 can be identified via request from the potential patient data source 102 for admission to the program optimization system 100. After the potential data source has been identified, the process 3000 proceeds to block 3004 wherein the compatibility of the patient data source 102 and the program optimization system 102 is determined. In some embodiments, this can include the steps discussed above with respect to process 2900.

After the compatibility of the patient data source 102 and the program optimization system 100 has been determined, the process 3000 proceeds to decision state 3006 wherein data sources 102 that are compatible with the program optimization system 100 are separated from patient data sources 102 that are not compatible with program optimization system 100. If it is determined that the patient data source 102 at question is not compatible with program optimization system 100, then the process 3000 proceeds block 3008 wherein data source admission to the program optimization system 100 is denied.

Returning again to decision state 3006, if it is determined that the patient data source 102 is compatible with the program optimization system 100, the process 3000 proceeds to block 3010 wherein the patient data source 102 is admitted into the program optimization system 100. After the patient data source 102 has been admitted into the program optimization system 100, the process 3000 proceeds to block 3012 wherein patient information is received. In some embodiments, patient information can be received from the patient database 104, and in some embodiments, patient information relevant to a specific patient can be selected from the patient database 104. The selection of patient data from the patient database 104 can be performed in a variety of fashions and can include, for example, selecting patient data that has been newly added to the patient database 104 and/or selecting patient data based on provided and/or anticipated medical services.

After the patient information has been received, the process 3000 proceeds to block 3014 wherein a patient test result and/or a plurality of patient test results are received. In some embodiments, these test results, also referred to herein as clinical results, can be generated by one or several of the patient data sources 102 of the program optimization system 100. After the patient test results have been received, the process 3000 proceeds block 3016 wherein the patient test results are evaluated for one or several trigger conditions. In some embodiments, the evaluation of the clinical results for one or several trigger conditions can include determining the applicability of one or several trigger values to the clinical results, comparing one or several trigger values to the clinical results, and generating a trigger result based on the comparison of the one or several trigger values to the clinical results and/or to one or several aspects of the clinical results.

After the clinical results have been evaluated for trigger conditions, the process 3000 proceeds to block 3018 wherein it is determined if any of the trigger conditions exist within the clinical result. In some embodiments, the existence of a trigger condition within the clinical results is also referred to as a trigger event or a triggering event. If it is determined that the clinical result does not include a trigger event, the process 3000 returns to block 3014 and proceeds as outlined above.

If it is determined that the clinical result includes a trigger event, then the process 3000 proceeds to block 3020 wherein a navigator is selected. In some embodiments, the navigator can be selected by the processor 120 and/or another component of the program optimization system 100. The navigator can be a person that uses components of the program optimization system 100, such as one or several of the user devices 118, to facilitate and/or manage the treatment or providing of care to a patient and/or member of a healthcare organization. In some embodiments, the navigator can be selected from a list of navigators stored in one of the program databases 105 such as, for example, the administrator database 112. In some embodiments, the navigator is selected based on location of the navigator and/or the location of the patient, based on the clinical result, the data source, the trigger result, or the like. In one embodiment, for example, the navigator is selected based on the location of the patient, a personal preference of the patient including, for example, a preference for working with male and/or female medical care providers, the trigger result of the patient and/or patient treatment options.

After the navigator has been selected, the process 3000 proceeds to block 3022 wherein patient information is provided. In some embodiments, the patient information can be provided to the navigator via a component of the program optimization system 100 such as one or several of the user devices 118. In some embodiments, the information that can be provided to the navigator can include, for example, all or portions of the medical history of the patient, the clinical result, the trigger result, information relating to the patient's admission process, and/or any other information relating to the patient including, for example, physician notes and/or notes from another medical service provider.

After the patient information has been provided, the process 3000 proceeds to block 3024 wherein treatment options are identified and/or provided. In some embodiments, this can include querying one of the patient databases 104 such as, for example, the program database 110 for one or several treatment options associated with the trigger result. The treatment options can be any intervention or interaction by a medical service provider with the patient, and can include for example, a telephone call, an appointment, a test, a procedure, or the like. After one or several treatment options have been provided, the process 3000 proceeds to block 3026 wherein a treatment selection is received. In some embodiments, the treatment selection can be received by a component of the program optimization system 100 and can be received from the navigator and/or a physician.

After the treatment selection has been received, the process 3000 proceeds to block 3028 wherein a completion prompt is provided. In some embodiments, the completion prompt can be an indicator provided to the navigator to perform an act associated with the selected treatment. In some embodiments, the completion prompt can be provided to the navigator via one or several of the user devices 118.

After the completion prompt has been provided, the process 3000 proceeds to block 3030 wherein patient information is updated with the treatment results. In some embodiments, the patient information can be updated based on actions included in the treatment that have been completed, partially completed, and/or that have not been completed and/or based on the completion, partial completion, and/or incompletion of the treatment. In some embodiments, this patient data can be updated in one of the databases such as, for example, the patient database 104.

Figure 31:
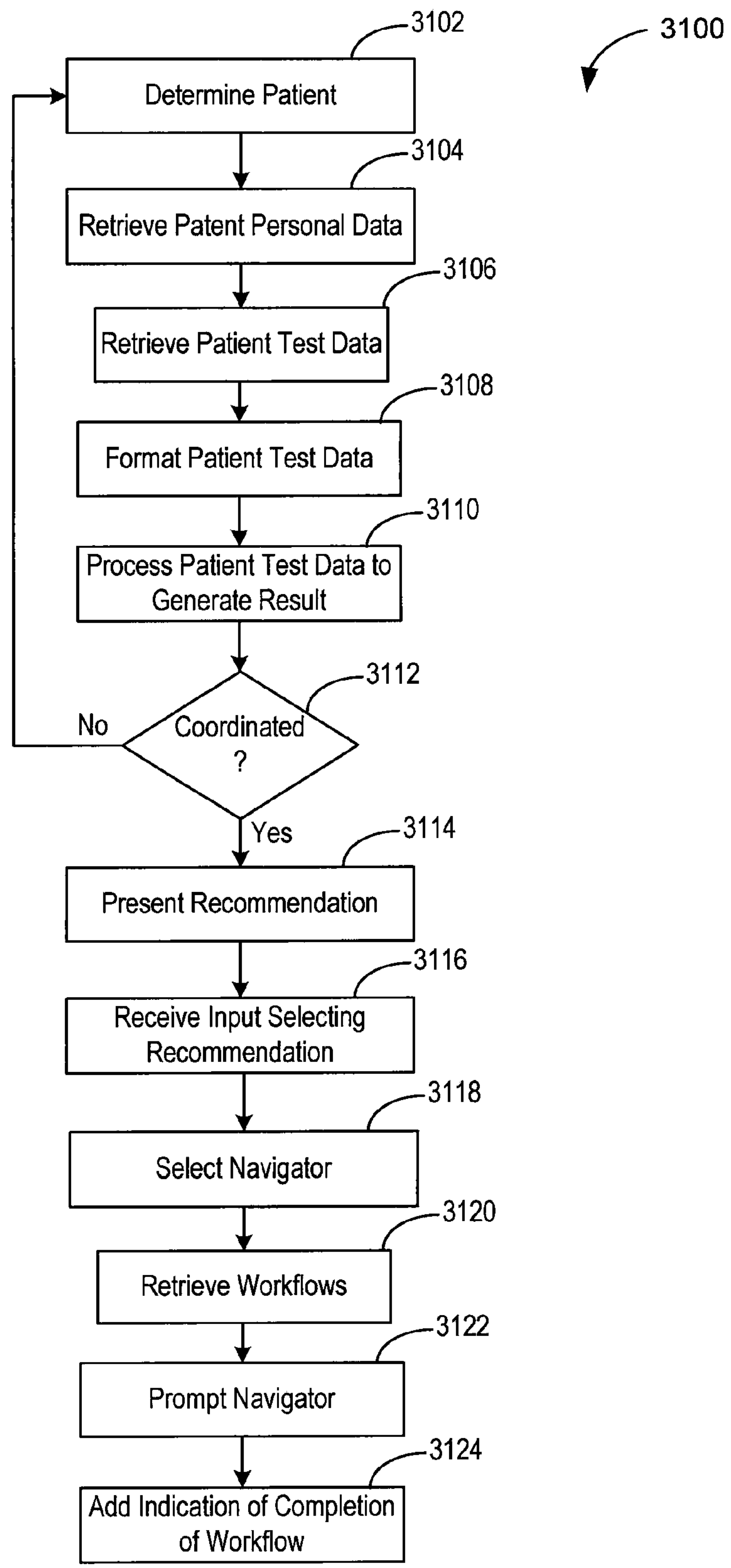
FIG. 31 is a flowchart illustrating one embodiment of an alternative process for the operation of the program optimization system.

With reference now to FIG. 31, a flowchart illustrating one embodiment of an alternative process 3100 for the operation of the program optimization system 100 is shown. In some embodiments, the process 3100 can be performed by a component of the program optimization system 100. The process 3100 begins at block 3102, wherein the patient is determined. In some embodiments, the determination of the patient can be performed by a component of program optimization system 100 including, for example, the processor 120. In some embodiments, the patient can be determined by selecting a patient from the patient data stored in the patient database 104. In some embodiments, the patient can be selected according to an algorithm in which patients are prioritized for selection based on, for example, whether a medical service was recently received, whether a patient was recently added into program optimization system 100, and/or the severity of existing patient condition or conditions recorded in patient medical history.

After the patient has been determined, the process 3100 proceeds to block 3104 wherein patient personal data is retrieved. In some embodiments, the patient personal data can be retrieved from the patient database 104. The patient personal data can include information identifying the patient and information relating to the patient's medical history. After the patient personal data has been retrieved, the process 3100 proceeds to block 3106 wherein patient test data is retrieved. In some embodiments, the patient test data can be data that has been generated by one or several of the patient data sources 102 and that has not yet been entered into patient database 104. In some embodiments, the retrieval of the patient test data can include the generation of a local copy of the patient data at the patient data source 102, and storage of the test data in, for example, the patient database 104.

After the patient test data has been retrieved, the process 3100 proceeds to block 3108 wherein the patient test data is formatted. In some embodiments, for example, patient test data may be in an undesirable format and/or may use undesirable units. In such an embodiment, the processor can be configured to retrieve the patient test data, identify the format and/or the units used in the patient test data and reformat the patient test data and/or adjust units in the patient test data so that the format and/or units of the patient test data are compatible with the program optimization system 100. This formatting and/or unit conversion of the patient test data can be performed by a component of the program optimization system 100 including, for example, the processor 120.

After the patient test data has been formatted, the process 3100 proceeds to block 3110 wherein the patient test data is processed to generate a result, and specifically to generate a trigger result. In some embodiments, and as discussed at greater length above, the patient test data can be evaluated for one or several trigger events. These trigger events can be selected for comparison to patient test data based on aspects of the patient test data such as, for example, the categorization of the patient test data. In one embodiment, for example, the patient test data can be evaluated to determine the categorization of the patient test data, which categorization can be associated with one or several trigger values. The one or several trigger values can then be compared to the patient test data to determine if the patient test data includes a trigger event. If the patient test data includes a trigger event, a value, referred to herein as a trigger result, can be generated. In some embodiments, the trigger result can indicate the existence of a trigger event and/or provide information relating to the trigger event such as, for example, the degree to which the data representing the trigger event exceeds the trigger value.

After the patient test data has been processed to generate a result, the process 3100 proceeds to decision state 3112 wherein it is determined whether to provide coordinated care for the patient. In some embodiments, the determination of whether to provide coordinated care can include determining whether to assign a navigator and/or select a navigator for the patient. In some embodiments, this determination can be made based on aspects of the patient data such as, for example, the magnitude of any existing patient health problems, the magnitude of the trigger event, and/or the like. If it is determined that coordinated patient care will not be provided, then the process 3100 returns to block 3102 and proceeds as outlined above.

If it is determined that coordinated patient care will be provided, then the process 3100 proceeds to block 3114 wherein a treatment recommendation is provided. In some embodiments, the treatment recommendation can comprise one or several potential diagnoses and/or one or several treatments. In some embodiments, the recommendation can be provided to a navigator and/or a physician. The recommendation can be provided by a component of the program optimization system 100 such as, for example, one or several of the user devices 118.

After the treatment recommendation has been presented, the process 3100 proceeds to block 3116 wherein an input selecting a treatment recommendation is received. In some embodiments, the input selecting a treatment recommendation can be received via a component of the program optimization system 100 such as, for example, one or several of the user devices 118. After an input selecting the treatment recommendation has been received, the process 3100 proceeds to block 3118 wherein a navigator is selected. In some embodiments, the navigator can be selected by the processor 120 and/or another component of the program optimization system 100. In some embodiments, the navigator can be a person that uses components of the program optimization system 100, such as one or several of the user devices 118, to facilitate and/or manage the treatment or the providing of care to a patient and/or member of a healthcare organization. In some embodiments, the navigator can be selected from a list of navigators stored in one of the program databases 105 such as, for example, the administrator database 112. In some embodiments, the navigator can be selected based on the location of the navigator and/or the location of the patient, based on the clinical result, the data source, the trigger result, or the like. In one embodiment, for example, the navigator can be selected based on location of the patient, a personal preference of the patient including, for example, a preference for working with male and/or female medical care providers, the trigger result of the patient, and/or patient treatment options.

After the navigator has been selected, the process 3100 proceeds to block 3120 wherein one or several workflows associated with the selected recommendation are retrieved. In some embodiments, this can include querying one of the patient databases 104 such as, for example, the protocol database for one or several treatment plans associated with the selected recommendation. In some embodiments, the one or several treatment plans can be grouped into one or several workflows that can outline one or several actions that together can form one or several treatment plans. In some embodiments, the one or several actions can include actions to be performed by one or several medical service providers including, for example, the physician and/or the navigator, and/or actions to be performed by the patient. In some embodiments, the actions of the workflow can be organized according to a temporal sequence in which the actions should be performed.

After the workflows have been received, the process 3100 proceeds to block 3122 wherein the navigator is prompted. In some embodiments, the navigator can be prompted via one of the user devices 118. In some embodiments, the navigator can be prompted to perform an action and/or to follow up on the performance of one of the actions of the workflow. In some embodiments, and in response to the prompt, the navigator can input an indicator of the status of the action for which the navigator received a prompt. In some embodiments, for example, the navigator can input an indicator of the completion of the action and/or workflow, the incompletion of the action and/or workflow, and/or the partial completion of the action and/or workflow, and in some embodiments, the navigator can provide information relating to the details of the completion of the action. After the navigator has been prompted, the process 3100 proceeds block 3124 wherein an indication of the status of the action and/or the status of the workflow is associated with the patient. In some embodiments, for example, in which the navigator inputs an indicator of the status of the action and/or status of the workflow, the patient data can be updated to reflect the status of the action and/or of the workflow. In some embodiments, this update can be stored within the patient database 104.

Figure 32:
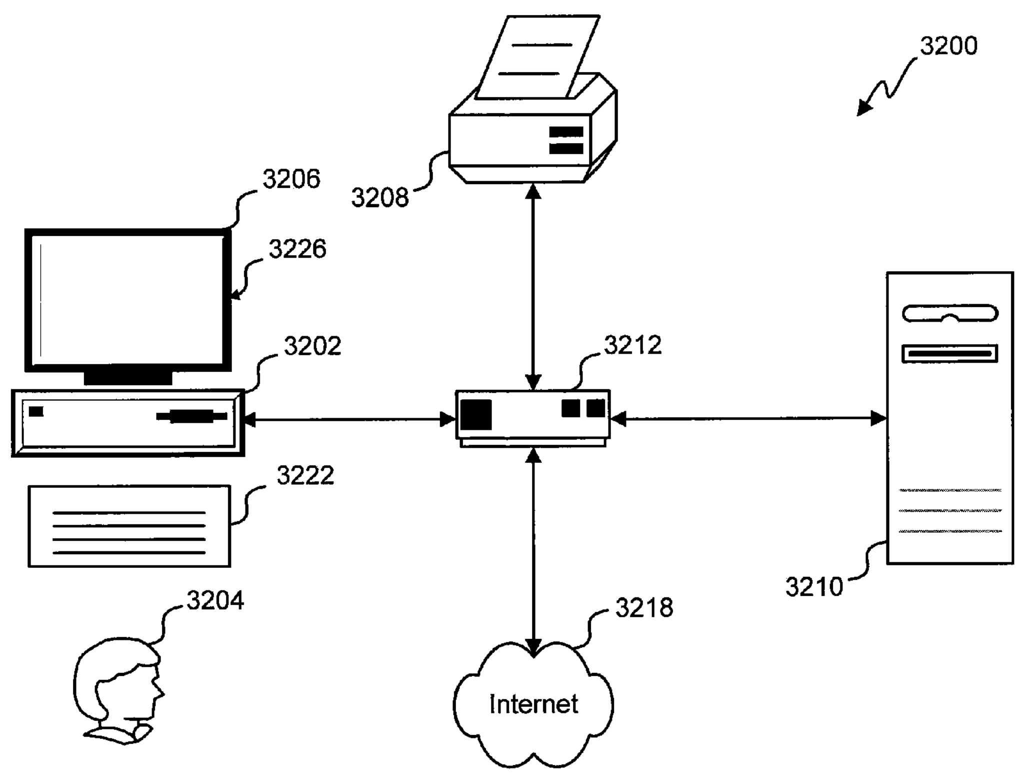
FIG. 32 is a schematic illustration of an exemplary computer system with which embodiments of the present disclosure may be implemented.

With reference now to FIG. 32, an exemplary environment with which embodiments may be implemented is shown with a computer system 3200 that can be used by a user 3204 as all or a component of a program optimization system 100. The computer system 3200 can include a computer 3202, a keyboard 3222, a network router 3212, a printer 3208, and a monitor 3206. The monitor 3206, computer 3202 and keyboard 3222 are part of a computer system 3226, which can be a laptop computer, desktop computer, handheld computer, mainframe computer, etc. The monitor 3206 can be a CRT, flat screen, etc.

A user 3204 can input commands into the computer 3202 using various input devices, such as a mouse, a keyboard 3222, track ball, touch screen, etc. If the computer system 3200 comprises a mainframe, a user 3204 can access the computer 3202 using, for example, a terminal or terminal interface. Additionally, the computer system 3226 may be connected to a printer 3208 and a server 3210 using a network router 3212, which may connect to the Internet 3218 or a WAN.

The server 3210 may, for example, be used to store additional software programs and data. In one embodiment, software implementing the systems and methods described herein can be stored on a storage medium in the server 3210. Thus, the software can be run from the storage medium in the server 3210. In another embodiment, software implementing the systems and methods described herein can be stored on a storage medium in the computer 3202. Thus, the software can be run from the storage medium in the computer system 3226. Therefore, in this embodiment, the software can be used whether or not computer 3202 is connected to network router 3212. Printer 3208 may be connected directly to computer 3202, in which case, the computer system 3226 can print whether or not it is connected to network router 3212.

Figure 33:
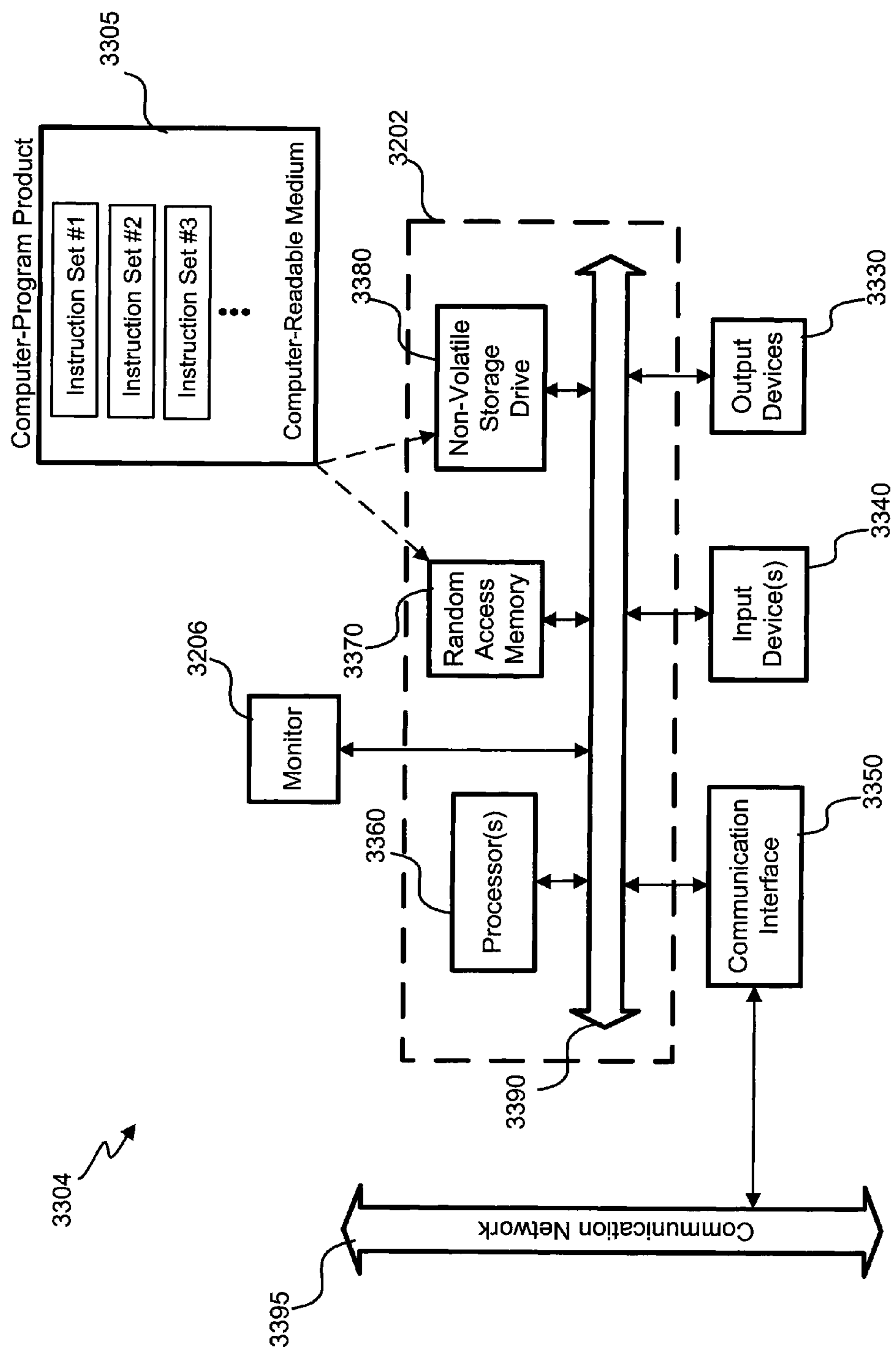
FIG. 33 is a schematic illustration of an exemplary special purpose computer system.

With reference to FIG. 33, an embodiment of a special-purpose computer system 3304 is shown. The above methods may be implemented by computer-program products that direct a computer system to perform the actions of the above-described methods and components. Each such computer-program product may comprise sets of instructions (codes) embodied on a computer-readable medium that directs the processor of a computer system to perform corresponding actions. The instructions may be configured to run in sequential order, or in parallel (such as under different processing threads), or in a combination thereof. After loading the computer-program products on a general purpose computer system 3226, it is transformed into the special-purpose computer system 3304.

Special-purpose computer system 3304 comprises a computer 3202, a monitor 3206 coupled to computer 3202, one or more additional user output devices 3330 (optional) coupled to computer 3202, one or more user input devices 3340 (e.g., keyboard, mouse, track ball, touch screen) coupled to computer 3202, an optional communications interface 3350 coupled to computer 3202, a computer-program product 3305 stored in a tangible computer-readable memory in computer 3202. Computer-program product 3305 directs special-purpose computer system 3304 to perform the above-described methods. Computer 3202 may include one or more processors 3360 that communicate with a number of peripheral devices via a bus subsystem 3390. These peripheral devices may include user output device(s) 3330, user input device(s) 3340, communications interface 3350, and a storage subsystem, such as random access memory (RAM) 3370 and non-volatile storage drive 3380 (e.g., disk drive, optical drive, solid state drive), which are forms of tangible computer-readable memory.

Computer-program product 3305 may be stored in non-volatile storage drive 3380 or another computer-readable medium accessible to computer 3202 and loaded into RAM 3370. Each processor 3360 may comprise a microprocessor, such as a microprocessor from Intel® or Advanced Micro Devices, Inc.®, or the like. To support computer-program product 3305, the computer 3202 runs an operating system that handles the communications of computer-program product 3305 with the above-noted components, as well as the communications between the above-noted components in support of the computer-program product 3305. Exemplary operating systems include Windows® or the like from Microsoft® Corporation, Solaris® from Oracle®, LINUX, UNIX, and the like.

User input devices 3340 include all possible types of devices and mechanisms to input information to computer system 3202. These may include a keyboard, a keypad, a mouse, a scanner, a digital drawing pad, a touch screen incorporated into the display, audio input devices such as voice recognition systems, microphones, and other types of input devices. In various embodiments, user input devices 3340 are typically embodied as a computer mouse, a trackball, a track pad, a joystick, wireless remote, a drawing tablet, a voice command system. User input devices 3340 typically allow a user to select objects, icons, text and the like that appear on the monitor 3206 via a command such as a click of a button or the like. User output devices 3330 include all possible types of devices and mechanisms to output information from computer 3202. These may include a display (e.g., monitor 3206), printers, non-visual displays such as audio output devices, etc.

Communications interface 3350 provides an interface to other communication networks 3395 and devices and may serve as an interface to receive data from and transmit data to other systems, WANs and/or the Internet 3218. Embodiments of communications interface 3350 typically include an Ethernet card, a modem (telephone, satellite, cable, ISDN), a (asynchronous) digital subscriber line (DSL) unit, a FireWire® interface, a USB® interface, a wireless network adapter, and the like. For example, communications interface 3350 may be coupled to a computer network, to a FireWire® bus, or the like. In other embodiments, communications interface 3350 may be physically integrated on the motherboard of computer 3202, and/or may be a software program, or the like.

RAM 3370 and non-volatile storage drive 3380 are examples of tangible computer-readable media configured to store data such as computer-program product 3305 embodiments of the present invention, including executable computer code, human-readable code, or the like. Other types of tangible computer-readable media include floppy disks, removable hard disks, optical storage media such as CD-ROMs, DVDs, bar codes, semiconductor memories such as flash memories, read-only-memories (ROMs), battery-backed volatile memories, networked storage devices, and the like. RAM 3370 and non-volatile storage drive 3380 may be configured to store the basic programming and data constructs that provide the functionality of various embodiments of the present invention, as described above.

Software instruction sets that provide the functionality of the present invention may be stored in RAM 3370 and non-volatile storage drive 3380. These instruction sets or code may be executed by the processor(s) 3360. RAM 3370 and non-volatile storage drive 3380 may also provide a repository to store data and data structures used in accordance with the present invention. RAM 3370 and non-volatile storage drive 3380 may include a number of memories including a main random access memory (RAM) to store instructions and data during program execution and a read-only memory (ROM) in which fixed instructions are stored. RAM 3370 and non-volatile storage drive 3380 may include a file storage subsystem providing persistent (non-volatile) storage of program and/or data files. RAM 3370 and non-volatile storage drive 3380 may also include removable storage systems, such as removable flash memory.

Bus subsystem 3390 provides a mechanism to allow the various components and subsystems of computer 3202 to communicate with each other as intended. Although bus subsystem 3390 is shown schematically as a single bus, alternative embodiments of the bus subsystem may utilize multiple busses or communication paths within the computer 3202.

A number of variations and modifications of the disclosed embodiments can also be used. Some additional embodiments are disclosed in the herewith submitted appendix, the entirety of which is incorporated by reference. Specific details are given in the above description to provide a thorough understanding of the embodiments. However, it is understood that the embodiments may be practiced without these specific details. For example, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A computer-implemented method for dynamically selecting navigator devices, the method comprising:

identifying, by a computing device with a processor, a set of data sources that is associated with a program optimization system, wherein the set of data sources includes one or more data sources that store clinical data, and wherein the program optimization system is associated with a defined parameter condition used for determining whether to include additional data sources into the set of data sources;

receiving, by the computing device with the processor, a communication from a first data source not included in the set of data sources, wherein the communication includes:

data representing a request to include the first data source into the set of data sources, and a report metric from the first data source, wherein the report metric identifies a type of the first data source and a result of the first data source;

in response to receiving the communication, automatically determining, by the computing device with the processor, whether the report metric satisfies the defined parameter condition;

including, by the computing device with the processor, the first data source into the set of data sources based on the determination, wherein the inclusion of the first data source into the set of data sources indicates that the report metric satisfies with the defined parameter condition;

accessing, by the computing device with the processor, a database storing patient data, wherein:

the patient data identifies a plurality of patients, the database stores first patient data associated with a first patient and second patient data associated with a second patient, the stored first patient data including a first priority indicator representing a first priority and the second patient data including a second priority indicator representing a second priority, and the first patient data being prioritized over the second patient data based on, at least in part, the first priority indicator and the second priority indicator;

identifying, by the computing device with the processor, a second data source from the set of data stores, wherein the second data source stores clinical data corresponding to one or more types of clinical result;

querying, by the computing device with the processor, the second data source for first clinical result data corresponding to the first patient data and second clinical result data corresponding to the second patient data;

selecting, by the computing device with the processor, a categorization rule in accordance with each of the first clinical result and the second clinical result, wherein:

the categorization rule is associated with a trigger protocol that triggers one or more workflows based on a comparison of the first clinical result or the second clinical result with a threshold, the threshold being determined using the categorization rule;

determining, by the computing device with the processor, that the first clinical result data and the second clinical result data are of the same type of clinical result, the determination being based on the categorization rule;

comparing, by the computing device with the processor, each of the first clinical result data and the second clinical result data with the threshold, wherein:

the comparison results in a first value indicating a difference between the first clinical result data and the threshold, the comparison further results in a second value indicating a difference between the second clinical result data and the threshold, and the first value corresponds to the first priority indicator and the second value corresponds to the second priority indicator;

determining, by the computing device with the processor, that one or more navigator devices are to be selected for performing workflows for each of the first patient data and the second patient data;

selecting, by a computing device with a processor, a first navigator device from a plurality of navigator devices, wherein the selection of the first navigator device includes:

identifying the plurality of navigator devices based on the determination that one or more navigator devices are to be selected for performing workflows, each of the plurality of navigator devices being associated with one or more attributes, determining, for each navigator device of the plurality of navigator devices, whether the associated one or more attributes corresponds to the first value, and selecting the first navigator device when the one or more attributes associated with the first navigator device correspond to the first value;

selecting, by a computing device with a processor, a first workflow protocol from a plurality of workflow protocols, wherein the selection of the first workflow protocol is based on the first value, wherein the first workflow protocol includes first workflow data that represents a plurality of first actions to be performed by the first navigator device for the first patient;

receiving, by a computing device with a processor, a first input indicating completion of at least one of the plurality of first actions, and updating the first patient data with a first indication corresponding to the completion of the at least one plurality of first actions;

selecting, by a computing device with a processor, a second navigator device from the plurality of navigator devices, wherein the selection of the second navigator device includes:

identifying the plurality of navigator devices, determining, for each navigator device of the plurality of navigator devices, whether the associated one or more attributes corresponds to the second value, and selecting the second navigator device when the one or more attributes associated with the second navigator device correspond to the second value, wherein the selected first navigator device is different from the selected second navigator device due to the first value having a different magnitude than the second value;

selecting, by a computing device with a processor, a second workflow protocol from the plurality of workflow protocols, wherein:

the selection of the second workflow protocol is based on the second value, the second workflow protocol includes second workflow data that represents a plurality of second actions to be performed by the second navigator device for the second patient, and the second workflow protocol is different from the first workflow protocol; and receiving, by a computing device with a processor, a second input indicating completion of at least one of the plurality of second actions represented in the second workflow data, and updating the second patient data with a second indication corresponding to the completion of the at least one plurality of second actions.

2. The computer-implemented method of claim 1, wherein retrieving the first clinical result data from the first data source comprises determining the units of the first clinical result data.

3. The computer-implemented method of claim 1, wherein the categorization rule is associated with a plurality of triggers having different units.

4. The computer-implemented method of claim 1, further comprising selecting the trigger having units matching the units of the first clinical result data.

5. The computer-implemented method of claim 1, wherein each of the first and second values indicates if the threshold has been exceeded.

6. The computer-implemented method of claim 1, further comprising, providing the first clinical result data, the first value, and the patient data for the identified patient to the first navigator device.

7. The computer-implemented method of claim 1, further comprising:

providing the first clinical result data, the first value, and the patient data for the identified patient to a physician;

providing the first workflow protocol to the physician; and receiving an input from the physician selecting the first workflow protocol.

8. The computer-implemented method of claim 1, wherein selecting the first navigator device further comprises:

identifying a geographical region associated with the first patient;

determining that the first navigator device is located within the geographical region; and selecting the first navigator device based on the determination that the first navigator device is located within the geographical region.

9. A system, comprising:

one or more data processors; and a non-transitory computer-readable storage medium containing instructions which, when executed on the one or more data processors, cause the one or more data processors to perform operations including:

identifying a set of data sources that is associated with a program optimization system, wherein the set of data sources includes one or more data sources that store clinical data, and wherein the program optimization system is associated with a defined parameter condition used for determining whether to include additional data sources into the set of data sources;

receiving a communication from a first data source not included in the set of data sources, wherein the communication includes:

data representing a request to include the first data source into the set of data sources, and a report metric from the first data source, wherein the report metric identifies a type of the first data source and a result of the first data source;

in response to receiving the communication, automatically determining whether the report metric satisfies the defined parameter condition;

including the first data source into the set of data sources based on the determination, wherein the inclusion of the first data source into the set of data sources indicates that the report metric satisfies with the defined parameter condition;

accessing a database storing patient data, wherein:

the patient data identifies a plurality of patients, the database stores first patient data associated with a first patient and second patient data associated with a second patient, the stored first patient data including a first priority indicator representing a first priority and the second patient data including a second priority indicator representing a second priority, and the first patient data being prioritized over the second patient data based on, at least in part, the first priority indicator and the second priority indicator;

identifying a second data source from the set of data stores, wherein the second data source stores clinical data corresponding to one or more types of clinical result;

querying the second data source for first clinical result data corresponding to the first patient data and second clinical result data corresponding to the second patient data;

selecting a categorization rule in accordance with each of the first clinical result and the second clinical result, wherein:

the categorization rule is associated with a trigger protocol that triggers one or more workflows based on a comparison of the first clinical result or the second clinical result with a threshold, the threshold being determined using the categorization rule;

determining that the first clinical result data and the second clinical result data are of the same type of clinical result, the determination being based on the categorization rule;

comparing each of the first clinical result data and the second clinical result data with the threshold, wherein:

the comparison results in a first value indicating a difference between the first clinical result data and the threshold, the comparison further results in a second value indicating a difference between the second clinical result data and the threshold, and the first value corresponds to the first priority indicator and the second value corresponds to the second priority indicator;

determining that one or more navigator devices are to be selected for performing workflows for each of the first patient data and the second patient data;

selecting a first navigator device from a plurality of navigator devices, wherein the selection of the first navigator device includes:

identifying the plurality of navigator devices based on the determination that one or more navigator devices are to be selected for performing workflows, each of the plurality of navigator devices being associated with one or more attributes, determining, for each navigator device of the plurality of navigator devices, whether the associated one or more attributes corresponds to the first value, and selecting the first navigator device when the one or more attributes associated with the first navigator device correspond to the first value;

selecting a first workflow protocol from a plurality of workflow protocols, wherein the selection of the first workflow protocol is based on the first value, wherein the first workflow protocol includes first workflow data that represents a plurality of first actions to be performed by the first navigator device for the first patient;

receiving a first input indicating completion of at least one of the plurality of first actions, and updating the first patient data with a first indication corresponding to the completion of the at least one plurality of first actions;

selecting a second navigator device from the plurality of navigator devices, wherein the selection of the second navigator device includes:

identifying the plurality of navigator devices, determining, for each navigator device of the plurality of navigator devices, whether the associated one or more attributes corresponds to the second value, and selecting the second navigator device when the one or more attributes associated with the second navigator device correspond to the second value, wherein the selected first navigator device is different from the selected second navigator device due to the first value having a different magnitude than the second value;

selecting a second workflow protocol from the plurality of workflow protocols, wherein:

the selection of the second workflow protocol is based on the second value, the second workflow protocol includes second workflow data that represents a plurality of second actions to be performed by the second navigator device for the second patient, and the second workflow protocol is different from the first workflow protocol; and receiving a second input indicating completion of at least one of the plurality of second actions represented in the second workflow data, and updating the second patient data with a second indication corresponding to the completion of the at least one plurality of second actions.

10. The system of claim 9, wherein retrieving the first clinical result from the first data source comprises determining the units of the first clinical result data.

11. The system of claim 9, wherein the categorization rule is associated with a plurality of triggers having different units.

12. The system of claim 9, wherein the operations further comprise selecting the trigger having units matching the units of the first clinical result data.

13. The system of claim 9, wherein each of the first and second values indicates if the threshold has been exceeded.

14. The system of claim 9, further comprising, providing the first clinical result data, the first value, and the patient data for the identified patient to the first navigator device.

15. The system of claim 9, wherein the operations further comprise:

providing the first clinical result data, the first value, and the patient data for the identified patient to a physician;

providing the first workflow protocol to the physician; and receiving an input from the physician selecting the first workflow protocol.

16. A computer-program product tangibly embodied in a non-transitory machine-readable storage medium, including instructions configured to cause a data processing apparatus to perform operations including:

identifying a set of data sources that is associated with a program optimization system, wherein the set of data sources includes one or more data sources that store clinical data, and wherein the program optimization system is associated with a defined parameter condition used for determining whether to include additional data sources into the set of data sources;

receiving a communication from a first data source not included in the set of data sources, wherein the communication includes:

data representing a request to include the first data source into the set of data sources, and a report metric from the first data source, wherein the report metric identifies a type of the first data source and a result of the first data source;

in response to receiving the communication, automatically determining whether the report metric satisfies the defined parameter condition;

including the first data source into the set of data sources based on the determination, wherein the inclusion of the first data source into the set of data sources indicates that the report metric satisfies with the defined parameter condition;

accessing a database storing patient data, wherein:

the patient data identifies a plurality of patients, the database stores first patient data associated with a first patient and second patient data associated with a second patient, the stored first patient data including a first priority indicator representing a first priority and the second patient data including a second priority indicator representing a second priority, and the first patient data being prioritized over the second patient data based on, at least in part, the first priority indicator and the second priority indicator;

identifying a second data source from the set of data stores, wherein the second data source stores clinical data corresponding to one or more types of clinical result;

querying the second data source for first clinical result data corresponding to the first patient data and second clinical result data corresponding to the second patient data;

selecting a categorization rule in accordance with each of the first clinical result and the second clinical result, wherein:

the categorization rule is associated with a trigger protocol that triggers one or more workflows based on a comparison of the first clinical result or the second clinical result with a threshold, the threshold being determined using the categorization rule;

determining that the first clinical result data and the second clinical result data are of the same type of clinical result, the determination being based on the categorization rule;

comparing each of the first clinical result data and the second clinical result data with the threshold, wherein:

the comparison results in a first value indicating a difference between the first clinical result data and the threshold, the comparison further results in a second value indicating a difference between the second clinical result data and the threshold, and the first value corresponds to the first priority indicator and the second value corresponds to the second priority indicator;

determining that one or more navigator devices are to be selected for performing workflows for each of the first patient data and the second patient data;

selecting a first navigator device from a plurality of navigator devices, wherein the selection of the first navigator device includes:

identifying the plurality of navigator devices based on the determination that one or more navigator devices are to be selected for performing workflows, each of the plurality of navigator devices being associated with one or more attributes, determining, for each navigator device of the plurality of navigator devices, whether the associated one or more attributes corresponds to the first value, and selecting the first navigator device when the one or more attributes associated with the first navigator device correspond to the first value;

selecting a first workflow protocol from a plurality of workflow protocols, wherein the selection of the first workflow protocol is based on the first value, wherein the first workflow protocol includes first workflow data that represents a plurality of first actions to be performed by the first navigator device for the first patient;

receiving a first input indicating completion of at least one of the plurality of first actions, and updating the first patient data with a first indication corresponding to the completion of the at least one plurality of first actions;

selecting a second navigator device from the plurality of navigator devices, wherein the selection of the second navigator device includes:

identifying the plurality of navigator devices, determining, for each navigator device of the plurality of navigator devices, whether the associated one or more attributes corresponds to the second value, and selecting the second navigator device when the one or more attributes associated with the second navigator device correspond to the second value, wherein the selected first navigator device is different from the selected second navigator device due to the first value having a different magnitude than the second value;

selecting a second workflow protocol from the plurality of workflow protocols, wherein:

the selection of the second workflow protocol is based on the second value, the second workflow protocol includes second workflow data that represents a plurality of second actions to be performed by the second navigator device for the second patient, and the second workflow protocol is different from the first workflow protocol; and receiving a second input indicating completion of at least one of the plurality of second actions represented in the second workflow data, and updating the second patient data with a second indication corresponding to the completion of the at least one plurality of second actions.

17. The computer-program product of claim 16, wherein the operations further comprise identifying a type of the first clinical result data generated by the second data source and a format and units of the first clinical result data.

18. The computer-program product of claim 16, wherein the operations further comprise determining if a type, format, and units of the first clinical result data generated by the second data source meet a first criteria, wherein the first patient data is updated if the type, format, and units of the first clinical result data generated by the second data source meet the first criteria.

19. The computer-program product of claim 16, wherein the operations further comprise:

retrieving third clinical result data from the second data source, wherein the third clinical result data relates to the health of a member of the healthcare organization;

generating a third value by comparing the third clinical result to a second threshold, wherein the third value indicates that the third clinical result exceeds the second threshold in the first direction, wherein exceeding the second threshold in the first direction is associated with a third workflow protocol; and updating the patient data with an indicator identifying the member of a healthcare organization as a candidate for the third workflow protocol.

* * * * *